United States Patent
Jackson et al.

(10) Patent No.: US 11,357,674 B2
(45) Date of Patent: Jun. 14, 2022

(54) RADIALLY TENSIONED WOUND OR SKIN TREATMENT DEVICES AND METHODS

(71) Applicant: Neodyne Biosciences, Inc., Newark, CA (US)

(72) Inventors: Jasper Jackson, Neward, CA (US); William R. Beasley, Los Altos, CA (US); John A. Zepeda, Los Altos, CA (US); Richard T. Caligaris, San Anselmo, CA (US)

(73) Assignee: NEODYNE BIOSCIENCES, INC., Newark, CA (US)

( * ) Notice: Subject to any disclaimer, the term of this patent is extended or adjusted under 35 U.S.C. 154(b) by 40 days.

(21) Appl. No.: 16/285,032

(22) Filed: Feb. 25, 2019

(65) Prior Publication Data

US 2019/0358100 A1  Nov. 28, 2019

Related U.S. Application Data

(63) Continuation of application No. 13/789,512, filed on Mar. 7, 2013, now Pat. No. 10,213,350, which is a
(Continued)

(51) Int. Cl.
*A61F 15/00* (2006.01)
*A61F 13/00* (2006.01)

(52) U.S. Cl.
CPC ...... *A61F 15/005* (2013.01); *A61F 13/00038* (2013.01)

(58) Field of Classification Search
CPC .. A61F 2013/00804; A61F 2013/00317; A61F 2013/00329; A61F 2013/00334; A61F 2013/00838; A61F 2013/00038; A61F 2013/00085; A61F 15/00; A61F 15/005; A61F 2013/00817;
(Continued)

(56) References Cited

U.S. PATENT DOCUMENTS

| 114,750 A | 5/1871 | Battersby |
| 363,538 A | 5/1887 | Penny |

(Continued)

FOREIGN PATENT DOCUMENTS

| CA | 2321491 A1 | 9/1999 |
| CA | 2621387 A1 | 3/2007 |

(Continued)

OTHER PUBLICATIONS

"NHSSB Wound Management Manual", Northern Health and Social Services Board, 2005, pp. 1-97.
(Continued)

*Primary Examiner* — Camtu T Nguyen
(74) *Attorney, Agent, or Firm* — Dorsey & Whitney LLP

(57) ABSTRACT

Devices, kits and methods described herein may be for treatment to skin, including but not limited to wound healing, the treatment, amelioration, and/or prevention of scars or keloids. An applicator and/or tensioning device may be used to apply a dressing to a subject. The applicator and/or tensioning device applies and/or maintains a strain in an elastic dressing, wherein at least some of the strain is out-of-plane or at a non-orthogonal, non-parallel and non-aligned orientation to other strains in the dressing.

12 Claims, 41 Drawing Sheets

Related U.S. Application Data continuation of application No. PCT/US2013/025449, filed on Feb. 28, 2013.

(60) Provisional application No. 61/596,708, filed on Feb. 8, 2012.

(58) Field of Classification Search
CPC .. A61F 2013/00829; A61F 2013/00834; A61F 13/00038; A61F 13/00085; A61B 17/08; A61B 17/085; A61B 2017/088; A61B 17/0466; A61B 2017/081
See application file for complete search history.

(56) References Cited

U.S. PATENT DOCUMENTS

| | | |
|---|---|---|
| 633,050 A | 9/1899 | Spenard |
| 1,074,413 A | 9/1913 | Baun et al. |
| 1,774,489 A | 8/1930 | David |
| 1,969,188 A | 8/1934 | Spicer |
| 2,018,517 A | 10/1935 | Edward |
| 2,303,131 A | 11/1942 | Morgan |
| 2,371,978 A | 3/1945 | Perham |
| 2,421,193 A | 5/1947 | James |
| 2,472,009 A | 5/1949 | James |
| 2,714,382 A | 8/1955 | Solis |
| 2,722,220 A | 11/1955 | Mestrand |
| 2,762,371 A | 9/1956 | Guio |
| 3,103,218 A | 9/1963 | Ajemian |
| 3,402,716 A | 9/1968 | Baxter |
| 3,487,836 A | 1/1970 | Niebel et al. |
| 3,528,426 A | 9/1970 | Vukojevic |
| 3,575,782 A | 4/1971 | Hansen |
| 3,613,679 A | 10/1971 | Bijou |
| 3,645,835 A | 2/1972 | Hodgson |
| 3,698,395 A | 10/1972 | Hasson |
| 3,863,640 A | 2/1975 | Haverstock |
| 3,926,193 A | 12/1975 | Hasson |
| 3,933,158 A | 1/1976 | Haverstock |
| 3,983,878 A | 10/1976 | Kawchitch |
| 4,038,989 A | 8/1977 | Romero-sierra et al. |
| 4,073,298 A | 2/1978 | Le |
| 4,114,624 A | 9/1978 | Haverstock |
| 4,141,363 A | 2/1979 | James et al. |
| 4,173,131 A | 11/1979 | Melton et al. |
| 4,222,383 A | 9/1980 | Schossow |
| 4,282,005 A | 8/1981 | Sato et al. |
| 4,346,700 A | 8/1982 | Dunshee et al. |
| 4,370,981 A | 2/1983 | Sanderson |
| 4,413,621 A | 11/1983 | Mccracken et al. |
| 4,423,731 A | 1/1984 | Roomi |
| 4,425,176 A | 1/1984 | Shibano et al. |
| 4,447,482 A | 5/1984 | Heinzelman et al. |
| 4,496,535 A | 1/1985 | Gould et al. |
| 4,531,521 A | 7/1985 | Haverstock |
| 4,535,772 A | 8/1985 | Sheehan |
| 4,539,990 A | 9/1985 | Stivala |
| 4,549,653 A | 10/1985 | Lauritzen |
| 4,598,004 A | 7/1986 | Heinecke |
| 4,605,005 A | 8/1986 | Sheehan |
| 4,646,731 A | 3/1987 | Brower |
| 4,653,492 A | 3/1987 | Parsons |
| 4,696,301 A | 9/1987 | Barabe |
| 4,699,133 A | 10/1987 | Schaefer et al. |
| 4,702,251 A | 10/1987 | Sheehan |
| 4,706,661 A | 11/1987 | Barrett |
| 4,732,146 A | 3/1988 | Fasline et al. |
| 4,742,826 A | 5/1988 | Mclorg |
| 4,753,232 A | 6/1988 | Ward |
| 4,780,168 A | 10/1988 | Beisang et al. |
| 4,787,381 A | 11/1988 | Hubbard et al. |
| 4,807,613 A | 2/1989 | Koehnke et al. |
| 4,815,457 A | 3/1989 | Mazars et al. |
| 4,815,468 A | 3/1989 | Annand |
| 4,825,866 A | 5/1989 | Pierce |
| 4,881,546 A | 11/1989 | Kaessmann |
| 4,915,102 A | 4/1990 | Kwiatek et al. |
| 4,917,929 A | 4/1990 | Heinecke |
| 4,924,866 A | 5/1990 | Yoon |
| 4,950,282 A | 8/1990 | Beisang et al. |
| RE33,353 E | 9/1990 | Heinecke |
| 4,984,584 A | 1/1991 | Hansen et al. |
| 5,011,492 A | 4/1991 | Heimerl et al. |
| 5,026,389 A | 6/1991 | Thieler |
| 5,047,047 A | 9/1991 | Yoon |
| 5,058,579 A | 10/1991 | Terry et al. |
| 5,066,299 A | 11/1991 | Bellingham |
| 5,106,629 A | 4/1992 | Cartmell et al. |
| 5,127,412 A | 7/1992 | Cosmetto et al. |
| 5,176,703 A | 1/1993 | Peterson |
| 5,234,462 A | 8/1993 | Pavletic |
| 5,259,835 A | 11/1993 | Clark et al. |
| 5,263,965 A | 11/1993 | Roth |
| 5,263,970 A | 11/1993 | Preller |
| 5,333,753 A | 8/1994 | Etheredge |
| 5,383,900 A | 1/1995 | Krantz |
| 5,507,775 A | 4/1996 | Ger et al. |
| 5,520,762 A | 5/1996 | Rasmussen et al. |
| 5,522,879 A | 6/1996 | Scopelianos |
| 5,545,713 A | 8/1996 | Krejci et al. |
| 5,549,713 A | 8/1996 | Kim |
| 5,552,162 A | 9/1996 | Lee |
| 5,562,705 A | 10/1996 | Whiteford |
| 5,628,724 A | 5/1997 | Debusk et al. |
| 5,649,960 A | 7/1997 | Pavletic |
| 5,662,624 A | 9/1997 | Sundstroem et al. |
| 5,662,714 A | 9/1997 | Charvin et al. |
| 5,662,717 A | 9/1997 | Burns |
| 5,713,842 A | 2/1998 | Kay |
| 5,723,009 A | 3/1998 | Frechet et al. |
| 5,758,662 A | 6/1998 | Hall |
| 5,759,560 A | 6/1998 | Dillon |
| 5,779,659 A | 7/1998 | Allen |
| 5,820,877 A | 10/1998 | Yamaguchi et al. |
| 5,885,254 A | 3/1999 | Matyas |
| 5,891,076 A | 4/1999 | Fabo |
| 5,919,476 A | 7/1999 | Fischer et al. |
| 5,931,800 A | 8/1999 | Rasmussen et al. |
| 5,947,998 A | 9/1999 | Cartmell et al. |
| 5,998,694 A | 12/1999 | Jensen et al. |
| 6,007,564 A | 12/1999 | Haverstock |
| 6,043,406 A | 3/2000 | Sessions et al. |
| 6,093,465 A | 7/2000 | Gilchrist et al. |
| 6,120,525 A | 9/2000 | Westcott |
| 6,255,552 B1 | 7/2001 | Cummings et al. |
| 6,264,976 B1 | 7/2001 | Heinecke et al. |
| 6,284,941 B1 | 9/2001 | Cox et al. |
| 6,297,420 B1 | 10/2001 | Heincke |
| 6,297,423 B1 | 10/2001 | Schoenfeldt et al. |
| 6,343,224 B1 | 1/2002 | Parker |
| 6,346,653 B1 | 2/2002 | Sessions et al. |
| 6,410,818 B1 | 6/2002 | Oyaski |
| 6,469,066 B1 | 10/2002 | Dosch et al. |
| 6,485,503 B2 | 11/2002 | Jacobs et al. |
| 6,495,230 B1 | 12/2002 | Do |
| 6,570,051 B1 | 5/2003 | Beaudry |
| 6,572,878 B1 | 6/2003 | Blaine |
| 6,573,419 B2 | 6/2003 | Naimer |
| 6,634,653 B2 | 10/2003 | Chatterjea |
| 6,726,696 B1 | 4/2004 | Houser et al. |
| 6,759,481 B2 | 7/2004 | Tong |
| 6,822,133 B2 | 11/2004 | Lebner |
| 6,831,205 B2 | 12/2004 | Lebner |
| 6,870,074 B2 | 3/2005 | Gilman |
| 6,986,855 B1 | 1/2006 | Hood et al. |
| 7,066,182 B1 | 6/2006 | Dunshee |
| 7,066,934 B2 | 6/2006 | Kirsch |
| 7,122,712 B2 | 10/2006 | Lutri et al. |
| 7,135,606 B1 | 11/2006 | Dozier et al. |
| 7,227,050 B2 | 6/2007 | Sigurjonsson et al. |
| 7,332,641 B2 | 2/2008 | Lebner et al. |
| 7,354,446 B2 | 4/2008 | Lebner |
| 7,414,168 B2 | 8/2008 | Lebner |
| 7,456,332 B2 | 11/2008 | Beaudry |

(56) References Cited

U.S. PATENT DOCUMENTS

| | | |
|---|---|---|
| 7,511,185 B2 | 3/2009 | Lebner |
| 7,563,941 B2 | 7/2009 | Lebner et al. |
| 7,683,234 B2 | 3/2010 | Gurtner et al. |
| 7,834,232 B2 | 11/2010 | Rastegar et al. |
| 8,063,263 B2 | 11/2011 | Gurtner et al. |
| 8,168,850 B2 | 5/2012 | Gurtner et al. |
| 8,183,428 B2 | 5/2012 | Gurtner et al. |
| 8,389,791 B2 | 3/2013 | Gurtner et al. |
| 8,395,011 B2 | 3/2013 | Zepeda et al. |
| 8,592,640 B2 | 11/2013 | Zepeda et al. |
| 8,674,164 B2 | 3/2014 | Zepeda et al. |
| 9,827,447 B1 | 11/2017 | Levi et al. |
| 10,213,350 B2 | 2/2019 | Jackson et al. |
| 2002/0013300 A1 | 1/2002 | Capelli-Schellpfeffer |
| 2002/0015816 A1 | 2/2002 | Shingai et al. |
| 2002/0045698 A1 | 6/2002 | Ayama et al. |
| 2002/0092783 A1 | 11/2002 | Banner |
| 2002/0193723 A1 | 12/2002 | Girardin et al. |
| 2003/0014053 A1 | 1/2003 | Nguyen et al. |
| 2003/0040687 A1 | 2/2003 | Boynton et al. |
| 2003/0092969 A1 | 5/2003 | Omalley et al. |
| 2003/0220700 A1 | 11/2003 | Hammer et al. |
| 2005/0033215 A1 | 2/2005 | Lebner |
| 2005/0034731 A1 | 2/2005 | Rousseau et al. |
| 2005/0070956 A1 | 3/2005 | Rousseau |
| 2005/0080453 A1 | 4/2005 | Lebner et al. |
| 2005/0095275 A1 | 5/2005 | Zhu et al. |
| 2005/0095276 A1 | 5/2005 | Kartheus et al. |
| 2005/0125051 A1 | 6/2005 | Eidenschink et al. |
| 2005/0245966 A1 | 11/2005 | Hammerslag et al. |
| 2005/0274453 A1 | 12/2005 | Anvar |
| 2006/0009099 A1 | 1/2006 | Jonn et al. |
| 2006/0020235 A1 | 1/2006 | Siniaguine |
| 2006/0037091 A1 | 2/2006 | Gurtner et al. |
| 2006/0064024 A1 | 3/2006 | Schnall |
| 2006/0246802 A1 | 11/2006 | Hughes et al. |
| 2006/0282135 A1 | 12/2006 | Tankovich |
| 2007/0093161 A1 | 4/2007 | Eede et al. |
| 2007/0142761 A1 | 6/2007 | Aali |
| 2007/0178121 A1 | 8/2007 | First et al. |
| 2007/0191752 A1 | 8/2007 | Lebner |
| 2007/0282235 A1 | 12/2007 | Beaudry |
| 2007/0282374 A1 | 12/2007 | Sogard et al. |
| 2008/0033334 A1 | 2/2008 | Gurtner et al. |
| 2008/0051687 A1 | 2/2008 | Rogers |
| 2008/0208098 A1 | 8/2008 | Rennix |
| 2008/0228220 A1 | 9/2008 | Weiser |
| 2008/0269657 A1* | 10/2008 | Brenneman ............ A61B 46/10 602/41 |
| 2009/0131845 A1 | 5/2009 | Gurtner et al. |
| 2009/0131846 A1 | 5/2009 | Gurtner et al. |
| 2009/0163844 A1 | 6/2009 | Gurtner et al. |
| 2009/0177136 A1 | 7/2009 | Liedtke et al. |
| 2010/0191253 A1 | 7/2010 | Oostman, Jr. et al. |
| 2010/0280428 A1 | 11/2010 | Widgerow et al. |
| 2011/0054283 A1 | 3/2011 | Shuler |
| 2011/0152738 A1* | 6/2011 | Zepeda ............... A61F 13/0266 602/53 |
| 2011/0288506 A1* | 11/2011 | Chowdhury ......... A61K 9/7084 604/290 |
| 2011/0319798 A1 | 12/2011 | Digrazia |
| 2012/0035521 A1 | 2/2012 | Zepeda et al. |
| 2012/0046586 A1 | 2/2012 | Gurtner et al. |
| 2012/0046590 A1 | 2/2012 | Yock et al. |
| 2012/0046591 A1 | 2/2012 | Gurtner et al. |
| 2012/0083724 A1 | 4/2012 | Zepeda et al. |
| 2012/0203273 A1 | 8/2012 | Riskin et al. |
| 2012/0221044 A1 | 8/2012 | Archibald et al. |
| 2012/0226214 A1 | 9/2012 | Gurtner et al. |
| 2012/0226306 A1 | 9/2012 | Jackson et al. |
| 2013/0012858 A1 | 1/2013 | Jackson et al. |
| 2013/0110026 A1 | 5/2013 | Jackson et al. |
| 2013/0184629 A1 | 7/2013 | Gurtner et al. |
| 2013/0190655 A1 | 7/2013 | Jackson et al. |
| 2013/0190673 A1 | 7/2013 | Gurtner et al. |

FOREIGN PATENT DOCUMENTS

| | | |
|---|---|---|
| CN | 1414842 A | 4/2003 |
| CN | 1608604 A | 4/2005 |
| CN | 101836918 A | 9/2010 |
| CN | 102665623 B | 12/2014 |
| EP | 2161011 A1 | 3/2010 |
| EP | 2464322 A2 | 6/2012 |
| JP | 2004515256 A | 5/2004 |
| JP | 2004223087 A | 8/2004 |
| JP | 2004536898 A | 12/2004 |
| JP | 2006513748 A | 4/2006 |
| JP | 2007537781 A | 12/2007 |
| JP | 2009545382 A | 12/2009 |
| JP | 2013501591 A | 1/2013 |
| KR | 20120066015 A | 6/2012 |
| RU | 2019138 C1 | 9/1994 |
| WO | 1997017919 A1 | 5/1997 |
| WO | 1997030700 A2 | 8/1997 |
| WO | 1997030700 A3 | 8/1997 |
| WO | 2000053139 A1 | 9/2000 |
| WO | 2001039693 A2 | 6/2001 |
| WO | 2002087645 A1 | 11/2002 |
| WO | 2004060413 A1 | 7/2004 |
| WO | 2004073567 A1 | 9/2004 |
| WO | 2005079674 A1 | 9/2005 |
| WO | 2005096891 A2 | 10/2005 |
| WO | 2006124671 A2 | 11/2006 |
| WO | 2006124671 A3 | 4/2007 |
| WO | 2008019051 A2 | 2/2008 |
| WO | 2008019051 A3 | 4/2008 |
| WO | 2011019859 A2 | 2/2011 |
| WO | 2011019859 A3 | 4/2011 |
| WO | 2011159623 A1 | 12/2011 |
| WO | 2012094648 A1 | 7/2012 |
| WO | 2012119131 A1 | 9/2012 |
| WO | 2014021934 A2 | 2/2014 |
| WO | 2014021934 A3 | 3/2015 |

OTHER PUBLICATIONS

3M Healthcare, "3M™ S Surgical Skin Closure, Poster of Available Sizes", 3M Healthcare, St. Paul, MN, 3 pages.

3M Healthcare, "3M™ Steri-Strip™ Adhesive Skin Closures (Reinforced): Commonly Asked Questions", 3M Healthcare: St. Paul, MN, Jun. 27, 2002, pp. 1-4.

3M Healthcare, "3M™ Steri-Strip™ S Surgical Skin Closure Application Examples, Comparisons and Results", 3M Healthcare, St. Paul, MN, 2007, 4 pages.

3M Healthcare, "3M™ Steri-Strip™ S Surgical Skin Closure Application Instructions", 3M Healthcare, St. Paul, MN, 2007, 2 pages.

3M Healthcare, "3M™ Steri-Strip™ S Surgical Skin Closure The Simple, Non-Invasive Alternative to Staples and Sutures from the Steri-Strip Family", 3M Healthcare, St. Paul, MN, 2006, 2 pages.

3M Healthcare, "3M™ Steri-Strip™ S Surgical Skin Closure, Patient Care Information", 3M Healthcare, St. Paul, MN, 2006, 2 pages.

3M Healthcare, "3M™ Steri-Strip™ S Surgical Skin Closure Commonly Asked Questions", 3M Healthcare, St. Paul, MN, Oct. 19, 2006, pp. 1-8.

3M Healthcare, "Reducing the Risk of Superficial Skin Damage Related to Adhesive Use", 3M Healthcare, St. Paul, MN, 2001, 2 pages.

3M Healthcare, "Steri-Strip: Skin Closures", Product Insert, 3M Healthcare, St. Paul, MN, 2003, 1 page.

3M Healthcare, "They Say Every Scar Tells A Story", 3M Healthcare, St. Paul, MN, 2006, 1 page.

3M Healthcare, "Tips for Trouble-Free Taping", 3M Healthcare, St. Paul, MN, May 2004, 4 pages.

3M Healthcare., "3M™ S Surgical Skin Closure", 3M Healthcare, St. Paul, MN, 1 page.

Anonymous, "3M™ Steri-Strip™ Adhesive Skin Closures", 3M Brochure, 2003, 12 pages.

Anonymous, "3M™ Tegaderm™ Family of Transparent Dressings", 3M Brochure, 2005, 6 pages.

(56) References Cited

OTHER PUBLICATIONS

Anonymous, "Avocet Polymer Technologies Inc.", available at <http://www.avocetcorp.com/index.html>, last visited Nov. 5, 2007, 1 page.
Anonymous, "Avogel Scar Hydrogel", available at <http://www.avocetcorp.com/avogel_scar_hydrogel.html>, last visited Nov. 5, 2007, 2 pages.
Anonymous, "Avosil Ointment", available at <http://www.avocetcorp.com/avosil.html>, last visited Nov. 5, 2007, 3 pages.
Anonymous, "Mepiform Instructions of Use", Tendra Corporation Brochure, 2 pages.
Anonymous, "Silicone Scar Bandage: Standard Wound Healing Application", available at <http://www.thejamushop.com/silicon_sheet_for_keloids.htm>, last visited on Mar. 18, 2009, 4 pages.
Brace, "Definition of Brace", Merriam Webster, Available at <www.merriam-webster.com>, 2015, 4 pages.
Canica Design Inc, "ABRA Abdominal Wall Closure Set: A Dynamic Wound Closure System", Instructions for Use, available online at <http://www.canica.com/instructions/1D1544%20ABRA%20CWK08.pdf>, last visited on Sep. 10, 2009, pp. 1-11.
Decision for Grant received for Korean Patent Application No. 10-2014-7005383, dated Dec. 10, 2014, 3 pages.
Decision of Grant received for Chinese Patent Application No. 201280012003.6, dated Feb. 3, 2015, 2 pages.
Decision to Grant received for European Patent Application No. 12752239.9, dated Apr. 1, 2016, 2 pages.
Decision to Grant Received for Korean Patent Application No. 10-2009-4003220, dated May 14, 2014, 3 pages.
English Translation of Office Action dated May 22, 2019 for Korean application No. 10-2014-7025268.
English translation of Office Action for BR Application No. 1120140195870, dated Oct. 2, 2019.
Extended European Search Report (includes Supplementary European Search Report and Search Opinion) received for European Patent Application No. 12732236.0, dated Jun. 29, 2015, 6 pages.
Extended European Search Report (includes Supplementary European Search Report and Search Opinion) received for European Patent Application No. 12752239.9, dated Oct. 1, 2014, 7 pages.
Extended European Search Report (includes Supplementary European Search Report and Search Opinion) received for European Patent Application No. 13825488.6, dated Feb. 23, 2016, 6 pages.
Extended European Search Report and European Search Opinion received for European Patent Application No. 10808724.8, dated Aug. 19, 2013, 8 pages.
Intention to Grant received for European Patent Application No. 12752239.9, dated Feb. 11, 2016, 3 pages.
Intention to Grant received for European Patent Application No. 12752239.9, dated Sep. 24, 2015, 5 pages.
International Preliminary Report on Patentability received for PCT Patent Application No. PCT/US2007/017320, dated Feb. 3, 2009, 8 pages.
International Preliminary Report on Patentability received for PCT Patent Application No. PCT/US2010/045239, dated Feb. 23, 2012, 10 pages.
International Preliminary Report on Patentability received for PCT Patent Application No. PCT/US2012/020561, dated Jul. 18, 2013, 8 pages.
International Preliminary Report on Patentability received for PCT Patent Application No. PCT/US2012/025510, dated Aug. 29, 2013, 10 pages.
International Preliminary Report on Patentability received for PCT Patent Application No. PCT/US2012/027618, dated Sep. 12, 2013, 12 pages.
International Preliminary Report on Patentability received for PCT Patent Application No. PCT/US2013/025449, dated Feb. 5, 2015, 7 pages.
International Search Report and Written Opinion received for PCT Patent Application No. PCT/US2007/017320, dated Feb. 7, 2008, 10 pages.
International Search Report and Written Opinion received for PCT Patent Application No. PCT/US2010/045239, dated Feb. 8, 2011, 12 pages.
International Search Report and Written Opinion received for PCT Patent Application No. PCT/US2012/020561, dated May 1, 2012, 9 pages.
International Search Report and Written Opinion received for PCT Patent Application No. PCT/US2012/025510, dated May 29, 2012, 11 pages.
International Search Report and Written Opinion received for PCT Patent Application No. PCT/US2012/027618, dated Jun. 28, 2012, 11 pages.
International Search Report and Written Opinion received for PCT Patent Application No. PCT/US2013/25449, dated Apr. 23, 2013, 8 pages.
Invitation to Pay Additional Fees received for PCT Patent Application No. PCT/US2010/045239, dated Nov. 29, 2010, 2 pages.
Mask, "Definition of Mask", Merriam Webster, Available online at <www.merriam-webster.com>, 2015, 4 pages.
Notice of Acceptance received for Australian Patent Application No. 2010282523, dated Jul. 2, 2015, 2 pages.
Notice of Allowance received for Canadian Patent Application No. 2,659,772, dated Sep. 14, 2015, 1 page.
Notice of Allowance received for Canadian Patent Application No. 2,770,834, dated Apr. 8, 2016, 1 page.
Notice of Allowance received for Chinese Patent Application No. 201310474149.9, dated Jan. 13, 2016, 2 pages.
Notice of Allowance received for Israel Patent Application No. 218020, dated Dec. 11, 2014, 4 pages.
Notice of Allowance received for Japanese Patent Application No. 2009-0522879, dated Mar. 17, 2014, 6 pages.
Notice of Allowance received for Japanese Patent Application No. 2012-524855, dated Apr. 30, 2015, 3 pages.
Notice of Allowance received for Japanese Patent Application No. 2013-037053 dated Jan. 6, 2015, 3 pages.
Office Action received for Australian Patent Application No. 2010282523, dated May 6, 2014, 4 pages.
Office Action received for Australian Patent Application No. 2012204174, dated Aug. 4, 2015, 2 pages.
Office Action received for Canadian Patent Application No. 2,659,772, dated Oct. 30, 2013, 3 pages.
Office Action received for Canadian Patent Application No. 2,659,772, dated Sep. 11, 2014, 2 pages.
Office Action received for Canadian Patent Application No. 2,770,834, dated Sep. 25, 2015, 3 pages.
Office Action received for Chinese Patent Application No. 201080045471.4, dated Sep. 29, 2013, 4 pages.
Office Action received for Chinese Patent Application No. 201080045471.4, dated May 21, 2014, 6 pages.
Office Action received for Chinese Patent Application No. 20120021431.5 dated Jul. 17, 2015, 4 pages.
Office Action received for Chinese Patent Application No. 201280012003.6, dated Jun. 30, 2014, 9 pages.
Office Action received for Chinese Patent Application No. 2012800211431.5, dated Apr. 1, 2016, 4 pages.
Office Action received for Chinese Patent Application No. 201280021431.5, dated Sep. 22, 2014, 3 pages.
Office Action received for Chinese Patent Application No. 20130012873.8, dated Mar. 3, 2016, 4 pages.
Office Action received for Chinese Patent Application No. 201310474149.9, dated Jan. 27, 2015, 10 pages.
Office Action received for Chinese Patent Application No. 201310474149.9, dated Jul. 27, 2015, 6 pages.
Office Action received for European Patent Application No. 07836471, dated Jul. 13, 2010, 7 pages.
Office Action received for European Patent Application No. 07836471.8, dated Nov. 6, 2015, 7 pages.
Office Action received for European Patent Application No. 10808724.8, dated Feb. 8, 2016, 4 pages.
Office Action received for European Patent Application No. 10808724.8, dated Jan. 15, 2015, 4 pages.
Office Action received for Indian Patent Application No. 654/DELNP/2009, dated Jul. 31, 2014, 4 pages.

(56) References Cited

OTHER PUBLICATIONS

Office Action received for Israeli Patent Application No. 218020, dated Dec. 1, 2013, 12 pages.
Office Action received for Japanese Patent Application No. 2012-524855, dated Apr. 14, 2014, 7 pages.
Office Action received for Japanese Patent Application No. 2012-524855, dated Oct. 24, 2014, 5 pages.
Office Action received for Japanese Patent Application No. 2013-037053, dated Mar. 17, 2014, 5 pages.
Office Action received for Japanese Patent Application No. 2013-548594, dated Jul. 7, 2015, 10 pages.
Office Action received for Japanese Patent Application No. 2014-123100, dated Mar. 25, 2016, 2 pages.
Office Action received for Japanese Patent Application No. 2014-123100, dated May 18, 2015, 1 page.
Office Action received for Japanese Patent Application No. 2014-143959, dated Dec. 17, 2015, 7 pages.
Office Action received for Japanese Patent Application No. 2014-143959, dated May 1, 2015, 2 pages.
Office Action received for Korean Patent Application No. 10-2009-7003220, dated Oct. 28, 2013, 6 pages.
Office Action received for Korean Patent Application No. 10-2014-7005383, dated May 14, 2014, 6 pages.
Office Action received for Mexican Patent Application No. MX/A/2013/007919, dated Oct. 19, 2015, 2 pages.
Office Action received from Japanese Patent Application No. 2013-556667, dated Jan. 22, 2016, 9 pages.
Shanghai Dongyue Medical Health Product Co., Ltd., "Silicon-Gel Membrane-Scar Bandage", available online at <http://www.shdongyue.com/cp/shaos/shaos02b.asp>, last visited on Nov. 6, 2008, 2 pages.
Smith & Nephew, "CICA-CARE. Silicone Gel Sheeting", available online at <http://wound.smith-nephew.com/za/Product.asp?NodeId=569&Tab=5&Hide=True>, last visited on Jun. 9, 2009, 1 page.
Wound Care Technologies, "DERMAClose™ RC: Continuous External Tissue Expander", available at <http://www.woundcaretech.com/sell-sheet.pdf>, last visited on Sep. 10, 2009, 2008, 2 pages.
Wound Care Technologies, "Instructions for Use. DERMAClose™ RC", available at <http://www.dermaclose.com/instructions.pdf>, last visited on Sep. 10, 2009, 2008, 2 pages.
Aarabi, et al., Aarabi et al., "Mechanical Load Initiates Hypertrophic Scar Formation Through Decreased Cellular Apoptosis", The FASEB Journal, vol. 21, Oct. 2007, pp. 3250-3261.
Al-Attar, et al., Al-Attar et al., "Keloid Pathogenesis and Treatment", Plastic and Reconstructive Surgery, vol. 117, No. 1, Jan. 2006, pp. 286-300.
Angelini, et al., Angelini et al., "Comparative Study of Leg Wound Skin Closure in Coronary Artery Bypass Graft Operations", Thorax, vol. 39, 1984, pp. 942-945.
Artz, et al., Artz et al., "Burns: A Team Approach," (Saunders), Philadelphia, 1979, pp. 24-44.
Atkinson, et al., "A Randomized, Controlled Trial to Determine the Efficacy of Paper Tape in Preventing Hypertrophic Scar Formation in Surgical Incisions that Traverse Langer's Skin Tension Lines", Plastic and Reconstructive Surgery, vol. 116, No. 6, Nov. 2005., pp. 1648-1656.
Bachert, et al., Bachert et al., "Probing Elastic Modulus and Depth of a Two Layer Human Skin Model with Piezoelectric Cantilevers", Biomedical Engineering Senior Design Team, Drexel University, 2003, pp. 1-27.
Barker, , Barker, D.E., "Skin Thickness In the Human," Plast. Reconstr. Surg., vol. 7, 1951, pp. 115-116.
Berman, et al., Berman et al., "Keloid and Hypertrophic Scar", available at http://www.emedicine.com/DERM/topic205.htm> last visited on Nov. 19, 2007, 23 pages.
Bunker, , Bunker, Timothy D., "Problems with the Use of Op-Site Sutureless Skin Closures in Orthopaedic Procedures", Annals of the Royal College of Surgeons of England, vol. 65, 1983, pp. 260-262.
Burd, et al., Burd et al., "Hypertrophic Response and Keloid Diathesis: Two Very Different Forms of Scar", Plastic and Reconstructive Surgery, vol. 116, No. 7, Dec. 2005, pp. 150e-157e.

Chen, et al., Chen et al., "Prospective Study Comparing Wounds Closed with Tape with Sutured Wounds in Colorectal Surgery", Arch.Surg., vol. 136, Jul. 2001, pp. 801-803.
Davison, et al., Davison et al., "Ineffective Treatment of Keloids with Interferon Alpha-2b", Plastic and Reconstructive Surgery, vol. 117, No. 1, Jan. 2006, pp. 247-252.
Escoffier, et al., Escoffier et al., "Age-Related Mechanical Properties of Human Skin: An in Vivo Study", The Journal of Investigate Dermatology, vol. 93, No. 3, Sep. 1989, pp. 353-357.
Evans, et al., Evans et al., "Measuring the Mechanical Properties of Human Skin in vivo Using Digital Image Correlation and Finite Element Modelling", J. Strain Analysis, vol. 44, 2009, pp. 337-345.
Fairclough, et al., Fairclough et al., "The Use of Sterile Adhesive Tape in the Closure of Arthroscopic Puncture Wounds: A Comparison with a Single Layer of Nylon Closure", Annals of the Royal College of Surgeons of England, vol. 69, 1987, pp. 140-141.
Gorney, , Gorney, Mark, "Scar: The Trigger to the Claim", Plastic and Reconstructive Surgery. vol. 117. No. 3, Mar. 2006, pp. 1036-1037.
Gurtner, et al., Gurtner et al., "Improving Cutaneous Scar By Controlling The Mechanical Environment: Large Animal and Phase I Studies," Annals of Surgery, vol. 00, 2011, pp. 1-9.
Hof, et al., Hof et al., "Comparing Silicone Pressure-Sensitive Adhesives to Silicone Gels for Transdermal Drug Delivery", Presented at 33 Annual Meeting and Exposition to the Controlled Release Society, Vienna, Austria, Jul. 22-26, 2006, 7 pages.
Koval, et al., Koval et al., "Tape Blisters Following Hip Surgery. A Prospective Randomized Study of Two Types of Tape", The Journal of Bone and Joint Surgery, vol. 85-A, No. 10, Oct. 2003, pp. 1884-1887.
Kuo, et al., Kuo et al., "Prospective, Randomized, Blinded Study of a New Wound Closure Film Versus Cutaneous Suture for Surgical Wound Closure", Dermatologic Surgery, vol. 32, No. 5, May 2006, pp. 676-681.
Lee, , Lee, Y., "Skin Thickness in Korean Adults," Surg. Radiol. Anal., vol. 24, 2002, pp. 183-189.
Marcellier, et al., Marcellier et al., "Optical Analysis of Displacement and Strain Fields on Human Skin," Skin Res. Technol., vol. 7, 2001, pp. 246-253.
Mustoe, et al., Mustoe et al., "A Randomized, Controlled Trial to Determine the Efficacy of Paper Type in Preventing Hypertrophic Scar Formation in Surgical Incisions that Traverse Langer's Skin Tension Lines", Plastic and Reconstructive Surgery, vol. 116, No. 7, Dec. 2005., pp. 1657-1658.
Nahabedian, , Nahabedian, Maurice Y., "Scar Wars: Optimizing Outcomes with Reduction Mammaplasty", Plastic and Reconstructive Surgery, vol. 116, No. 7, Dec. 2005, pp. 2026-2029.
O'Brien, et al., O'Brien et al., "Silicon Gel Sheeting for Preventing and Treating Hypertrophic and Keloid Scars (Review)", The Cochrane Collection, 2009, pp. 1-47.
Pitcher, , Pitcher, David, "Sutureless Skin Closure for Pacemaker Implantation: Comparison with Subcuticular Suture", Postgraduate Medical Journal, vol. 59, Feb. 1983, pp. 83-85.
Shirado, et al., Shirado et al., "Realization of Human Skin-Like Texture by Emulating Surface Shape Pattern and Elastic Structure", presented at Symposium on Haptic Interfaces for Virtual Environment and Teleoperator Systems 2006, Mar. 25-26, 2006, Alexandria, VA., pp. 295-296.
Staloff, et al., Staloff et al., "Measurement of Skin Stretch Using Digital Image Speckle Correlation," Skin Res. Technol., vol. 14, 2008, pp. 298-303.
Sullivan, et al., Sullivan et al., "Acute Wound Care", Chapter 7 in ACS Surgery: Principles and Practice, 2007, pp. 1-24.
Teot, , Teot, Luc, "Scar Evaluation and Management Recommendations", European Tissue Repair Society, Scar Controll, ETRS-Bulletin 12.1 &2, available online at <http://www.etrs.org/bulletin12_1section11.php>, last visited on Nov. 30, 2007.
Vaughan, et al., Vaughan et al., "Optimal Closure of Surgical Wounds in Forefoot Surgery: Are Adhesive Strips Beneficial?", Acta Orthop. Belg. vol. 72 No. 6, 2006, pp. 731-733.
Vowden, , Vowden, Kathryn, "Wound Management. Policy and Resource Pack", Bradford Teaching Hospitals NHS Foundation Trust, Mar. 2003, pp. 1-72.

(56) References Cited

OTHER PUBLICATIONS

Watson, et al., Watson et al., "Op-Site Skin Closure: A Comparison with Subcuticular and Interrupted Sutures", Annals of the Royal College of Surgeons of England, vol. 65, 1983, pp. 83-84.
Webster, et al., Webster et al., "Closure of Abdominal Wounds by Adhesive Strips: A Clinical Trial", British Medical Journal, vol. 20, Sep. 20, 1975, pp. 696-697.
Westaby, , Westaby, S., "Evaluation of a New Product for Sutureless Skin Closure", Annals of the Royal College of Surgeons of England, vol. 62, 1980, pp. 129-132.
English summary of Office Action for BR Application No. 1120140195870, dated Jul. 20, 2021.

* cited by examiner

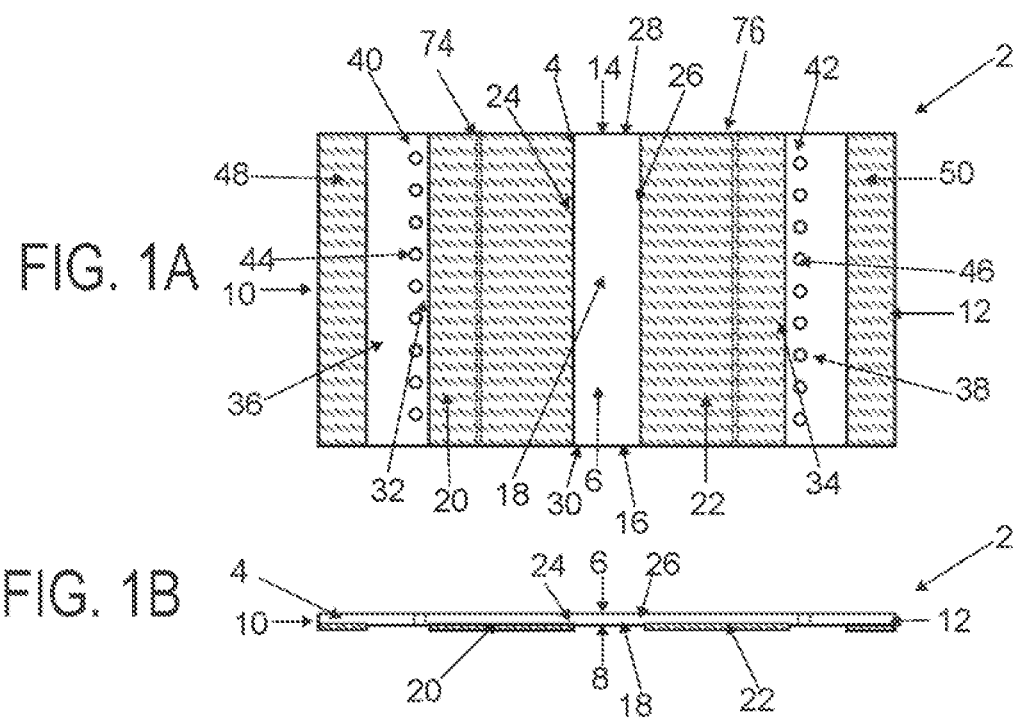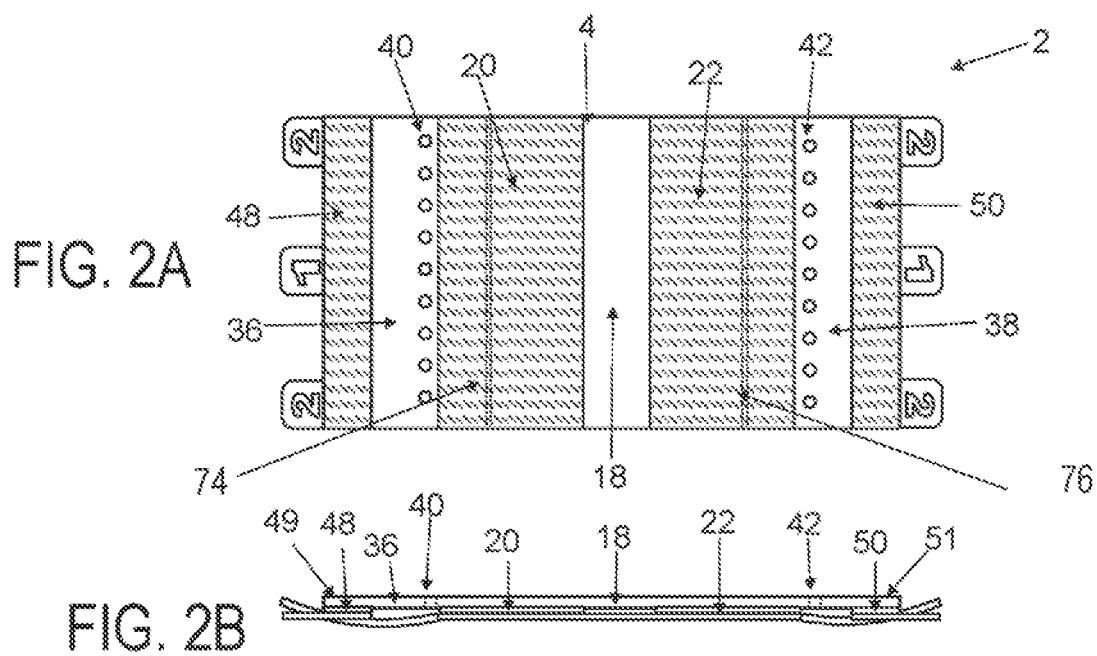

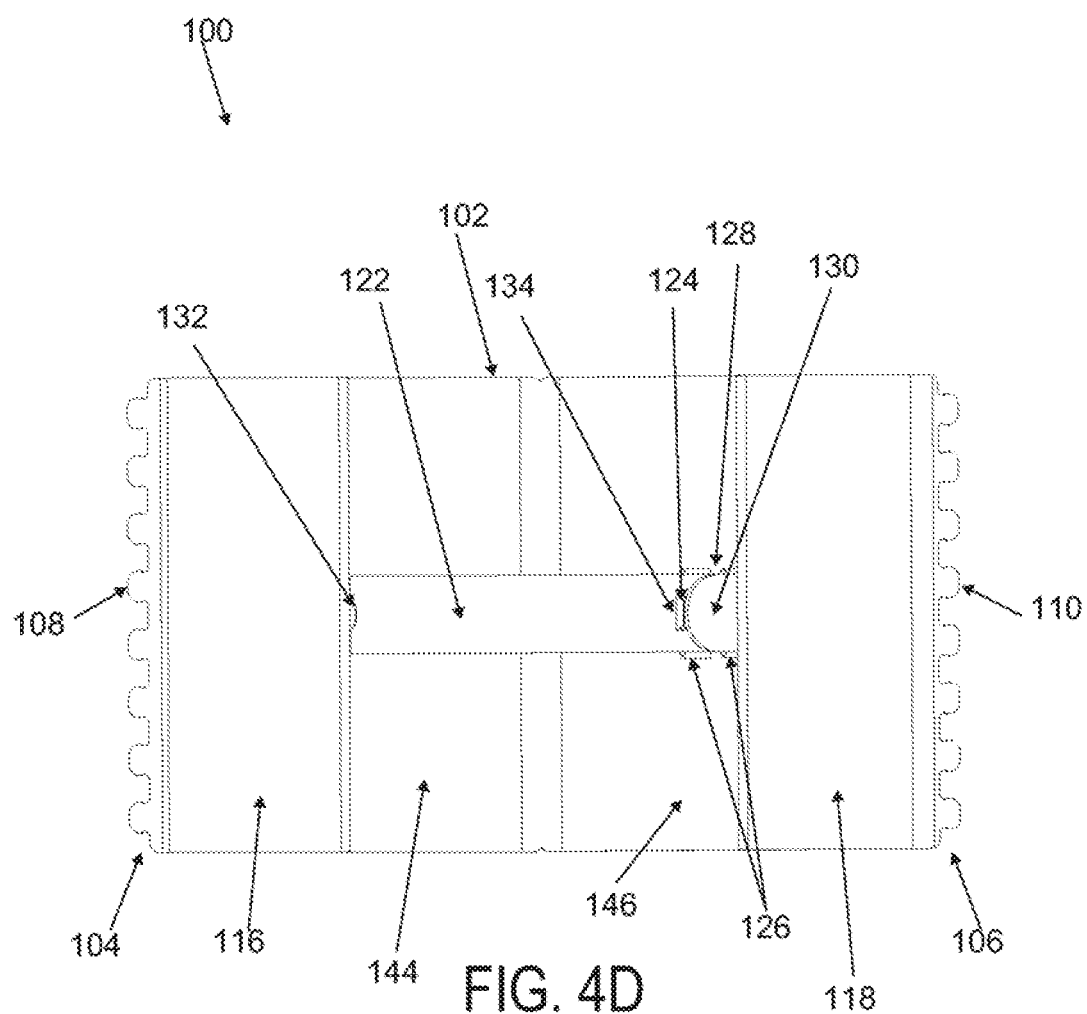

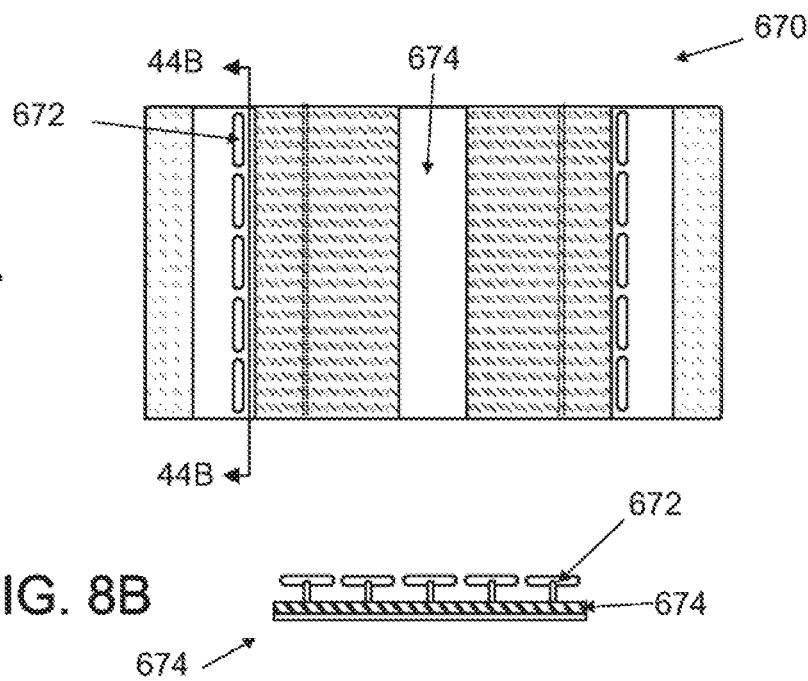
FIG. 8A
FIG. 8B
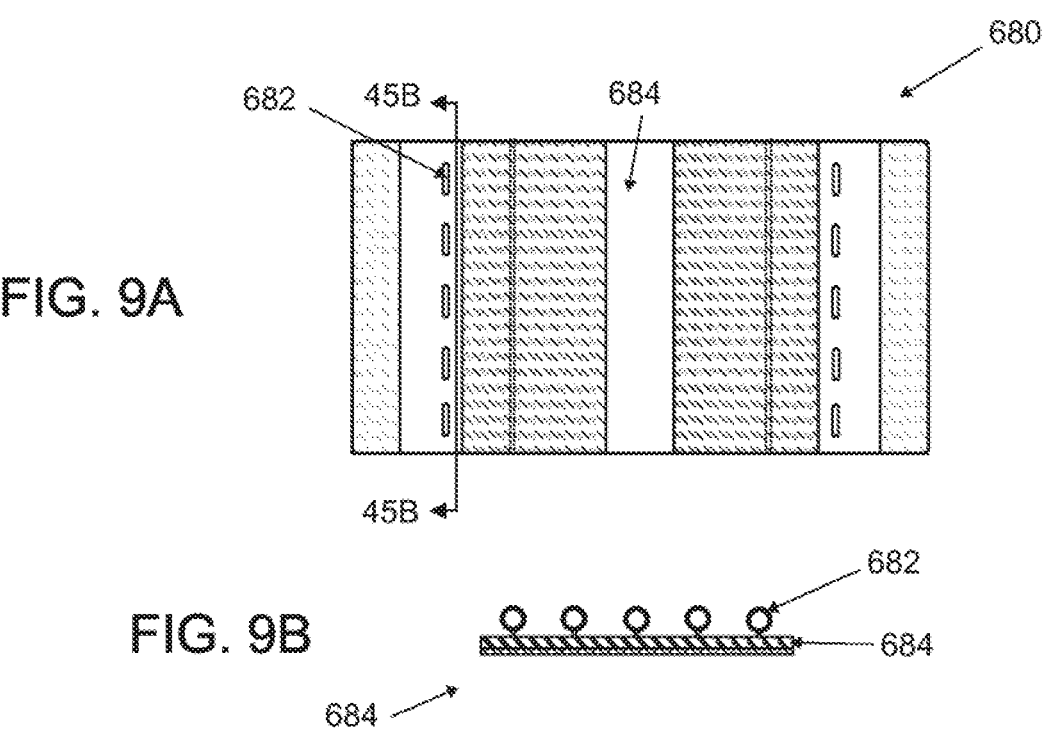
FIG. 9A
FIG. 9B

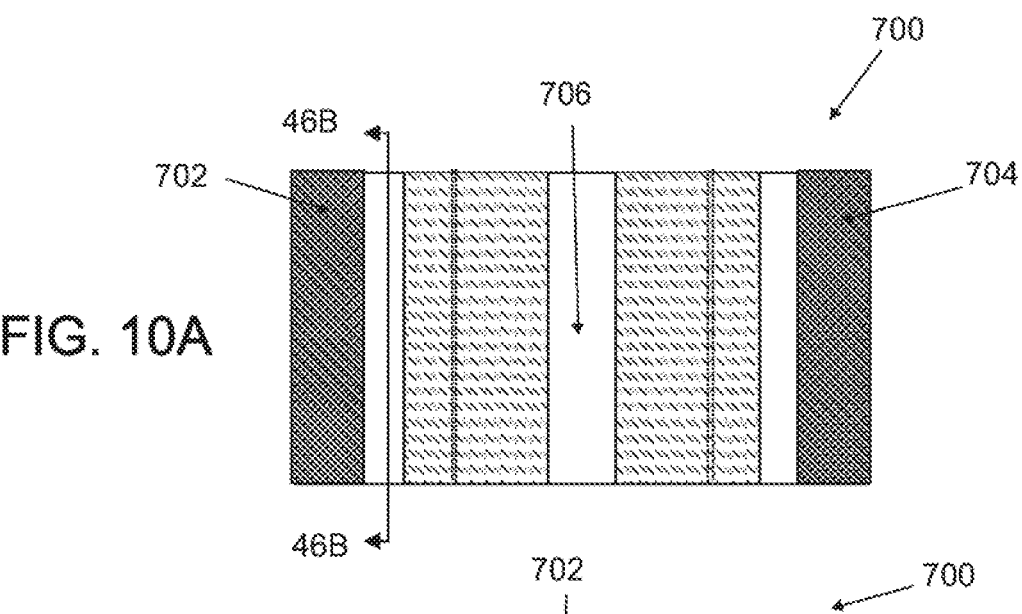
FIG. 10A
FIG. 10B
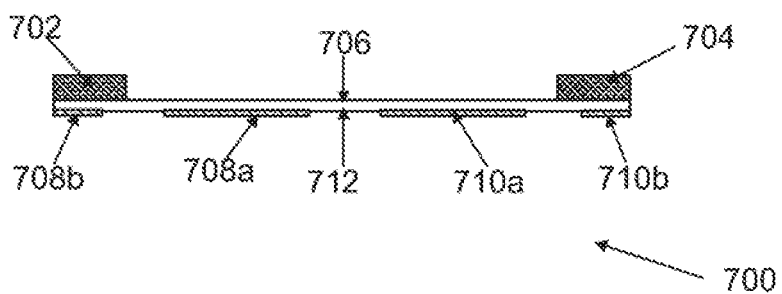
FIG. 10C

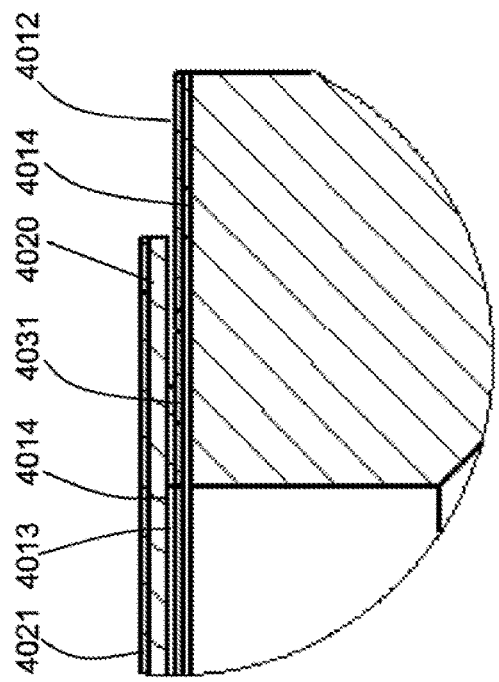
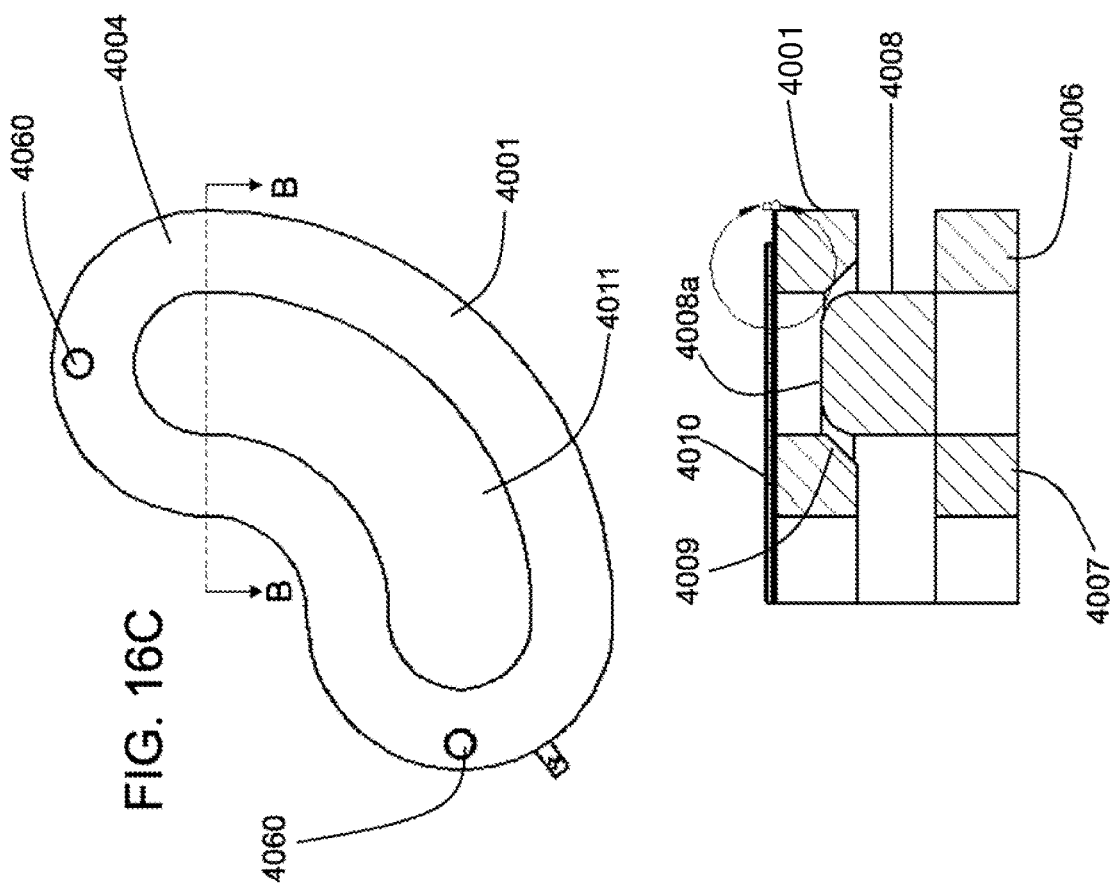

RADIALLY TENSIONED WOUND OR SKIN TREATMENT DEVICES AND METHODS

CROSS-REFERENCE TO RELATED APPLICATIONS

This application is a continuation of U.S. application Ser. No. 13/789,512 filed Mar. 7, 2013, issued as U.S. Pat. No. 10,213,350 on Feb. 26, 2019, which is a continuation of International Application Ser. No. PCT/US13/25449, filed Feb. 8, 2013, which claims benefit to U.S. Provisional Application Ser. No. 61/596,708, filed on Feb. 8, 2012, which are hereby incorporated by reference in their entirety. This application is related to U.S. patent application Ser. No. 12/854,859, filed on Aug. 11, 2010 and U.S. patent application Ser. No. 13/345,524, filed Jan. 6, 2012, which are each hereby incorporated by reference in its entirety.

BACKGROUND

Scar formation in response to cutaneous injury is part of the natural wound healing process. Wound healing is a lengthy and continuous process, although it is typically recognized as occurring in stages. The process begins immediately after injury, with an inflammatory stage. During this stage, which typically lasts from two days to one week (depending on the wound), damaged tissues and foreign matter are removed from the wound. The proliferative stage occurs at a time after the inflammatory stage and is characterized by fibroblast proliferation and collagen and proteoglycan production. It is during the proliferative stage that the extracellular matrix is synthesized in order to provide structural integrity to the wound. The proliferative stage usually lasts about four days to several weeks, depending on the nature of the wound, and it is during this stage when hypertrophic scars usually form. The last stage is called the remodeling stage. During the remodeling stage, the previously constructed and randomly organized matrix is remodeled into an organized structure that is highly cross-linked and aligned to increase mechanical strength.

While the histological features characterizing hypertrophic scars have been well documented, the underlying pathophysiology is not well known. Hypertrophic scars are a side effect of excessive wound healing, and generally result in the overproduction of cells, collagen, and proteoglycans. Typically, these scars are raised and are characterized by the random distribution of tissue bundles. The appearance (i.e., size, shape, and color) of these scars varies depending on the part of the body in which they form, and the underlying ethnicity of the person affected. Hypertrophic scars are very common, and may occur following any full thickness injury to the skin. Recently, it has been shown in U.S. Patent Application Publication 2006/0037091 (U.S. patent application Ser. No. 11/135,992 entitled "Method for Producing Hypertrophic Scarring Animal Model for Identification of Agents for Prevention and Treatment of Human Hypertrophic Scarring," filed May 24, 2005) which is hereby incorporated by reference in its entirety, that mechanical stress may increase hypertrophic scarring in a murine model.

Keloids are typically characterized as tumors consisting of highly hyperplastic masses that occur in the dermis and adjacent subcutaneous tissue in susceptible individuals, most commonly following trauma. Keloids are often more severe than hypertrophic scars, since they tend to invade normal adjacent tissue, while hypertrophic scars tend to remain confined within the original scar border.

BRIEF SUMMARY

Devices, kits and methods described herein may be for treatment of a subject at a skin site including without limitation for wound treatment or the treatment, amelioration, or prevention of scars and/or keloids, by manipulating mechanical or physical properties of skin or by shielding skin from stresses, and/or by controllably stressing or straining the epidermis and layers of dermal tissue at or near a skin site, i.e., at or adjacent a wound or a treatment site of a subject's skin. According to variations, manipulating mechanical or physical properties may thereby modulate tensile or compressive stress at the skin site. The stress at the skin site may be reduced to levels below that experienced by normal skin and tissue. The stress at the skin site may be increased to levels above that experienced by normal skin and tissue. The stress or strain may be applied to surrounding tissue in one, two, or more directions to manipulate endogenous or exogenous stress at the skin site in one, two or more directions. According to variations, devices and methods described herein may reduce or otherwise manipulate the stress experienced by skin and/or a wound and surrounding tissues in order to treat a subject. The devices may also assist in preventing or reducing the incidence of wound dehiscence.

According to the devices, kits and methods described herein, a skin treatment device, skin device, wound treatment device, scar or keloid treatment device, scar or keloid amelioration or prevention device, bandage, or dressing may be provided that may be applied, attached to or coupled to one or more layers of the skin or tissue of a subject (hereinafter referred to as "dressing", "skin device" or "skin treatment device").

In addition to amelioration of scar formation, other uses for such skin treatment device may or may not include without limitation, for example, treating skin related conditions such as acne, blemishes, rosacea, warts, rashes (including but not limited to erythematous, macular, papular and/or bullous conditions), psoriasis, skin irritation/sensitivity, allodynia, telangiectasia, port wine stains and other arteriovenous malformations, and ectopic dermatitis; treating or improving existing scars, wrinkles, stretch marks, loose or sagging skin or other skin irregularities; lifting, pinning, holding, moving skin for various purposes such as during pre-operative preparation, during surgical procedures for example as a low-profile tissue retractor, to stabilize blood vessels during needle or catheter insertion, postoperatively, pre or post operatively for pre-treating or preconditioning skin for example, prior to scar revision, wound incision, body contouring, in mastectomy skin expansion, aesthetic skin treatment or resurfacing whether topical or subdermal, whether or not using an energy modality such as, for example, microwave, radio-frequency ablation, high-intensity focused ultrasound, laser, Infrared, incoherent light, during weight loss, or for aesthetic purposes; hair removal or hair loss; treating and/or closing skin injuries for example, incisions, wounds, chronic wounds, bed sores, ulcers (including venous stasis ulcers), preventing or reducing the incidence of wound dehiscence, diabetic skin or wound conditions, burn healing and/or relief; acting as an occlusive or negative-pressure wound dressing; protecting incisions or wounds, e.g. prevention of splitting or opening, protecting newborn belly buttons after cutting umbilical cord. Such treatments may also be used to treat skin grafts (including split-thickness and full-thickness grafts, xenografts, cadaveric graft, autologous grafts), skin flaps and skin substitutes, with or without the use of biomaterials or biodressings, either on top and/or below the graft/flap/substitute, or otherwise in the treatment site. Examples of such materials may include ALLODERM® (LifeCell Corp., Branchburg, N.J.), OASIS® (Healthpoint Ltd., Fort Worth, Tex.), INTEGRA® Dermal Regeneration Template (Integra Life Sciences Holding Co., South Plainfield, N.J.), BIOBRANE® and BIO-BRANE-L (Bertek Pharmaceuticals, Sugarland Tex.), APLIGRAF® (Organogenesis Inc., Canton, Mass.), EPICEL® (Genzyme Biosurgery, Cambridge, Mass.), CELADERM™ (Celadon Science LLC, Hyattsville, Md.), TRANSCYTE® and DERMAGRAFT® (Advanced BioHealing Inc., Westport, Conn.), EZ (Brennan Medical Inc., St. Paul, Min.), LASERSKIN® (Fidia Advanced Biopolymers, Italy), ORCEL® (FortiCell Bioscience Inc., Englewood Cliffs, N.J.), and the like. Such treatments may include use of a drug or other therapeutic agent that may be applied to the skin with such device. The agents may include but are not limited to antibiotics, anti-fungals, immune modulators including corticosteroids and non-steroidal immune modulators. The agents may be provided in any of a variety of formulations, including but not limited powders, gels, lotions, creams, pastes, suspensions, etc. The devices may also be used for purposes of delivering a drug to the skin or through the skin, for example by stretching the skin and applying a drug thereto. Different configurations of the device may be amenable to the size or geometry of different body regions. The treatments may be applied to regions of any shape (e.g. linear, curved, stellate), size or depth, and to one or more regions of the body, including but not limited to the scalp, forehead, face e.g. nose, eyelid, cheeks, lips, chin), ears, neck, shoulder, upper arm, lower arm, palm, dorsum of the hand, fingers, nailbed, axilla, chest, nipple, areola, back, abdomen, inguinal region, buttocks, perineal region, labia, penis, scrotum, thigh, lower leg, plantar surface of the foot, dorsal surface of the foot, and/or toes. Such devices may also be referred to herein as a "dressing", "skin device" or "skin treatment device".

In some situations, an immediate, quick or simple application of a dressing may be desired. Devices, kits and methods described herein may be for the preparation and/or application of a dressing to the skin and the separation of the applicator, tensioning device or dressing carrier, support or base from the skin device.

The devices, kits or methods described herein may include a carrier, support, base, applicator or tensioning device, each of which may: contain, hold, carry or support a dressing at least temporarily; may be used to prepare a dressing for application; may be used to deliver, orient or apply a dressing; may be used to maintain a dressing in a stressed or strained configuration; may be used to stress or strain a dressing; may be used to separate the dressing from the carrier, support, base, applicator or tensioning device and/or may be used during or after application of a dressing to provide additional treatment to a wound, incision or other treatment location; and/or may be used to apply pressure to a wound, incision or other treatment location. According to some variations, an applicator may provide structural support for a dressing while or after an adhesive liner is released. According to some variations, the assembly may be constructed to avoid folding or bending of the dressing to the extent that the adhesive on the dressing sticks to itself. For example, when some variations of the dressing are held or supported at one point or along one edge of the dressing in a cantilever configuration, the dressings will not bow, laterally deform, or otherwise deform out of plane, under their own mass or configuration.

Devices, kits and methods described herein may be for the treatment, amelioration, or prevention of scars and/or keloids by creating and/or maintaining a pre-determined strain in an elastic skin treatment device that is then affixed to the skin surface using skin adhesives to transfer a generally planar (e.g. compressive) force from the bandage to the skin surface.

In some variations, a dressing is provided, comprising an elastic sheet structure (e.g., a comprising a silicone polyurethane, TPE (thermoplastic elastomers), synthetic rubber or co-polyester material) comprising an upper surface, a lower surface, a first edge and a second edge opposite the first edge, and one or more adhesive regions. The dressing may further comprise a first release liner releasably attached to the adhesive region or regions. The adhesive region(s) may comprise a pressure sensitive adhesive. The dressing may be tapered or otherwise shaped to reduce skin tension at the edges. The dressing may have modified, reduced or no adhesive near its edges to reduce skin tension at the edges. Portions of the dressing may be unstrained and may thereby reduce strain in certain areas of the skin Where the dressing is applied. In some specific examples, the unstrained area or areas are found between the edges of the dressing and the strained area(s). In some further examples, the unstrained areas are limited to this area and are not found, during application or use, between the strained areas of a single dressing, in use. In still further examples, the unstrained areas are limited to areas along the edges of a dressing that intersect the strain axis of the strained area(s), but not to areas along the edges of the dressing that are generally parallel to the strain axis.

A dressing carrier, dressing support, dressing base, applicator and/or tensioning device may be provided. The dressing carrier, dressing support, dressing base, applicator and/or tensioning device may be configured to stress and/or strain a dressing prior to application to a subject. A device may be used to strain and/or maintain a strain on a dressing. The device may further comprise a releasable locking mechanism, attachment mechanism or adhesive, configured to maintain the member or mechanism in a strained configuration.

In some situations, application of a compressive force to a wound is desirable to reduce bleeding. According to some variations, the carrier, support, base, applicator or tensioning device described herein may be further used to help reduce bleeding, e.g., by allowing application of a compressive force using the device while or after the dressing is applied. A coagulative additive may also be provided on a dressing.

According to some variations, a dressing assembly comprises: a base structure having an inner surface; a cover structure having an opposing surface, wherein the base structure is movably coupled to the cover structure; and a dressing comprising a first surface configured to be applied to a wound or skin of a subject, and a back surface, wherein at least a portion of the back surface is removably coupled to the inner surface of the base structure; and wherein the cover structure is configured to move from a first position where the opposing surface interfaces with and is substantially parallel to the first surface to the dressing to a second position where the opposing surface is separated from the first surface of the dressing. According to variations, the first surface of the dressing comprises an adhesive region. According to variations the first surface of the dressing comprises an adhesive backing interfacing an adhesive region on the dressing. According to variations, the opposing surface of the cover structure comprises an adhesive backing covering the adhesive region when the cover structure is in the first position and separated from the adhesive region when the cover structure is in the second position. According to variations, the dressing comprises an elastic material. According to variations, the dressing comprises a first attachment region coupled to the inner surface of the base structure and a second attachment region coupled to the opposing surface of the cover structure, wherein the cover and base are configured to exert a straining force to strain the dressing when the cover is moved from the first position to the second position. According to variations, a tensioning structure is configured to exert the straining force on the dressing. According to variations, the tensioning structure comprises: a first structure configured to couple the dressing at the first attachment region to the inner surface of the base structure; and a second structure configured to couple the dressing at the second attachment region to the opposing surface of the cover; wherein the tensioning structure is configured to exert the straining force to the dressing between the first attachment region and the second attachment region when the cover structure is moved with respect to the base structure from the first position to the second position. According to some variations, the dressing has a first width when the cover is in the first position and a second width or radius when the cover is in the second position, wherein the second width or radius is greater than the first width or radius. According to variations, the second width or radius is at least 20% greater than the first width or radius. According to variations, the second width or radius is at least 40% great than the first width or radius. According to variations, the base structure comprise at least one relatively rigid element and at least one relatively flexible element, wherein the relatively rigid element is sufficiently rigid to support the dressing when the straining force is applied in a first direction; and wherein the relatively flexible element permits the base structure to flex in a second direction. According to variations, the at least one relatively rigid element comprises a plurality of flexible coupled, relatively rigid elements. According to variations, the cover structure comprises at least one relatively rigid element and at least one relatively flexible element. According to variations, a release device is configured to release the dressing from the base structure after the dressing is applied to a wound or skin of a subject. According to some variations, base structure is pivotably coupled to the cover structure.

Described herein is a dressing system that may comprise a dressing comprising a first edge and a second edge, where the second edge may have an orientation that is non-parallel and non-orthogonal to the first edge when the dressing is in an unstrained state, and a first face comprising an adhesive, and a frame removably attached to the dressing and supporting the first edge and the second edge of the dressing, the frame comprising an outer edge, an inner edge, and an opening surrounded by the inner edge. In some variations, the frame may be coupled to a second face of the dressing opposite of the first face. The dressing may comprise a circular or oval dressing. In some variations, the dressing may comprise a release region configured to separate the dressing from the frame. In some variations, the release region may comprise at least one of a scored region, a perforated region, or comprises an embedded pull line. Additionally or alternatively, the release region may comprise a pull tab coupled to the release region. The first edge of the dressing may comprise an arcuate edge with a first radius of curvature. In some variations, the second edge of the dressing may comprise an arcuate edge with a second radius of curvature. The second radius of curvature may be different from the first radius of curvature.

A dressing system may further comprise a straining structure configured to be pushed through the opening of the frame and to strain the dressing. The frame may be configured to be adhered to the straining structure. In some variations, the frame forms a mechanical interfit with the base. In some variations, the straining structure may comprise a base and raised protrusion. The raised protrusion may comprise a side wall that is orthogonal to the base. In some variations, the raised protrusion may comprise a side wall that forms an open angle with the base that is greater than 90 degrees, while in other variations, the raised protrusion may comprise a side wall that forms an open angle with the base that is less than 90 degrees. The straining structure may comprise a distal face configured to push against the second face of the dressing. The distal face of the straining structure may comprise a general shape that is similar to at least one of the dressing, the opening of the frame, the base or the shape of the side wall at an intersection with the base.

The straining structure and the frame may be configured to apply a generally apply uniform straining forces to the dressing that are orthogonal to the first and second edges of the dressing.

In some variations, the straining structure and the frame may be configured to apply a first straining force to the dressing that is orthogonal to the first edge of the dressing and a second straining force to the dressing that is orthogonal to the second edge of the dressing, the second straining force of the dressing is higher than straining force to the dressing that is orthogonal to a third and fourth edge of the dressing that are located to each side of the second edge.

Any of the dressing systems described herein may further comprise a cutting structure configured to cut the dressing from the frame.

Another variation of a dressing system may comprise a dressing with an unstrained circular or oval shape and a strained circular or oval shape wherein the strain on a first transverse dimension is the same as the strain on a second transverse dimension that is not aligned, parallel or orthogonal to the first transverse dimension.

Another variation of a dressing system may comprise a straining structure, a dressing and a frame configured to releasably retain an elastic dressing, where the straining structure and the frame may be configured to apply a first straining force to the dressing that is orthogonal to the first edge of the dressing and a second straining force to the dressing that is orthogonal to the second edge of the dressing, and where the second straining force of the dressing may be higher than straining force to the dressing that is orthogonal to a third and fourth edge of the dressing that are located to each side of the second edge.

Also described herein are methods of straining a dressing. One variation of a method of straining a dressing may comprise straining a first dressing region along a first axis located in a first plane, straining a second dressing region along a second axis located in a second plane different from the first plane, wherein the second dressing is coupled to the first dressing region, applying the first dressing region to a treatment site, and releasing at least some strain from the first dressing region. Some methods of straining a dressing may further comprise separating a third dressing region from the second dressing region to relieve at least some strain the first dressing region. Optionally, the second dressing region may enclose the first dressing region. Optionally, the third dressing region may enclose the second dressing region. In some methods, releasing at least some strain in the first dressing region may release substantially all of the strain in the second dressing region Another method of straining a dressing may comprise straining a dressing with a uniform set of strain forces, where a first force with an orientation that is orthogonal to a first edge of the dressing and a second force that is orthogonal to a second edge and equal to the first force and has an orientation that is non-aligned, non-parallel and non-orthogonal to the first edge, applying the strained dressing to a treatment site, and relieving the strain in the dressing to apply a compressive force to the treatment site. The dressing may be a circular or oval dressing.

BRIEF DESCRIPTION OF THE DRAWINGS

FIG. 1A is a schematic superior view of one variation of a wound treatment device;

FIG. 1B is a schematic side elevational view of the wound treatment device in FIG. 1A;

FIGS. 2A and 2B are schematic superior and side elevational views of the wound treatment in FIGS. 1A and 1B, respectively, with release liners.

FIGS. 4A to 4D are perspective, side elevational, superior and inferior views of the applicator in FIGS. 3A to 3D in a locked configuration;

FIGS. 8A and 8B are superior and cross sectional views of another dressing comprising T-tag attachment structures.

FIGS. 9A and 9B are superior and cross sectional views of another dressing comprising eyelet attachment structures.

FIGS. 10A to 10C are superior, cross sectional and side elevational views of another dressing comprising a hook-and-loop type of attachment structure.

FIG. 16C is a plan view of an open side of the frame of FIG. 16A coupled to the dressing assembly of FIG. 16A from the open side of the device.

FIG. 16D is a close-up cross-sectional view of a strain plunger of the tensioning device and an assembled dressing assembly and frame of FIG. 16C just prior to straining.

FIG. 16E is a detailed view of section B of FIG. 16D.

DETAILED DESCRIPTION

Figure 2C:
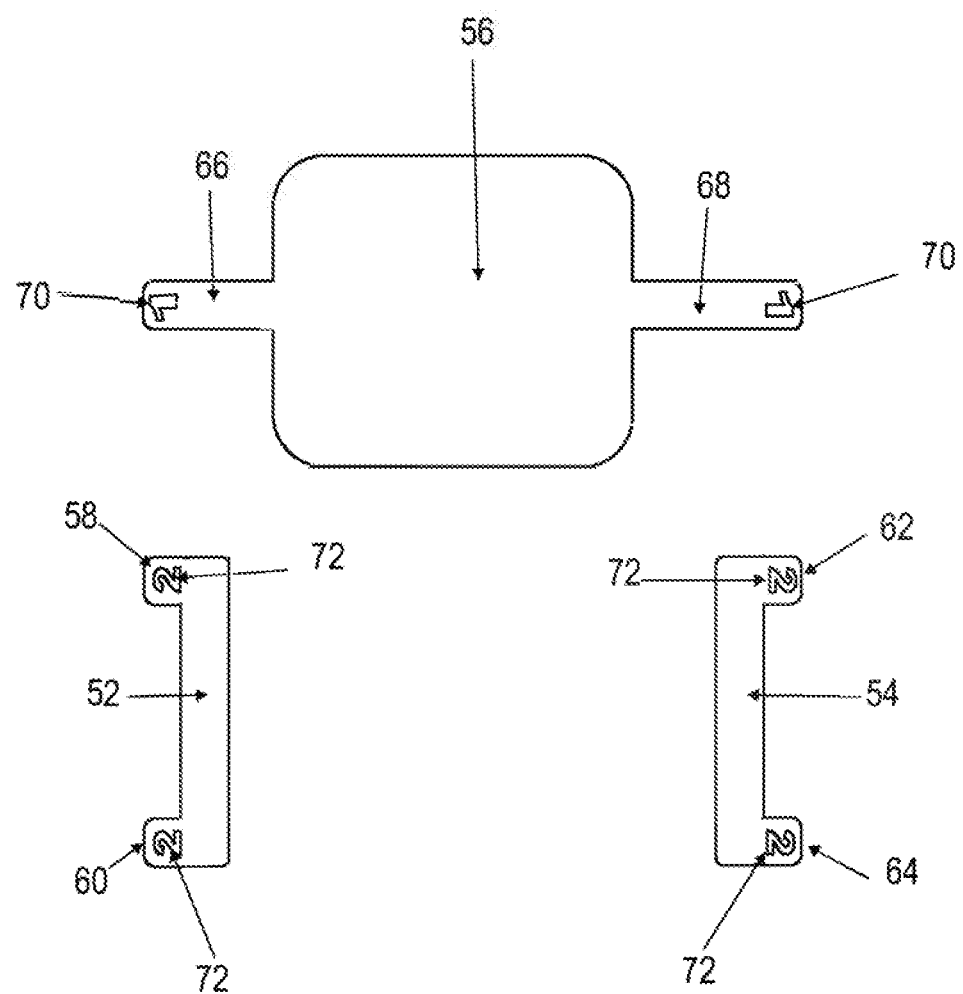
FIG. 2C is a superior component view of the release liners in FIGS. 2A and 2B.
Figure 3A:
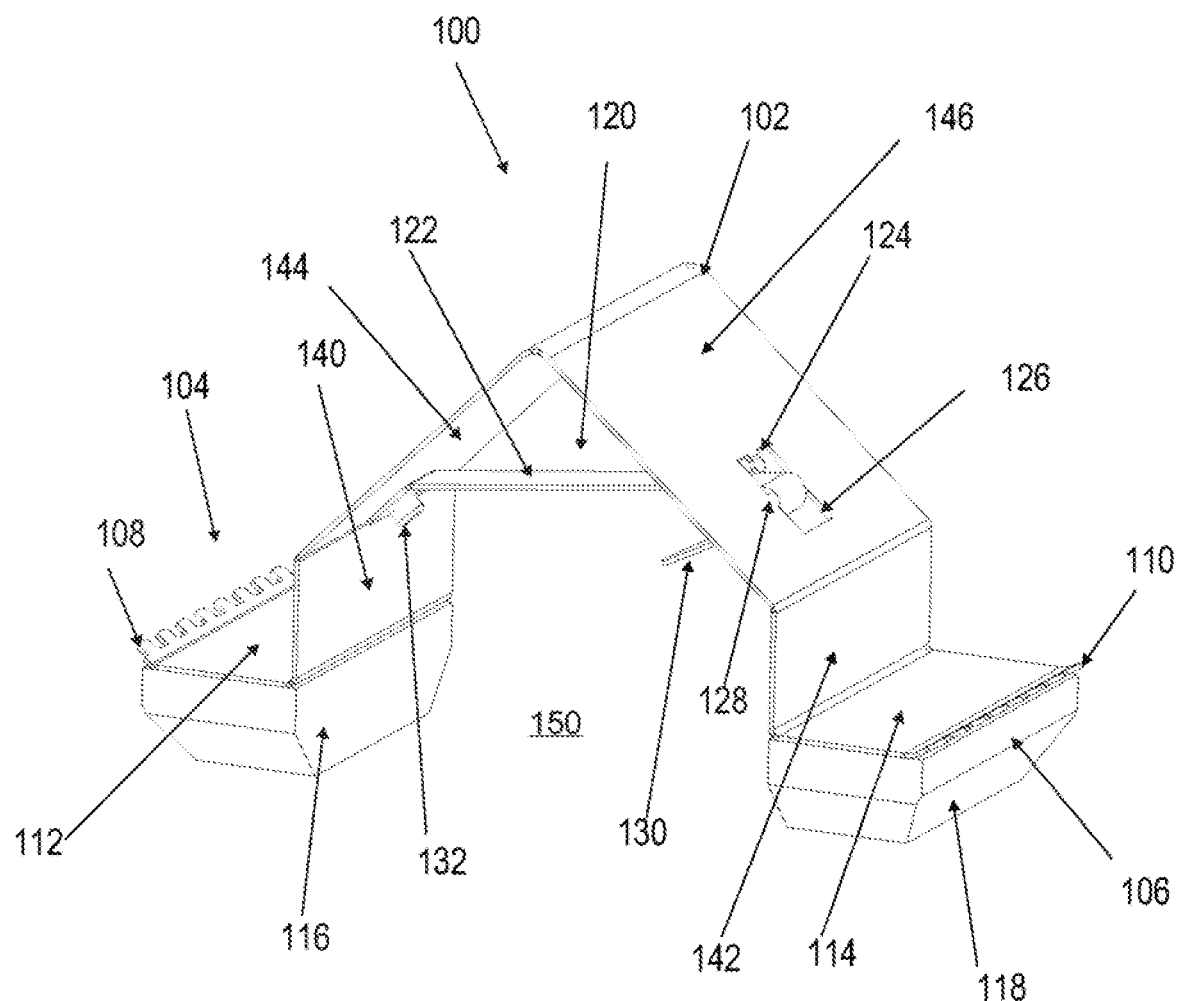
FIG. 3A is a perspective view of a wound treatment applicator in a base configuration.
Figure 3B:
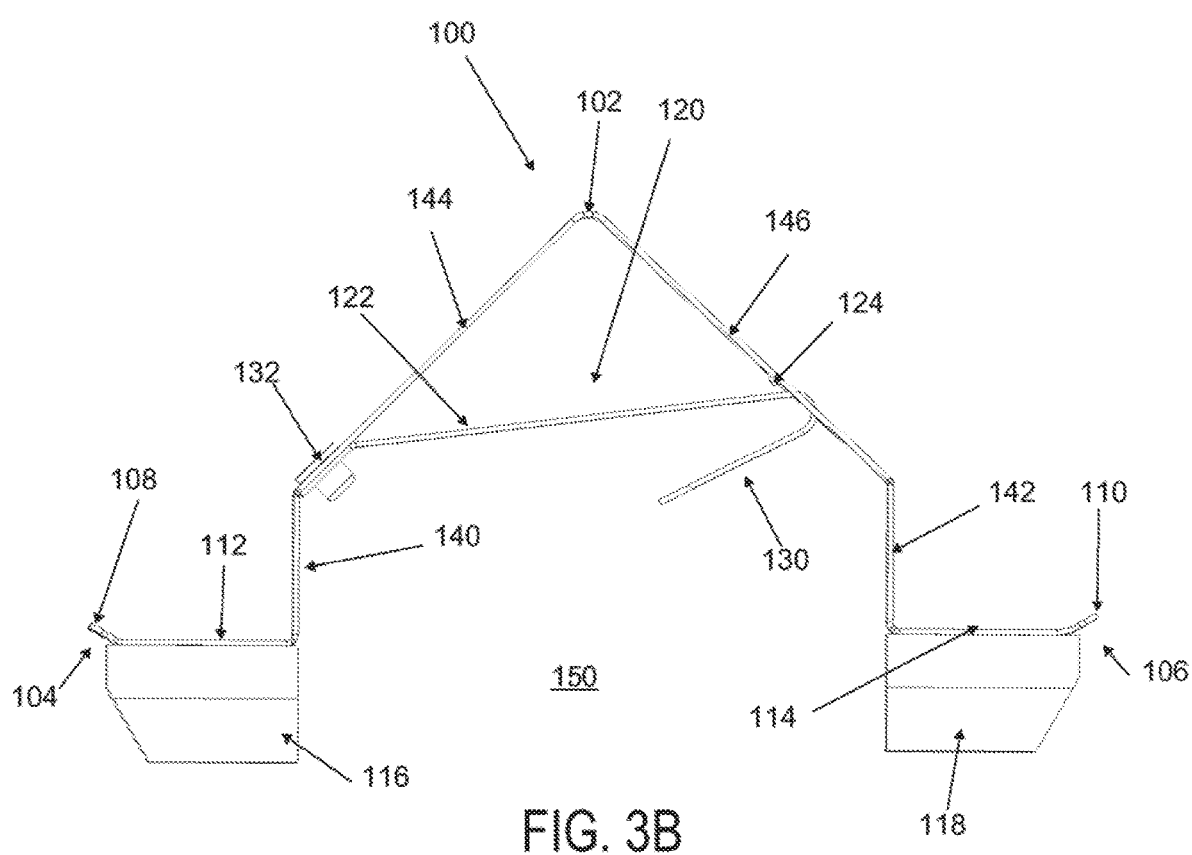
FIGS. 3B to 3D are side elevational, superior and inferior views of the applicator in FIG. 3A.
Figure 3C:
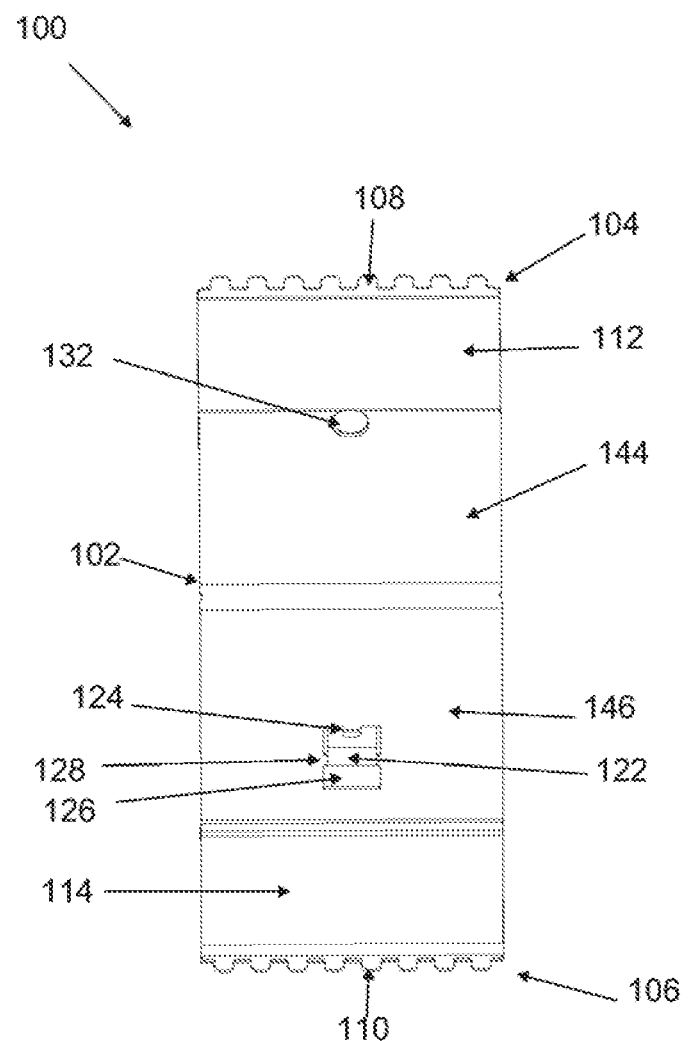
Figure 3D:
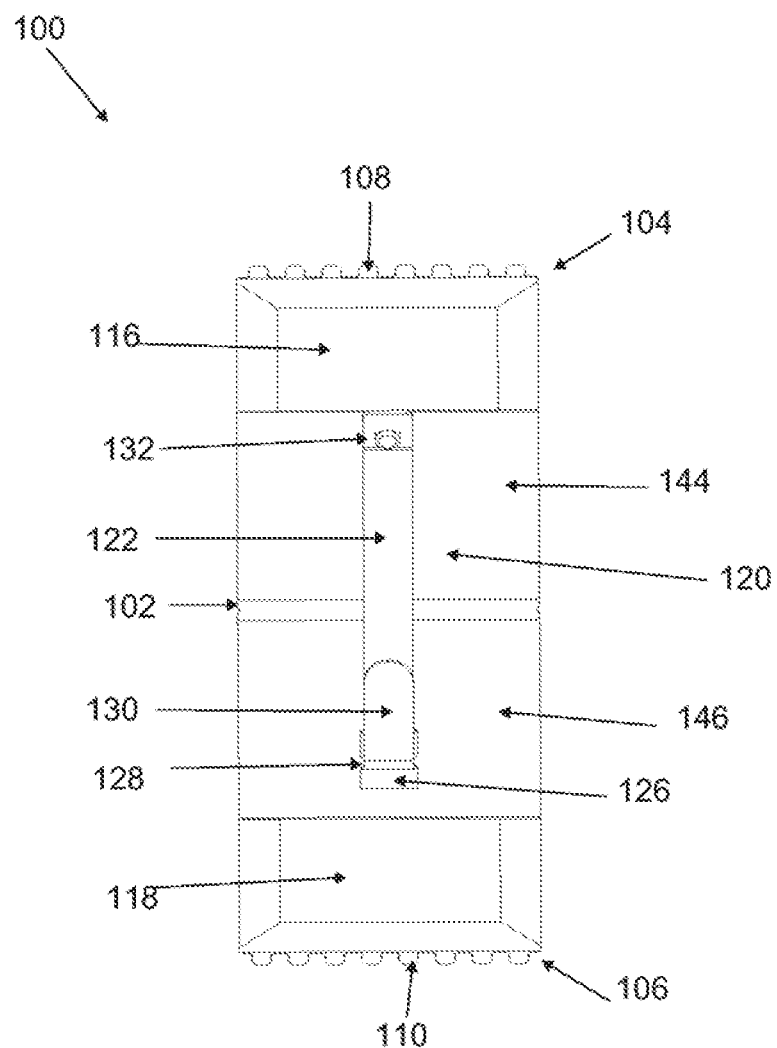
Figure 4A:
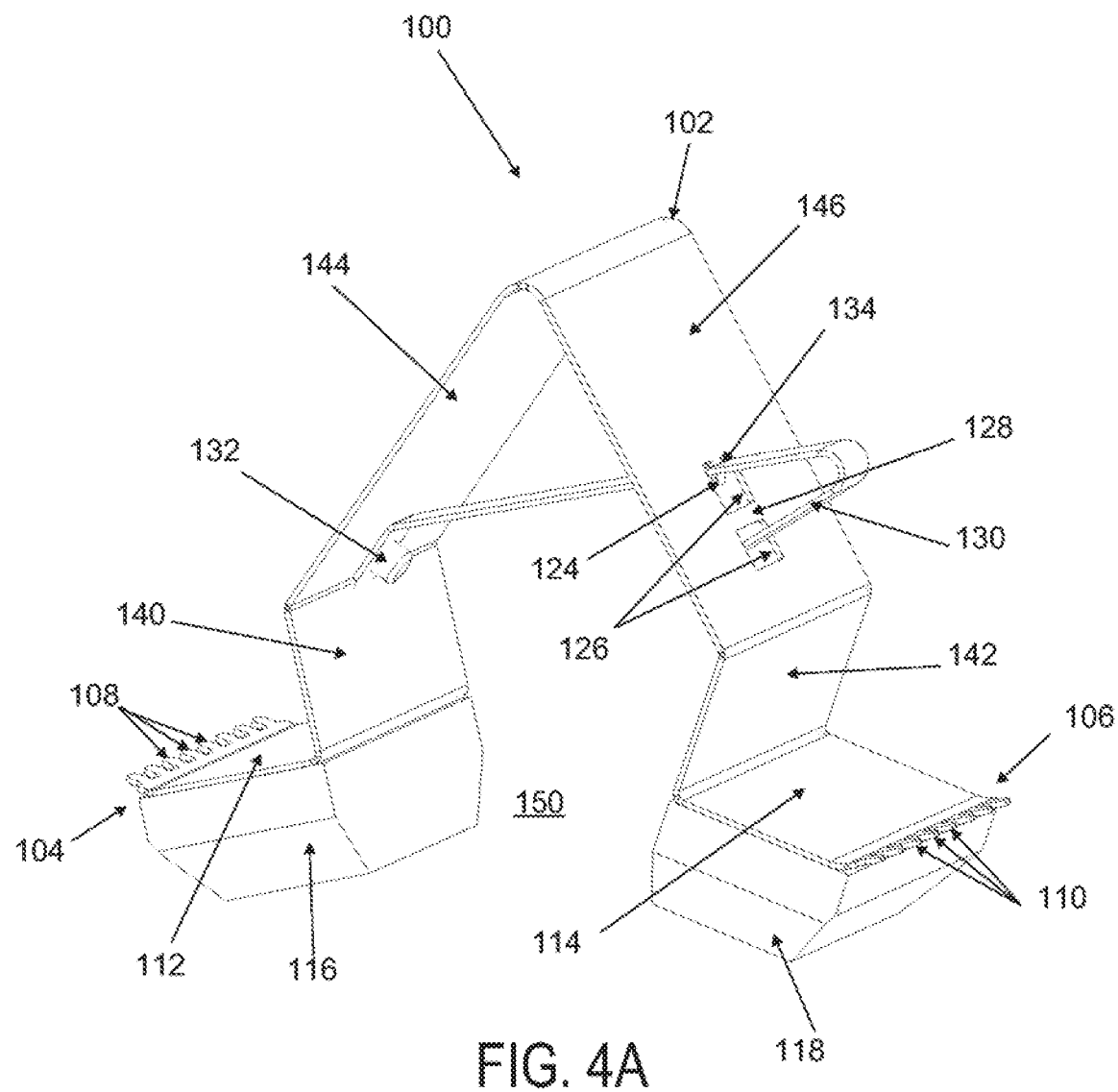
Figure 4B:
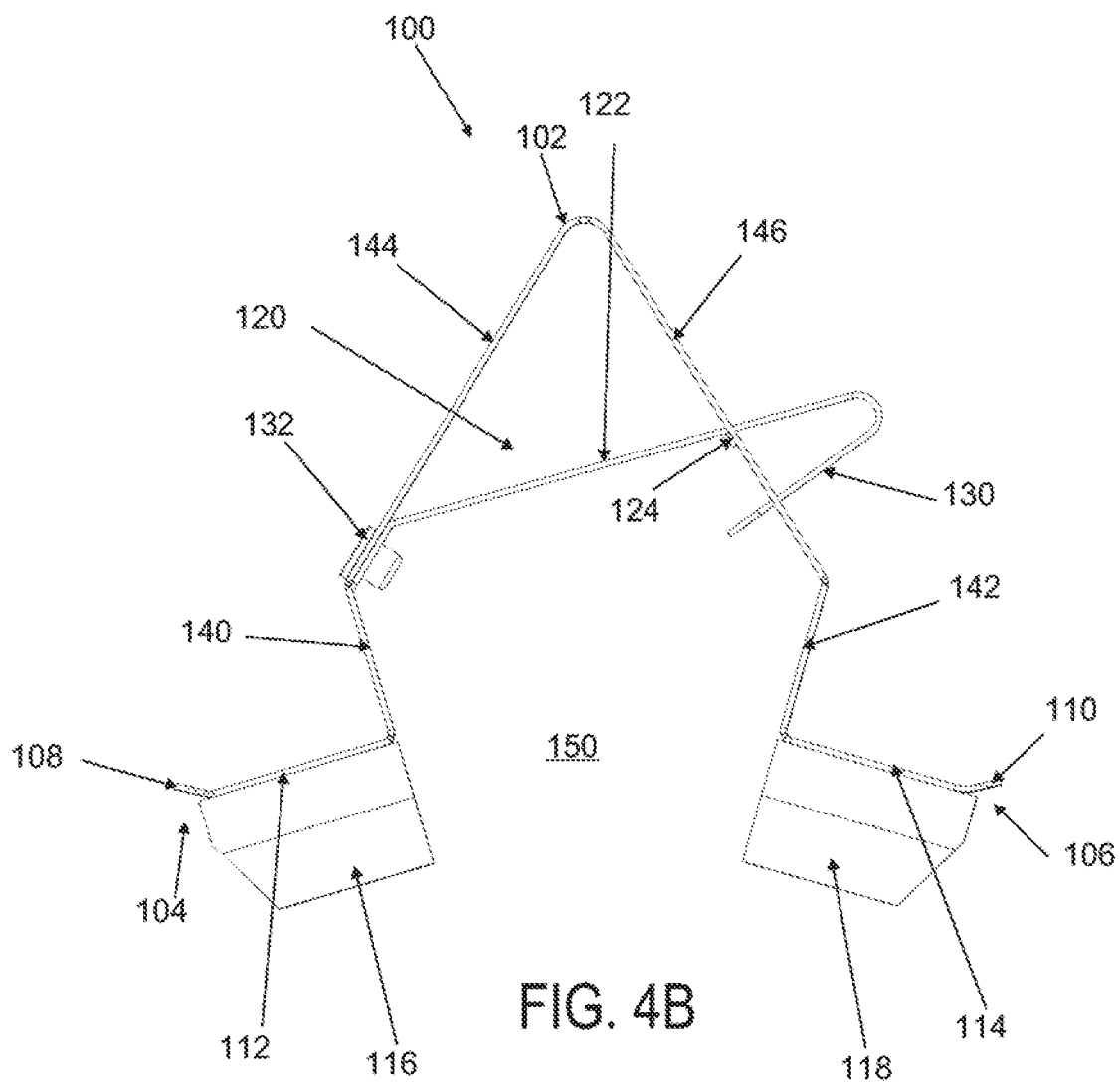
Figure 4C:
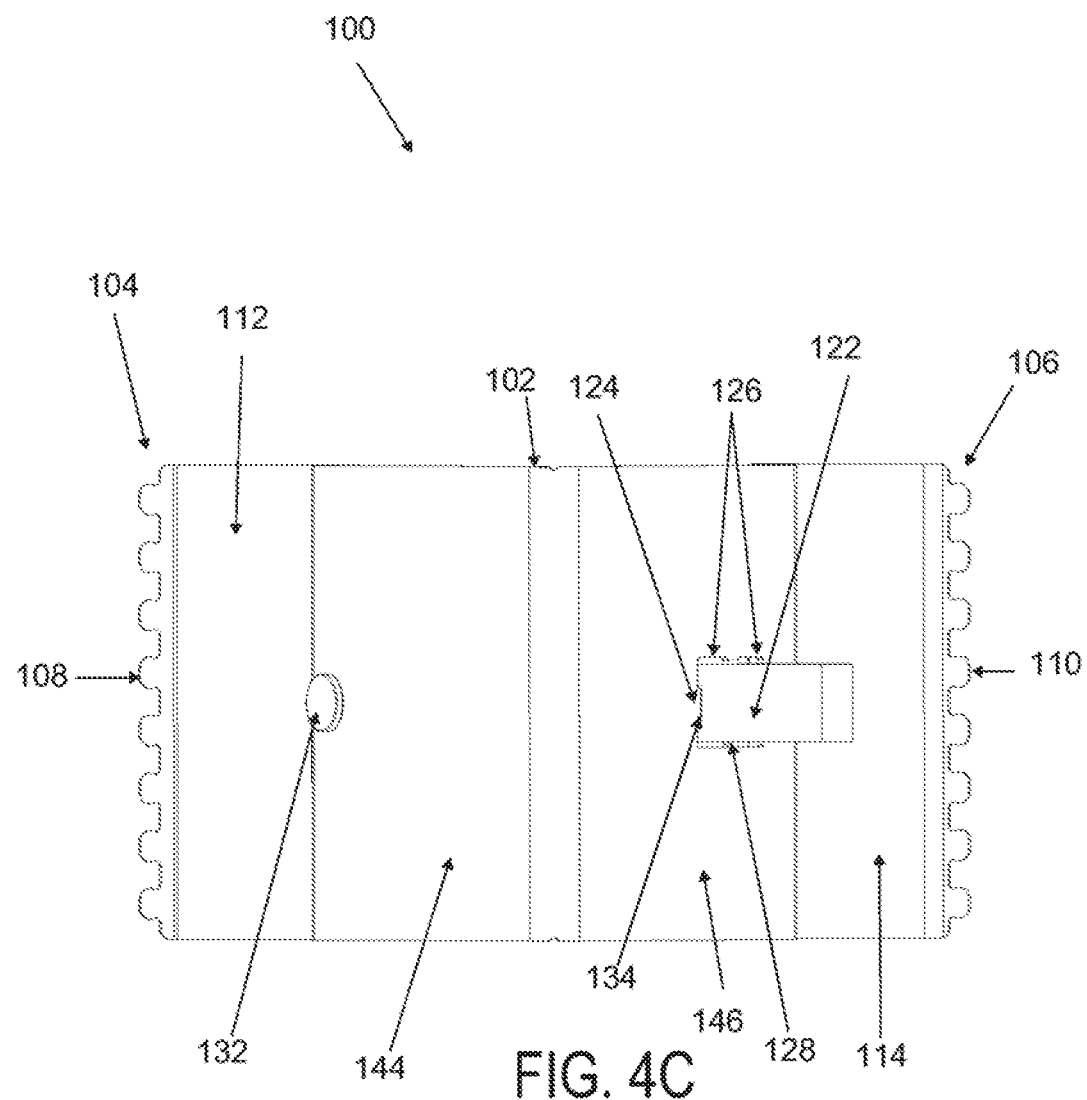

Previous attempts to treat scars and keloids have included surgery, silicone dressings, steroids, x-ray irradiation, and cryotherapy. Each of these techniques has disadvantages. Perhaps the biggest disadvantage is that none of them effectively prevent or ameliorate the formation of scars or keloids in the first instance. That is, these techniques have primarily been used to treat scars after they are already well established.

Unloading of exogenous and/or endogenous stress in the vicinity of the wound may ameliorate the formation of scars, hypertrophic scars, or keloids. The mechanical environment of an injury may be an important factor in tissue response to that injury. The mechanical environment includes exogenous stress (i.e., physiological stress which includes stress transferred to the wound via muscle action or physical body movement) and endogenous stress (i.e., dermal stress originating from the physical properties of the skin itself, including stress induced at the wound site due to swelling or contraction of the skin). The devices, dressings, kits and methods described herein may control or regulate the mechanical environment of a skin including but not limited to the mechanical environment of a wound. The devices, dressings, kits and methods described herein may also control or regulate the mechanical environment to ameliorate scar and/or keloid formation. The mechanical environment of skin may include stress, strain, or any combination of stress and strain. The control of a wound's mechanical environment may be active or passive, dynamic (e.g., by applying an oscillating stress) or static. The stresses and strains acting on the wound may involve the layers of the skin, such as the outer stratum cornewn, the epidermis and dermis, as well as the underlying connective tissue layers, such as the subcutaneous fat. Devices and methods described here may shield a wound from its mechanical environment. The term "shield" is meant to encompass the unloading of stress experienced by the wound as well as providing a physical barrier against contact, contaminants, and the like. The devices and methods described here may shield a wound by unloading the wound and surrounding tissues from endogenous stress and/or exogenous stress. Thus, devices and methods described here may reduce the stress experienced by a wound and surrounding tissues to a lower level than that experienced by normal skin and tissue. Unloading of exogenous and/or endogenous stress in the vicinity of the wound may ameliorate the formation of scars, hypertrophic scars, or keloids.

A cell's external mechanical environment may trigger biological responses inside the cells and change cell behavior. Cells can sense and respond to changes in their mechanical environment using integrin, an integral membrane protein in the plasma membrane of cells, and intracellular pathways. The intracellular pathways are initiated by receptors attached to cell membranes and the cell membrane that can sense mechanical forces. For example, mechanical forces can induce secretion of cytokines, chemokines, growth factors, and other biologically active compounds that can increase or trigger the inflammatory response. Such secretions can act in the cells that secrete them (intracrine), on the cells that secrete them (autocrine), on cells surrounding the cells that secrete them (paracrine), or act at a distance from the point of secretion (endocrine). Intracrine interference can alter cell signaling, which can in turn alter cell behavior and biology including the recruitment of cells to the wound, proliferation of cells at the wound, and cell death in the wound. In addition, the extracellular matrix may be affected.

As noted above, the wound healing process may be characterized in three stages: early inflammatory phase, the proliferative phase, and remodeling. The inflammatory phase occurs immediately after injury and typically lasts about two days to one week. Blood clotting takes place to halt blood loss and factors are released to attract cells that can remove debris, bacteria and damaged tissue from the wound. In addition, factors are released to initiate the proliferative phase of wound healing. In the proliferative phase, which lasts about four days to several weeks, fibroblasts grow and build a new extracellular matrix by secreting collagen and proteoglycans. At the end of the proliferative phase, fibroblasts can act to contract the wound further. In the remodeling phase, randomly oriented collagen is organized and crosslinked along skin tension lines. Cells that are no longer needed can undergo apoptosis. The remodeling phase may continue for many weeks or months, or indefinitely after injury. Scars typically reach about 75-80% of normal skin breaking strength about 6-8 weeks after injury.

In general, scars typically have a triangular cross-section. That is, a scar is usually smallest in volume near the skin surface (i.e., stratum corneum and epidermis) and increases in volume as it progresses into the deeper layers of the dermis.

There are three common possible outcomes to a wound healing process. First, a normal scar can result. Second, a pathologic increase in scar formation can result, such as formation of a hypertrophic scar or a keloid. Third, the wound may not heal completely and become a chronic wound or ulcer. The devices, kits and methods described herein can ameliorate the formation of any type of scar. In addition, the devices, kits and methods described here can be adapted for a variety of wound sizes, and for different thicknesses of skin, e.g., the devices may be configured for use in different areas of the body. In addition, the devices, kits and methods described here can be adapted to ameliorate scar formation in any type of skin, e.g., body location, age, race, or condition.

Without wishing to be bound by any particular theory, we believe that mechanical strain acting on a wound or incision early in the proliferative phase of the wound healing process may inhibit cellular apoptosis, leading to a significant accumulation of cells and matrix, and hence increased scarring or the production of hypertrophic scars. Given the underlying similarities between hypertrophic scars and keloids with respect to excessive matrix formation, we believe that the devices and methods described herein may also be useful in preventing and treating keloids by offloading or neutralizing at least some of the strain that may be acting on the wound or incision. This tensile strain may be exogenous and/or endogenous strain, and may include but is not limited to the strain from the intrinsic tensile forces found in normal intact skin tissue.

Devices, kits and methods described herein may treat skin at a skin site ("skin treatment device"), including without limitation, to ameliorate the formation of scars at wound sites by controllably stressing or straining the epidermis and deeper layers of dermal tissue at or near a skin site, i.e., at or adjacent a wound or treatment site of a subject's skin, thereby reducing tensile or compressive stress at the skin site. The stress at the skin site may be reduced to levels below that experienced by normal skin and tissue. The stress or strain may be applied to surrounding tissue in one, two, or more directions to reduce endogenous or exogenous stress at the skin site in one, two or more directions. Thus, devices and methods described herein may reduce the stress experienced by skin and/or a wound and surrounding tissues in order to treat a subject. The device may also assist in preventing or reducing the incidence of wound dehiscence.

Devices kits and methods described herein may be for the preparation and/or application of a dressing. Such preparation may include but is not limited to, for example, removal of an adhesive liner, straining or tensioning a dressing, orienting a dressing for application and/or applying a medicament or other material to a portion of the dressing prior to application.

According to some variations, the packaging dressing carrier, support, base tensioning device or applicator tensioning device and/or applicator provide a release mechanism to separate the applied dressing from the packaging and/or applicator after the dressing is applied to the skin. According to a variation, a dressing may be prestrained and coupled to a dressing carrier, support, base tensioning device or applicator, for example as set forth in U.S. Provisional Application Ser. No. 61/512,340 filed on Jul. 17, 2011 and incorporated in its entirety herein by reference. One or more dressing releases described herein may be used with a dressing carrier, support, base tensioning device or applicator.

According to some variations, the tensioning device, dressing carrier, support, base or applicator may further comprise an opening, a window, or a clear or semi-opaque portion through which a wound, incision or other location may be visualized as the dressing is applied to the skin. According to some variations, the window guides the application of a dressing so that there is an optimal or desired distance between the wound and the edges of the dressing and/or so that the dressing is in an optimal location for unloading skin stresses.

According to some variations the applicator, tensioning device, or carrier, suppo or base may provide varied or variable flexibility to allow the dressing to be shaped when applied to various body locations or contours.

According to some variations, the applicator may be further used to help reduce bleeding, e.g., by allowing application of a compressive force using a support structure while or after the device is applied. One or more hemostatic or coagulative agents may be applied to, or otherwise integrated with dressing to help reduce bleeding. Potential agents include chitosan, calcium-loaded zeolite, microfibrillar collagen, cellulose, anhydrous aluminum sulfate, silver nitrate, potassium alum, titanium oxide, fibrinogen, epinephrine, calcium alginate, poly-N-acetyl glucosamine, thrombin, coagulation factor(s) (e.g. II, VII, VII, X, XIII, Von Willebrand factor), procoagulants (e.g. propyl gallate), antitibrinolytics (e.g. epsilon aminocaproic acid), and the like. In some variations, the agents may be freeze-dried and integrated into the dressing and activated upon contact with blood or other fluid. In some further variations, an activating agent may be applied to the dressing or the treatment site before the dressing is used on the subject. In still other examples, the hemostatic agent may be applied separately and directly to the wound before application of the dressing, or after application to the dressing via a catheter or tube. The devices may also comprise one or more other active agents that may be useful in aiding in some aspect of the wound healing process. For example, the active agent may be a pharmaceutical compound, a protein (e.g., a growth factor), a vitamin (e.g., vitamin E), or combinations thereof. A further example of such medicament may include, but is not limited to various antibiotics (including but not limited to cephalosporins, bactitracin, polyxyxin B sulfate, neomycin, polysporin), antiseptics (such as iodine solutions, silver sulfadiazine, chlorhexidine), antifungals (such as nystatin), antiproliferative agents (sirolimus, tacrolimus, zotarolimus, biolimus, paclitaxel), grow factors (such as VEGF) and other treatments (e.g. botulism toxin. Of course, the devices may comprise more than one medicament or agent, and the devices may deliver one or more medicaments or agents.

According to some variations, the applicator may also be used to strain a dressing prior to application to provide a dressing configured to ameliorate scar or keloid formation.

Devices are described here that may be used for ameliorating the formation of scars and/or keloids at a skin or wound site. The scars may be any type of scar, e.g., a normal scar, a hypertrophic scar, etc. in general, the devices may be configured to be removably secured to a skin surface near a wound. The devices may shield the skin or wound from endogenous stress and/or exogenous stress. In some variations, the devices may shield the skin or wound from endogenous stress without affecting exogenous stress on the skin or wound, e.g., devices that modify the elastic properties of the skin, etc. In other variations, the devices may shield the skin or wound from exogenous stress without affecting endogenous stress on the wound. Such variations may include situations where the musculature and surrounding skin or wound tissue has been paralyzed, e.g., through the use of botulinum toxin or the like. In still other variations, the devices shield the skin or wound from both endogenous and exogenous stress.

The devices or dressings described herein may treat skin at a skin site including without limitation to ameliorate the formation of scars at wound sites by controllably stressing or straining the epidermis and deeper layers of dermal tissue at or near a skin site, thereby reducing tensile or compressive stress at the skin site itself. The stress at the skin site may be reduced to levels below that experienced by normal skin and tissue. The stress or strain may be applied to surrounding tissue in one, two, or three or more directions to reduce endogenous or exogenous stress at the skin site in one, two or three or more directions. The physical characteristics of the dressing and/or the method of applying the dressing may also be further configured to resist or reduce the rate of skin stripping or tension blistering from the application of strain to the incision site. For example, the stretching of the adhesive regions when applied to the skin surface may result in an increased tissue density under the adhesive region. This may be the result of generally planar, tangential or parallel compression of skin tissue that is directly attached to that adhesive region, resulting from the relaxation of the adhesive region. In some examples, this tissue compression may reduce the risk of tissue stripping and/or blistering of skin in direct contact with the adhesive, in contrast to bandage "strapping" where one end of a bandage is adhered to the skin and then tensioned or pulled across a wound before the other end is attached to the skin on the opposite side of the wound. Bandage "strapping", while generating tension in the bandage during the application, may simultaneously generate a relatively high tissue strain at the first adhesion site. This high tissue strain then decreases when the bandage is attached to the skin at a second adhesion site as the high peak stresses are redistributed along the skin under the bandage. In contrast, when a pre-strained bandage is applied to the skin, little if any strain may be transferred or generated in the skin as the adhesive regions are applied to the desired locations. When the pre-strained bandage is permitted to relax, however, the strain (or peak strain) in the skin may be increased. Thus, with a pre-strained bandage, temporary high tissue strain may be avoided or otherwise reduced during the application procedure. In other variations, however, the dressing may also be applied to the skin by strapping, or by a combination of pre-straining and strapping.

The dressing may comprise an elastic member, such as a sheet of elastic material. The elastic material of the dressing may comprise a single layer of material or multiple layers of the same or different materials. The material may have any of a variety of configurations, including a solid, foam, lattice, or woven configuration. The elastic material may be a biocompatible polymer, e.g., silicone, polyurethane, TPE (thermoplastic elastomers), synthetic rubber or co-polyester material. The thickness of polymer sheets may be selected to provide the dressings with sufficient load carrying capacity to achieve desired recoverable strains, and to prevent undesired amounts of creep deformation of the dressings over time. In some variations, the thickness across dressings is not uniform, e.g., the thickness across the dressing may be varied to change the stiffness, the load carrying capacity, or recovery strains in selected orientations and/or locations. The elastic material of the exemplary dressing may have a thickness in the range of about 50 microns to 1 mm or more, about 100 microns to about 500 microns, about 120 microns to about 300 microns, or in some variations about 200 microns to about 260 microns. The exemplary dressings have an edge thickness of about 500 microns or less, 400 microns or less, or about 300 microns or less may exhibit less risk of skin separation from inadvertent lifting when inadvertently brushed against clothing or objects. In some variations, the dressings are tapered near the edges to reduce thickness. A tapered edge may also ameliorate peak tensile forces acting on skin tissue adjacent to the adhesive edges of the dressing. This may or may not reduce the risk of skin blistering or other tension-related skin trauma. In other variations, the edges of the dressing may be thicker than the middle of the dressing. It is hypothesized that in some configurations, a thicker dressing edge may provide a relative inward shift of the location of the peak tensile forces acting near the dressing edge, compared to dressings of uniform thickness. The elastic material may have a load per width of at least 0.35 Newtons per mm at an engineering strain of 60% or a load per width of at least 0.25 Newtons per mm at an engineering strain of 45%. The elastic material may have a load per width of no greater than about 2 Newtons per mm at the engineering strain of about 45% to 60%, about 1 Newtons per mm at the engineering strain of about 45% to 60%, about 0.7 Newtons per mm at the engineering strain of about 45% to 60%, or no greater than about 0.5 Newtons per mm at the engineering strain of about 45% to 60%. The system elastic material may have a load per width that does not decrease from an engineering strain of 0% to 60%, a load per width plot that increases linearly from an engineering strain of 0% to 60%, or a load per width plot that is not convex from an engineering strain of 0% to 60%. The elastic material may comprise an adhesive configured to maintain a substantially constant stress in the range of 200 kPa to about 500 kPa for at least 8 hours when strained to an engineering strain of about 20% to 30% and attached to a surface. The elastic material may comprise an adhesive configured to maintain a substantially constant stress in the range of 200 kPa to about 400 kPa for at least 8 hours when strained to an engineering strain of about 20% to 30% and attached to a surface. The substantially constant stress may vary by less than 10% over at least 8 hours, or by less than 5% over at least 8 hours.

Although the depicted dressings may have a generally rectangular configuration with a length and/or width of about 160 mm to about 60 mm, in other variations the dressing may have any of a variety of lengths and widths, and may comprise any of a variety of other shapes. Also, the corners of the dressing may be squared or rounded, for example. The lengths and/or widths of an exemplary dressing may be in the range of about 5 mm to about 1 meter or more, in some variations about 20 mm to about 500 mm, and in other variations about 30 mm to about 50 mm, and in still other variations about 50 mm to about 100 mm. In some variations, the ratio of the maximum dimension of the dressing (e.g. its length) to an orthogonal dimension to the maximum dimension (e.g. width), excluding the minimum dimension of the dressing (e.g. the thickness), may be in the range of about 1:3, about 1:2, about 1:1, about 2:1, about 3:1, about 4:1 about 5:1, about 6:1, about 7:1, about 8:1, about 9:1 or about 10:1 or greater. In some variations, the strain axis of the dressing in use may be oriented with respect to the maximum dimension or to the orthogonal dimension to the maximum dimension. In some variations, the final compressive stress and strain imposed onto the skin by the elastic material may be the result of the dynamic equilibrium between the tensile stress in the skin and the elastic material of the dressing. The skin at the skin site typically comprises an inherent tension that stretches incision site, whether or not any tissue was excised from the skin site. The elastic material and the adhesive region may be configured to be applied to a skin location so that when the dressing is stretched to a particular tension and then adhered to the incision site, tensile stress in the dressing is transferred to the incision site to compress the tissue directly under the dressing along a tangential axis to the skin surface, the stress and strain imposed onto the skin location has a net or resultant orientation or axis is also generally tangential or planar to the elastic material and/or the outer surface of the skin location, with a similar axis to the orientation or axis of the tensile stress in the dressing. The tension in the dressing will relax to a tension level that maintains equilibrium with increased tension in the skin adjacent to the dressing. The application of the dressing to the skin location may involve the placement of the dressing without overlapping or being wrapped onto itself, e.g. wherein only adjacent regions of the dressing are interconnected and wherein non-adjacent regions of the dressing are not interconnected. The actual amount of stress and strain imposed on the skin may vary, depending upon the particular person, skin location, the thickness or various mechanical characteristics of the skin layers (e.g. epidermis, dermis, or underlying connective tissues), and/or the degree of pre-existing scarring, for example in some further variations, the wound treatment dressing may be selected or configured for use at a specific body location, such as the scalp, forehead, cheek, neck, upper back, lower back, abdominal region, upper torso (including but not limited to the breast folds), shoulder, upper arm, lower arm, palm regions, the dorsum of the hand, finger, thigh, lower leg, the dorsum or plantar surface of the foot, and/or toe. Where applicable, some body regions may be further delineated into anterior, posterior, medial, lateral, proximal and/or distal regions, e.g. the arms and legs.

The dressing may be configured to impose a skin strain in the range of about 10% to about 60% or more, in other configurations about 15% to about 50%, and in still other configurations, about 20% to about 30% or about 40%. To achieve the desired degree of skin strain, the dressing may be configured to undergo elastic tensile strain in the range of about 20% to about 80% or more, sometimes about 30% to about 60%, and other times about 40% to about 50% or about 60%. The dressing may comprise any of a variety of elastic materials, including but not limited to silicones, styrenic block copolymers, natural rubbers, fluoroelastomers, peril uoroelastomers, polyether block amides, thermoplastic elastomers, thermoplastic polyurethane, polyisoprene, polybutadiene, and the like. The material of the exemplary dressing may have a Shore A durometer in the range of about 20 to about 90, about 30 to about 80, about 50 to about 80. The exemplary dressing was constructed of MED 82-5010-05 by NUSIL TECHNOLOGY LLC (Carpinteria, Calif.). Other examples of suitable materials are described in U.S. application Ser. No. 11/888,978, which was previously incorporated by reference in its entirety.

When the dressing is applied to a skin location and allowed to at least partially recover to its base configuration, the recovery level or equilibrium level of strain in the dressing may be in the range of about 4% to about 60% or more, in other configurations about 15% to about 50%, and in still other configurations, about 20% to about 30% or about 40%. The ratio between the initial engineering tensile strain placed onto the dressing before recovery and the resulting engineering compressive strain in the skin may vary depending upon the skin type and location, but in some examples, may be about 2:1. In other examples, the ratio may be in the range of about 4:1 to about 5:4, about 3:1 to about 5:3, or about 5:2 to about 2:1. These skin strain characteristics may be determined with respect to a reference position of the body or body part, e.g. anatomical position, to facilitate reproducible measurements. The particular degree of strain may be characterized as either an engineering strain or a true strain, but may or may not be calculated based upon or converted from the other type of strain (e.g. the strain may be based upon a 45% engineering strain that is converted to a true strain).

In some further variations, one or more characteristics of the elastic material may correspond to various features on the stress/strain curve of the material. For example, the engineering and true stress/strain curves for one specific example of the dressing comprises a material that exhibits an engineering stress of about 1.2 MPa at about 60% engineering strain, but in other examples, the engineering stress may be in the range of about 900 KPa to about 3.5 MPa, about 1 MPa to about 2.2 MPa, about 1 MPa to about 2 MPa, about 1.1 MPa to about 1.8 MPa, about 1.1 MPa to about 1.5 MPa, about 1.2 MPa to about 1.4 MPa. When unloading or relieving stress from the dressing, the material may be configured with an engineering stress of about 380 KPa at about 40% engineering strain, but in other examples, the engineering stress during unloading of the material to about a 40% strain may be in the range of about 300 KPa to about 700 KPa, about 325 KPa to about 600 KPa, about 350 KPa to about 500 KPa, or about 375 KPA to about 425 KPa. When unloading the material to an engineering strain of about 30%, the material exhibits an engineering stress of about 300 KPa, but in other examples, the engineering stress when unloading the material to about 30% strain may be in the range of about 250 KPa to about 500 KPa, about 275 KPa to about 450 KPa, about 300 KPa to about 400 KPa, or about 325 KPA to about 375 KPa. When unloading to an engineering strain of about 20%, the material may have an engineering stress of about 100 KPa, but in other examples, the unloading engineering stress at about 20% may be in the range of about 50 KPa to about 200 KPa, about 75 KPa to about 150 KPa, or about 100 KPa to about 125 KPa. In some examples, the material may be configured to at least achieve a specific range or level of engineering stress at each of the specified engineering strain levels described above, but in other examples, the material may be configured for lower levels of maximum engineering strain, e.g. up to about 30% or about 40%.

In some examples, certain portions of the stress/strain curve may have a particular morphology. For example, for a particular level of maximum strain the loading curve may be generally linear on the corresponding true stress/strain curve. In an example using a dressing described herein, up to a true strain of about 45%, the loading curve had a generally linear configuration. In other examples, the configuration may only be linear along a portion of the loading curve or may be curved along the entire loading curve. Where the loading curve is non-linear, the loading curve may be convex, concave or both. Also, in some examples, the tangent line of the loading curve (i.e. the line between the two triangles) may also be generally co-linear.

In some variations, the elastic material comprises a material having an elastic modulus E of at least about 1 MPa, about 1.5 MPa, about 2 MPa, about 2.5 MPa, about 3 MPa, about 3.5 MPa, about 4 MPa, about 5 MPa, about 6 MPa, about 7 MPa, about 8 MPa, about 9 MPa or at least about 10 MPa or greater. The material elastic modulus E may be no greater than about 10 MPa, about 9 MPa, about 8 MPA, about 7 MPa, about 6 MPa, or about 5 MPa, or about 4 MPa.

In addition to the absolute stress levels at certain strain levels described above, the material may also be characterized with respect to the ratio between a) the stress to achieve a particular strain during loading, and b) the stress at the same strain during unloading. For example, the material may have a ratio of at least 4:1 to about 3:2 at each of the 20%, 30% and 40% strain levels, but in other examples, the material may exhibit these ratios only at 20%, at 30%, or at 40% strain levels, or at both 20% and 30% but not 40%, or at both 30% and 40% but not 20%. In other examples, the ratio at one, some or all of the strain levels may be in the range of about 3:1 to about 2:1, or about 5:2 to about 2:1.

In some examples, the elastic material of the dressing may be configured under testing conditions to achieve a stable level of stress at a constant strain, e.g. the material exhibits a limited amount of stress relaxation over a particular period of time and at a particular level of strain. The period of time may be at least about 8 hours, about 12 hours, about 18 hours, about 24 hours, about 36 hours, about 48 hours, about 72 hours, about 4 days, about 5 days, about 6 days, or about a week or more. The level of strain may be about 10%, about 20%, about 30%, about 40%, about 50%, about 60%, about 70%, or about 80% or more. The stress of the exemplary dressing over various time curves may be configured to maintain an engineering stress of about 300 KPa at an engineering strain of about 30% without noticeable deviation over a period of about 1 hour, about 2 hours, about 3 hours, about 4 hours, about 5 hours, about 6 hours, about 7 hours, or about 8 hours or more. The stresses at 10% strain, 20% strain, and at 40% may be lower or higher.

In some variations, the elastic material or the dressing may be configured under testing conditions to maintain a particular minimum level of stress when held at a constant strain over a particular time period. In an example to assess the ability of a backing material to maintain a stress and strain on skin over time, engineering strains were measured while each backing material was tensile strained to 60% at a rate of 100 microns per second and held for 10 minutes, and then dropped to a strain of 30% at a rate of 100 microns per second and held for 9 hours. For example, the exemplary dressing is able to maintain an engineering stress level of about 350 KPa at an engineering strain of 30%. In some other examples, the minimum level of stress may be about 100 KPa, about 120 KPa, about 140 KPa, about 160 KPa, about 180 KPa, about 200 KPa, about 220 KPa, about 240 KPa, about 260 KPa, about 280 KPa, about 300 KPa, about 320 KPa, about 340 KPa, about 360 KPa, about 380 KPa, about 400 KPa, about 420 KPa, about 440 KPa, about 460 KPa, about 480 KPa, about 500 KPa, about 600 KPa, about 700 KPa, about 800 KPa, about 900 KPa or about 1000 KPa or greater. The level of constant strain may be different in other configuration, with a level of about 15%, about 20%, about 25%, about 30%, about 35%, about 40%, about 45%, about 50%, about 55%, about 60%, about 65%, about 70%, about 75%, or about 80%. The time period over which the dressing is able to maintain a stress level may be at least about 2000 seconds, about 3000 seconds, about 4000 seconds, about 5000 seconds, about 6000 seconds, about 7000 seconds, about 8000 seconds, about 9000 seconds, about 10000 seconds, about 20000 seconds, about 30000 seconds, about 40000 seconds, about 50000 seconds, about 60000 seconds, about 70000 seconds, about 24 hours, about 36 hours, about 48 hours, about 72 hours, about 4 days, about 5 days, about 6 days, about 7 days, about 10 days, about 2 weeks, about 1 month or more. In some variations, the dressing, the elastic material and/or the adhesive material is configured to exhibit less than about a 15% change in stress or strain level over the particular period when applied to a skin surface or test surface. In other examples, the degree of change may be about 12%, about 10%, about 8%, about 6%, about 5%, about 4%, about 3%, or about 2% or less. The stress or strain may be an engineering stress or strain, and/or a true stress or strain.

The adhesive used may be, for example, a pressure activated adhesive (PSA), as a silicone, acrylic, styrene block copolymer, vinyl ether, nitrile or other PSA. In other variations, a non-pressure sensitive adhesive may be used, including but not limited a heat or light-cured adhesive. The pressure sensitive adhesive may be made from, e.g., polyacrylate-based, polyisobutylene-based, silicone-based pressure sensitive adhesives, synthetic rubber, acrylic, and polyisobutylene (PIB), hydrocolloid, and the like. The T-peel release force and blunt probe tack force of the adhesive may be measured by a standardized test method, such as ASTM D1876 and ASTMD2979 or other appropriate method. In some variations, the T-peel release force or blunt probe tack test value of the adhesive is configured to maintain loads of at least about 50 mPa/mm for at least about 24 hours, about 48 hours, about 72 hours, about 1 week, about 2 weeks, about 3 weeks, about 4 weeks or more. In other variations, the loads may be at least about 75 mPa/mm, about 100 mPa/mm, about 125 mPa/mm, or at least about 150 mPa/mm over the particular time period. The degree of adhesion e.g., as measured by the T-peel release force or blunt probe tack test value) may vary depending upon the degree of strain placed onto the skin or incision site, and in some variations, these time periods may be based upon an average skin strain of about 10%, about 20%, about 30%, about 40%, or about 50% or more. In some variations, the adhesive may have a T-peel release force of at least about 150 kg/m, about 160 kg/m, about 170 kg/m, about 180 kg/m, about 190 kg/m, about 200 kg/m, about 210 kg/m, about 220 kg/m, about 230 kg/m, about 240 kg/m, about 250 kg/m, about 260 kg/m, about 270 kg/m, about 280 kg/m, about 290 kg/m, about 300 kg/m, about 310 kg/m, about 320 kg/m, about 330 kg/m, about 340 kg/m, about 350 kg/m, about 400 kg/m, about 450 kg/m, or at least about 500 kg/m or higher. In some further variations, the T-peel release force may be no greater than about 1000 kg/m, about 900 kg/m, about 800 kg/m, about 700 kg/m, about 600 kg/m, about 500 kg/m, about 400 kg/m or about 300 kg/m. The blunt probe tack test value of the adhesive may be at least about 0.50 kg, about 0.55 kg, about 0.60 kg, about 0.65 kg, about 0.70 kg or about 0.75 kg or higher, and may be no greater than about 1 kg, about 0.9 kg, about 0.8 kg, about 0.7 kg, or about 0.6 kg. The T-peel release force and blunt probe tack force may be measured by a standardized test method, such as ASTM D1876 and ASTMD2979 or other appropriate method. Other features or variations of the device are described in U.S. application Ser. No. 11/888,978, filed on Aug. 3, 2007, incorporated in its entirety herein by reference.

The release liners may comprise any of a variety of materials, including both opaque and transparent materials. The release liners may comprise Mylar or paper, or any other material with reduced adhesion to the adhesive material(s) of the device. For example, for a silicone adhesive, a fluoropolymer-treated polyester film may be used, and for an acrylic pressure sensitive adhesive, a silicone treated polyester or Mylar film or silicone treated craft paper may be used, in variations where the device has multiple separate adhesive regions, separate release liners may be provided for each region, or some regions may be covered by the same release liner.

Examples of dressings, applicators or tensioning devices that may be used in the devices kits or methods herein may include those provided in U.S. application Ser. No. 12/854,859 filed Aug. 11, 2010 and U.S. application Ser. No. 13/345,524 filed Jan. 6, 2012, and the disclosures of which have been previously incorporated by reference in their entirety without limitation.

Attachment structures of a dressing assembly, dressing carrier, support, base, applicator, tensioning or straining device may include any structures that are used to attach or couple an applicator, tension or straining device to a dressing. A dressing may or may not have attachment features or structures. Any such attachment features may be integral with or include any of the attachment structures or corresponding structures to the attachment structures of the applicator dressing and/or tensioning device.

In some variations the assembly may comprise one or more mechanisms or elements configured to facilitate separation, release, removal or detachment of the dressing from the applicator or tensioning device, other attachment elements or other portions of the dressing assembly, including but not limited to the separation devices and methods described in co-pending U.S. application Ser. No. 13/345,524 filed Jan. 6, 2012. Release elements or releasable attachment structures may include but are not limited to pockets and tabs, hook and loop mechanism, hooks, angled bars, pivoting, rolling, rocking or sliding features associated with or coupled to attachment structures, adhesives, removable adhesives, adhesive tapes or other adhesive devices, pegs, rip cords, towel bar configurations, sliding pins, friction locks, cam locks, vacuum or suction devices, snap connectors, carpet tack, press fit connections or other connections, levers, latches, locking members, spring members, for example, or other mechanisms such as cutters or rip cords or other structures or features to facilitate tearing, cutting or separation of attachment structures or elements perforated or otherwise severable structures, that permit removal of dressing from the applicator, other portions of the dressing assembly and/or attachment structures, features, elements or portions They may be self-releasing latches or spring members. They may be actuated when a pressure member is applied to a skin treatment device prior to removing the applicator, They may be manually actuated.

In some examples, the straining device may be configured to impart and/or maintain a single predetermined or pre-set strain or a plurality of predetermined or pre-set strains, or predetermined maximum or minimum amounts of strain. A applicator, tensioning or straining device that is described as being in an unstrained configuration is in a configuration in which a dressing may be unstrained or relatively less strained when attached to the applicator, tensioning or straining device. An applicator, tensioning, or straining device that is described herein as being in a strained configuration, is in a configuration in which a dressing may be strained or relatively more strained when attached to the applicator, tensioning or straining device, or with respect to an unstrained configuration, when applied to a subject's skin.

Devices, applicators, tensioning devices, and corresponding attachment features may be configured to provide multi-direction strain or additional strain in an orthogonal direction to a dressing. In some variations, the attachment features may be configured to provide radial strain (e.g., where the direction of the strain radiates from a central region of a dressing). For example, an applicator or tensioning device may radially strain the dressing such that the dressing applies a radially inward compressive force when adhered to the skin. Such devices may be typically circular, oval, egg, kidney bean, or other arcuate shapes disclosed elsewhere herein.

The applicator, tensioning device and/or attachment structure profile may be straight, curved or otherwise varied. For example, the shape of the elements of a device may be configured to follow the shape of the area of the subject's body to which the skin treatment device is to be attached. A tensioning device, applicator or elements thereof may be selected or configured to have a profile that has a desirable profile for a particular body location or profile where the skin treatment device is to be placed on a subject's skin. A applicator, tensioning device or elements thereof may be selected or configured to closely match a portion of a subject's body profile. The applicator or tensioning device and/or an element or segment thereof, may be curved, curvable, flexible, bendable, malleable, deformable, shapeable or movable to provide alternative shapes or profiles of an attached dressing. They may be relatively curved, curvable, flexible, malleable, bendable, deformable, shapeable or movable in at least one direction while being more rigid in another direction.

A variety of locking, latching, securing, attaching or detail mechanisms may be used to maintain the applicator or tensioning device in a various configurations including but not limited to unstrained, partially strained, strained configurations. A variety of locking, latching or detent mechanisms may be used to maintain a dressing in a variety of configurations including unstrained, partially strained, strained. By locking the, applicator, tensioning device, or dressing in a strained position, a predetermined strain of a given dressing may be achieved. The predetermined amount of strain may be a predetermined absolute percentage of strain or level of force that is independent of the shape and/or size of the treatment site. As a further example, this absolute percentage of strain or level of force may or may not be independent of the minimum strain or force to achieve sutureless wound closure (e.g. a relative strain or three to achieve opposition of the incision edges of a treatment site). Furthermore, the force needed to achieve wound closure is not a predetermined strain or force, since the final level of strain or force is not known until opposition of the incision edges is achieved.

According to some variations, the cover and/or base or elements or segments of a tensioning device may be constructed to be sufficiently firm or rigid or less flexible relative to an attached dressing to support an attached dressing until it is applied to a subject as described with respect to the variations herein. Such material may comprise, for example, a plastic, e.g., polypropylene, polycarbonate, polytetrafluoroethylene (PTFE or TEFLON®), LDPE, high-density polyethylene (HDPE), ultra high-molecular weight polyethylene (UHMWPE), polyvinyl chloride (PVC) or acrylic, nylon or a paperboard. The elements or segments may be a laminate of a material, such as a solid bleach sulfate paperboard with a layer of flexible material between layers of paperboard, for example, silicone, polyurethane, LDPE or a rubber material. The material may also be a metal as for example, ductile aluminum or stainless steel. The metal may comprise a foil, ribbon, wire or other form.

FIGS. 1A and 1B depict one variation of a wound treatment device 2, comprising an elastic layer of material 4 with an upper surface 6, a lower surface 8, and edges 10, 12, 14 and 16. The lower surface 8 of the elastic layer of material 4 may comprise a central non-adhesive region 18 flanked by two inner adhesive regions 20 and 22 along borders 24 and 26. In this particular variation, the central non-adhesive region 18 also has two borders 28 and 30 which are adhesive-free. This configuration may facilitate the treatment of longer incisional sites by serially placing the non-adhesive regions of multiple wound treatment devices along the incisional site, without the device edges directly adhering to the incisional site.

In some variations, the average width of the non-adhesive region, i.e. the distance between the adhesive regions along the axis of strain (or where the device is strained along multiple dimension, the largest dimension of the device 2 along one of its axes of strain), is in the range of about 3 mm to about 15 mm or more, in some variations about 5 mm to about 10 mm, and in other variations about 7 mm to about 8 mm. The width of the adhesive region may be the same or greater than the width of the non-adhesive regions, including but not limited to being 2×, 3×, or 4× or more in relative width. In some variations, the greater width of the adhesive regions relative to the non-adhesive region may lower focal concentrations of tissue stress, which may reduce tissue stripping and/or blistering. The widths of the non-adhesive region and/or the adhesive regions may be constant or may be variable, and the widths of the adhesive regions may be the same or different.

The inner adhesive regions 20 and 22 may comprise outer borders 32 and 34 which are opposite of the inner borders 24 and 26 shared with the central non-adhesive region 18 and shared with the outer non-adhesive regions 36 and 38. The non-adhesive regions 36 and 38 may further comprise applicator attachment regions or structures 40 and 42 that are configured to releasably attach to an applicator that may be used to apply the device 2 to a treatment site. In some further variations, the attachment structures may also facilitate stretching of the central adhesive region 18 and/or the adhesive regions 20 and 22. Various examples of applicators that may be used are described in greater detail below. In other variations, the applicator attachment structures 40 and 42 may be located in adhesive regions that may or may not be contiguous with more inner adhesive regions. In other variations, the elastic material about the attachment structures may comprise an adhesive. Examples of applicators are described in greater detail below.

The applicator attachment structures 40 and 42 may comprise a plurality of openings 44 and 46 located through the layer of elastic material 4. The openings 44 and 46 may be through-openings between the upper and lower surfaces. In other variations, the openings may be close-ended openings, e.g. a plurality of pockets or even a single pocket spanning the width or a portion of the width of the device.

In the variation depicted in FIGS. 1A and 1B, the openings 44 and 46 are configured to be fully penetrated by the applicator, but in other variations, the applicator and/or the openings may be configured for only partial insertion by the applicator. The openings 44 and 46 may be circular, ovoid, triangular, rectangular, square, polygonal or any other of a variety of shapes. Each of the openings may have the same or a different shape, size or configuration, and the shape, size or configuration may vary between the upper surface and the lower surface. The openings may be also be angled with respect to the upper surface or lower surface, and in some variations, one or more openings and/or a region about the openings may be partially or completely reinforced by wires, rings and/or frames and the like. In some variations, the applicator attachment structures may also comprise denser or thicker regions of the elastic material. In some variations, multiple sets of applicator attachment structures may be provided to permit use of different applicators or to strain the device to different degrees, for example.

Figure 6A:
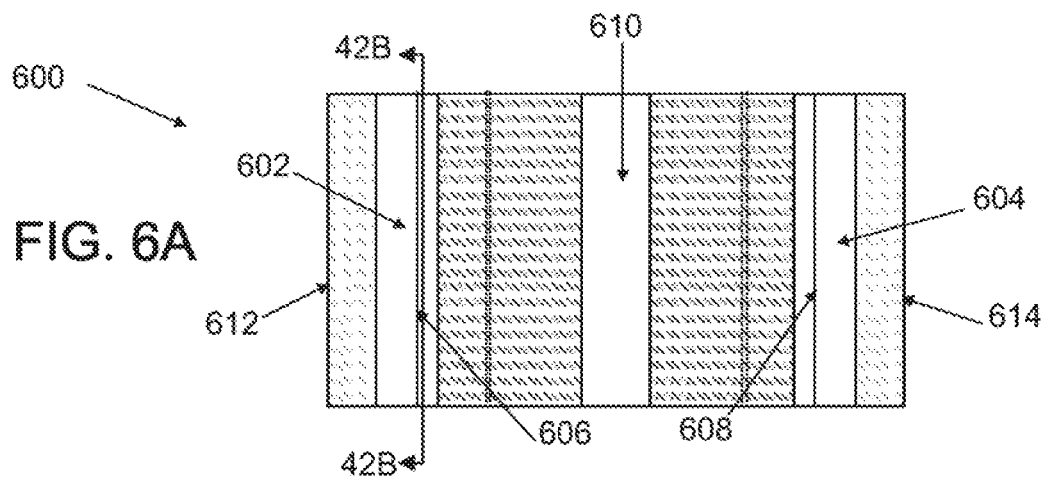
FIGS. 6A to 6C are superior, cross sectional and side elevational views of a dressing comprising pockets.
Figure 6B:
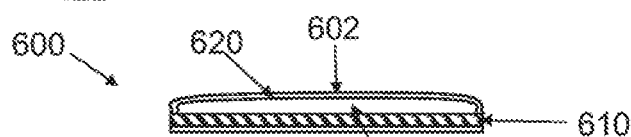
Figure 6C:
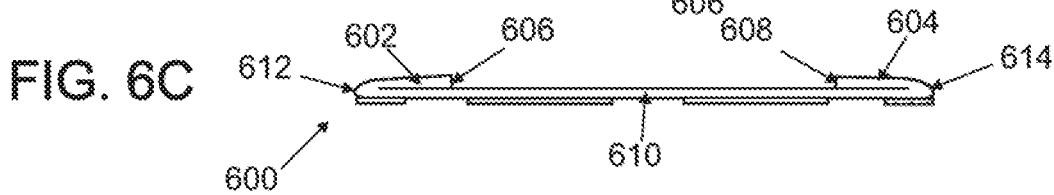
Figure 7A:
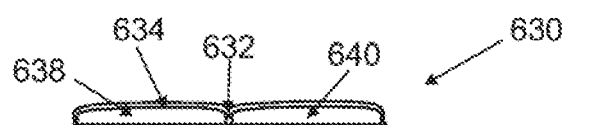
FIGS. 7A to 7C are cross sectional views of alternate embodiments of a dressing comprising pockets.
Figure 7B:
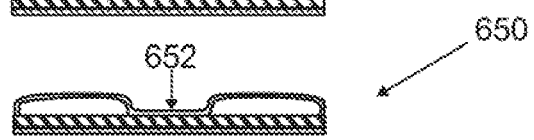
Figure 7C:
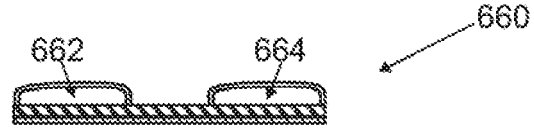

FIGS. 6A to 6C depict another variation of the dressing 600 comprising pockets 602 and 604 with inwardly facing pocket openings 606 and 608 configured to receive the attachment structures of a corresponding applicator. The pockets may comprise separate sheets of material that are attached to the elastic material and may comprise the same or a different material as the other portions of the dressing. The separate sheets of material may be adhered to the elastic material using adhesives, heat or plasma bonding, chemical bonding or mechanical attachment structures (e.g. staples and stitches). In the example depicted best in FIGS. 6B and 6C, the pockets 602 and 604 may be integrally formed structures of the base layer 610 that are folded over from the ends 612 and 614 of the dressing 600 and attached onto itself along the edges 616 and 618 without bonding the opening edge 620 to form the opening 606. In other variations, such as the dressing 630 depicted in FIG. 7A, the inner portions 632 of a pocket structure 634 or the distal edge 636 may also be adhered or fused to form multiple subpockets 638 and 640. Although FIG. 43A depicts a dressing with two subpockets 638 and 640, in other variations, three, four, five, six, seven, eight or more subpockets may be provided. The area or width of the fused inner portion(s) 652 may also vary, as shown in the dressing 650 in FIG. 7B. The width of the fused inner portion(s) may be in the range of about 0.5 mm to about 10 mm or more, sometimes about 1 mm to about 5 mm, and other times about 1 mm to about 2 mm. As shown in the dressing 660 of FIG. 7C, in other variations, the subpockets 662 and 664 may also be separately provided without an inner portion interconnecting them. In some further variations, the opening(s) of the pocket structures may be closed or sealed shut after application. Closure may result from using an adhesive, complementary sealable groove structures about the pocket openings (e.g. sandwich bag seal) or as a result of the cohesive properties of the elastic material when the pocket is pressed down. Closure of the pockets may reduce the risk of snagging the dressing following its application.

In other variations, the applicator attachment structures may comprise one or more projections or other structures protruding from the surface of the wound treatment device that form a mechanical or frictional interfit with the applicator. Referring to FIGS. 8A to 9B, examples of these alternate attachment structures include T-bar 672 or eyelet projections 682 of the dressings 670 and 680 that may be releasably engaged by an applicator. The t-bar 672 and eyelet projections 682, may be integrally formed with the base elastic layer 674 and 684 of the dressings 670 and 680, or may comprise a different material that is partially embedded in the elastic layer 674 and 684. In still other variations, the t-bar or eyelet projections may comprise individual or common base or pad structures that may be adhered to the surface of the elastic layer 674 and 684. The number of projecting attachment structures per side of the dressing may be in the range of about one to about twelve or more, sometimes about three to about eight, and other times about four to about five.

Figure 11:
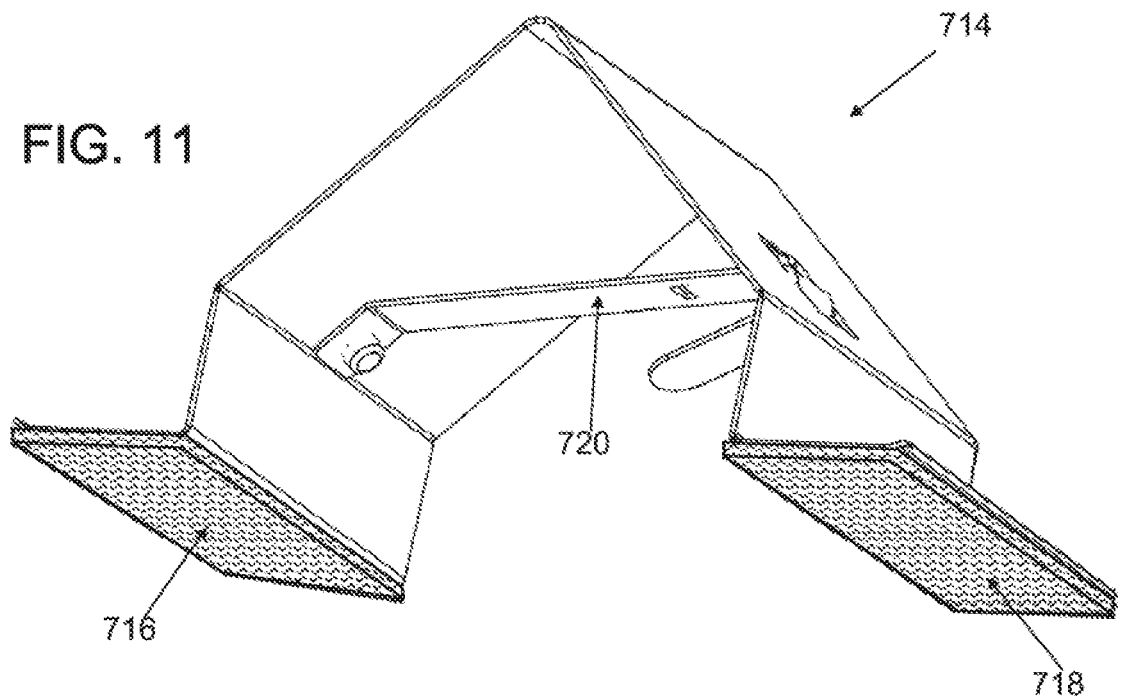
FIG. 11 depicts an applicator with corresponding hook-and-loop type of attachment structures configured for use with the dressing in FIGS. 10A to 10C.
Figure 12:
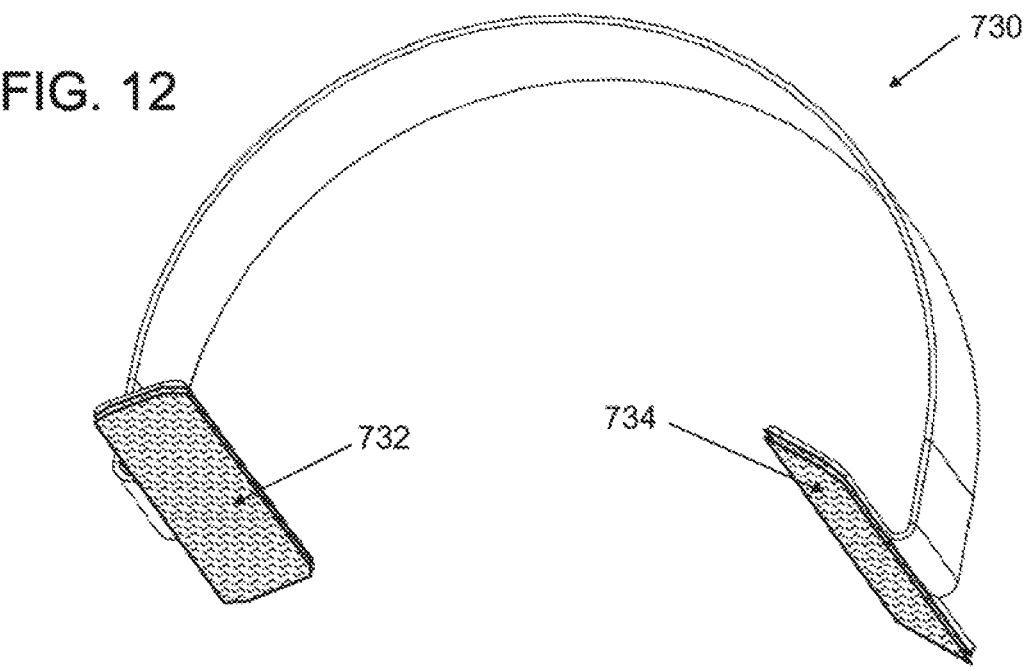
FIG. 12 depicts another applicator with corresponding hook-and-loop type of attachment structures configured for use with the dressing in FIGS. 10A to 10C.

In still another variation, the dressing may comprise complementary hook-and-loop attachment regions (e.g. VELCRO®) that may releasably attach to an applicator with a corresponding hook-and-loop attachment regions. In FIGS. 10A to 10C, for example, the bandage 700 comprises loop attachment regions 702 and 704 that are adhered to the upper surface 706 of the bandage 700, and with various adhesive regions 708a/b and 710a/b located on the lower surface 712. In use, a corresponding applicator, including but not limited to the exemplary applicator 714 depicted in FIG. 11, is squeezed or compressed to reduce the spacing between corresponding hook regions 716 and 718 to correspond to the spacing of the loop attachment regions 702 and 704 of the bandage 700 in its unstretched state. The hook regions 716 and 718 are aligned and then pressed against the loop attachment regions 702 and 704 to engage the bandage 700. In some examples, the applicator 714 may comprise a locking mechanism 720 to maintain the applicator 714 in a compressed state during engagement of the bandage 700, but in other examples, such as the applicator 730 in FIG. 12, the user will manually maintain the applicator 730 in a compressed state to align its hook regions 732 and 734 to the loop regions 702 and 704 to engage the bandage 700. A locking mechanism is not used. In some alternate application procedures, the applicator 714 (or 730) is not squeezed and instead, one of the loop regions 702 and 704 of the bandage 700 is first attached to a corresponding hook region 716 or 718, for example, and then the bandage 700 may be stretched and the remaining loop region 702 or 704 is attached to the applicator 714.

Although the examples in FIGS. 10A to 12 illustrate the loop regions 702 and 704 on the bandage 700 and the hook regions 716 and 718 located on the applicator 714, for example, in other variations, the relative relationships between the hook and the loop attachment regions may be reversed. The hook-and-loop attachment regions may be provided on any of the variety of dressing applicators the variety of applicators described herein.

In some variations, one or more flap regions 49 and 51 may be provided adjacent to the outer non-adhesive regions 36 and 38, or the applicator attachment structures 40 and 42. Each of the flap regions 49 and 51 may be located directly between an edge 10 and 12 of the treatment device 2 and the outer non-adhesive regions 36 and 38 or applicator attachment structures 40 and 42. During use or preparation of the treatment device 2 for application to the skin, the flap regions 49 and 51 may remain unstretched relative to the central non-adhesive region 18 and inner adhesive regions 20 and 22. Once the adhesive regions 20 and 22 are adhered to the skin, the flap regions 49 and 51, which may optionally also comprise an adhesive on their skin contacting surface, may be adhered to the skin. The flap regions may be adhered to the skin in an unstrained state, or in a strained state that is less than, equal to, or greater than the strain in the central non-adhesive region 18 and adhesive regions 20 and 22. In still other variations, the flap regions may be cut or separated from the dressing after the dressing is applied. Perforations may be provided between the adhesive regions and the flap regions to facilitate separation.

The adhesive provided on the lower surface of the flap regions 49 and 51 may be the same or may be different than the adhesive of the inner adhesive regions 20 and 22, including but not limited to the composition, thickness and/or distribution of the adhesive material. In some variations, the adhesive of the flap regions 49 and 51 may have a reduced T-peel release force and/or blunt probe tack force relative to the adhesive provided for the inner regions 20 and 22. Various T-peel release force and/or blunt probe tack force ranges for the adhesive are provided below. In some variations, the unstrained or less-strained flap regions may redistribute at least some of the strains acting on tissue about the transition regions along the outer borders 32 and 34 of the inner adhesive regions 20 and 22. This may or may not reduce the risk of skin stripping or blistering compared to devices without flap regions or with flap regions of smaller width. In some variations, the actual width of a section of the flap region or the average width of the flap region or (or adhesive portion of the flap region) may be characterized relative to the corresponding width of the closest inner adhesive region and/or the width of the closest outer non-adhesive region. The width of the flap region may be in the range of about 1 mm to about 10 cm or more, sometimes about 5 mm to about 3 cm, and other times about 1 cm to about 2 cm. The size of the flap region may be also characterized relative to the size of the other regions of the dressing. For example, in some variations, the width of the flap region may be at least about 25%, about 33%, about 50%, about 75%, about 100%, or about 120% or higher than the corresponding width of the closest inner adhesive region. The width of the flap region relative to the closest outer non-adhesive region may be at least about 50%, about 75%, about 100%, about 120% or higher.

The stretching of the adhesive regions when applied to the skin surface may result in an increased tissue density under the adhesive region. This may be the result of generally planar, tangential or parallel compression of skin tissue that is directly attached to that adhesive region, resulting from the relaxation of the adhesive region. In some examples, this tissue compression may reduce the risk of tissue stripping and/or blistering of skin in direct contact with the adhesive, in contrast to bandage "strapping" where one end of a bandage is adhered to the skin and then tensioned or pulled across a wound before the other end is attached to the skin on the opposite side of the wound.

Furthermore, bandage "strapping", while generating tension in the bandage during the application, may simultaneously generate a relatively high tissue strain at the first adhesion site. This high tissue strain then decreases when the bandage is attached to the skin at a second adhesion site as the high peak stresses are redistributed along the skin under the bandage. In contrast, when a pre-strained bandage is applied to the skin, little if any strain may be transferred or generated in the skin as the adhesive regions are applied to the desired locations. When the pre-strained bandage is permitted to relax, however, the strain (or peak strain) in the skin may be increased. Thus, with a pre-strained bandage, temporary high tissue strain may be avoided or otherwise reduced during the application procedure. In other variations, however, the device 2 may also be applied to the skin by strapping, or by a combination of pre-straining and strapping.

Although the depicted wound treatment device 2 may have a generally rectangular configuration with a size of about 80 mm to about 40 mm, in other variations the device may have any of a variety of lengths and widths, and may comprise any of a variety of other shapes. Also, the corners of the device may be squared or rounded, for example. The lengths and/or widths of the device may be in the range of about 5 mm to about 1 meter or more, in some variations about 20 mm to about 500 mm, and in other variations about 30 mm to about 50 mm, and in still other variations about 50 mm to about 100 mm. In some variations, the ratio of the maximum dimension of the wound device (e.g. its length) to an orthogonal dimension to the maximum dimension (e.g., width), excluding the minimum dimension of the device (e.g. the thickness), may be in the range of about 1:1, about 2;1, about 3:1, about 4:1 about 5:1, about 6:1, about 7:1, about 8:1, about 9:1 or about 10:1 or greater. In some variations, the strain axis of the device in use may be oriented with respect to the maximum dimension or to the orthogonal dimension to the maximum dimension.

The elastic material of the device may comprise a single layer of material or multiple layers of the same or different materials. The material may have any of a variety of configurations, including a solid, foam, lattice, or woven configuration. The elastic material may be a biocompatible polymer, e.g., silicone. The thickness of polymer sheets, e.g., silicone polymer sheets or shape memory polymer sheets, may be selected to provide the devices or bandages with sufficient load carrying capacity to achieve desired recoverable strains, and to prevent undesired amounts of creep deformation of the bandages or devices over time. In some variations, the thickness across devices or bandages is not uniform, e.g., the thickness across the device may be varied to change the stiffness, the load carrying capacity, or recovery strains in selected orientations and/or locations. The elastic material may have a thickness in the range of about 50 microns to 1 mm or more, about 100 microns to about 500 microns, about 120 microns to about 300 microns, or in some variations about 200 microns to about 260 microns. In some examples, devices having an edge thickness of about 500 microns or less, 400 microns or less, or about 300 microns or less may exhibit less risk of skin separation from inadvertent lifting when inadvertently brushed against clothing or objects. In some variations, the devices or bandages are tapered near the edges to reduce thickness. A tapered edge may also ameliorate peak tensile forces acting on skin tissue adjacent to the adhesive edges of the wound treatment device. This may or may not reduce the risk of skin blistering or other tension-related skin trauma. In other variations, the edges of the devices or bandage may be thicker than the middle of the device or bandage. It is hypothesized that in some configurations, a thicker device or bandage edge may provide a relative inward shift of the location of the peak tensile forces acting near the device or bandage edge, compared to devices or bandages of uniform thickness.

The adhesive regions may comprise a pressure sensitive adhesive, e.g., polyacrylate-based, polyisobutylene-based, silicone-based pressure sensitive adhesives, and the like. The T-peel release force and blunt probe tack force of the adhesive may be measured by a standardized test method, such as ASTM D1876 and ASTMD2979 or other appropriate method. In some variations, the T-peel release force or blunt probe tack test value of the adhesive is configured to maintain loads of at least about 50 mPa/mm for at least about 24 hours, about 48 hours, about 72 hours, about 1 week, about 2 weeks, about 3 weeks, about 4 weeks or more. In other variations, the loads may be at least about 75 mPa/mm, about 100 mPa/mm, about 125 mPa/mm, or at least about 150 mPa/mm over the particular time period. The degree of adhesion (e.g. as measured by the T-peel release force or blunt probe tack test value) may vary depending upon the degree of strain placed onto the skin or incision site, and in some variations, these time periods may be based upon an average skin strain of about 10%, about 20%, about 30%, about 40%, or about 50% or more. In some variations, the adhesive may have a T-peel release force of at least about 150 kg/m, about 160 kg/m, about 170 kg/m, about 180 kg/m, about 190 kg/m, about 200 kg/m, about 210 kg/m, about 220 kg/m, about 230 kg/m, about 240 kg/m, about 250 kg/m, about 260 kg/m, about 270 kg/m, about 280 kg/m, about 290 kg/m, about 300 kg/m, about 310 kg/m, about 320 kg/m, about 330 kg/m, about 340 kg/m, about 350 kg/m, about 400 kg/m, about 450 kg/m, or at least about 500 kg/m or higher. In some further variations, the T-peel release force may be no greater than about 1000 kg/m, about 900 kg/m, about 800 kg/m, about 700 kg/m, about 600 kg/m, about 500 kg/m, about 400 kg/m or about 300 kg/m. The blunt probe tack test value of the adhesive may be at least about 0.50 kg, about 0.55 kg, about 0.60 kg, about 0.65 kg, about 0.70 kg or about 0.75 kg or higher, and may be no greater than about 1 kg, about 0.9 kg, about 0.8 kg, about 0.7 kg, or about 0.6 kg. The T-peel release force and blunt probe tack force may be measured by a standardized test method, such as ASTM D1876 and ASTMD2979 or other appropriate method. Other features or variations of the device are described in U.S. application Ser. No. 11/888,978, filed on Aug. 3, 2007, which was previously incorporated by reference. In some variations, the final compressive stress and strain imposed onto the skin by the elastic material 4 may be the result of the dynamic equilibrium between the tensile stress in the skin and the elastic material 4 of the wound treatment device 2.

The wound treatment device 2 may be configured to impose a skin strain in the range of about 10% to about 60% or more, in other configurations about 15% to about 50%, and in still other configurations, about 20% to about 30% or about 40%. To achieve the desired degree of skin strain, the wound treatment device 2 may be configured to undergo elastic tensile strain in the range of about 20% to about 80% or more, sometimes about 30% to about 60%, and other times about 40% to about 50% or about 60%. The device 2 may comprise any of a variety of elastic materials, including but not limited to silicones, styrenic block copolymers, natural rubbers, fluoroelastomers, perfluoroelastomers, polyether block amides, thermoplastic elastomers, thermoplastic polyurethane, polyisoprene, polybutadiene, and the like. The material may have a Shore A durometer in the range of about 20 to about 90, about 30 to about 80, about 50 to about 80, One example of the elastic material 4 is MED 82-5010-05 by NUSIL TECHNOLOGY LLC (Carpinteria, Calif.). Other examples of suitable materials are described in U.S. application Ser. No. 11/888,978, which was previously incorporated by reference in its entirety.

When the strained device 2 is applied to a skin location and allowed to at least partially recover to its base configuration, the recovery level or equilibrium level of strain in the device may be in the range of about 10% to about 60% or more, in other configurations about 15% to about 50%, and in still other configurations, about 20% to about 30% or about 40%. The ratio between the initial engineering tensile strain placed onto the device 2 before recovery and the resulting engineering compressive strain in the skin may vary depending upon the skin type and location, but in some examples, may be about 2:1. In other examples, the ratio may be in the range of about 4:1 to about 5:4, about 3:1 to about 5:3, or about 5:2 to about 2:1. These skin strain characteristics may be determined with respect to a reference position of the body or body part, e.g. anatomical position, to facilitate reproducible measurements. The particular degree of strain may be characterized as either an engineering strain or a true strain, but may or may not be calculated based upon or converted from the other type of strain (e.g. the strain may be based upon a 60% engineering strain that is converted to a true strain).

Referring to FIGS. 2A and 2B, the wound treatment device 2 may be provided with one or more release liners 52, 54 and 56 to protect one or more of the adhesive regions 20, 22, 48 and 50, The release liners 52, 54 and 56 may be configured with one or more flaps or tabs 58, 60, 62, 64, 66 and 68 that project from the edges 10, 12 or surfaces 6, 8 of the treatment device 2 to facilitate grasping or removal of the release liners 52, 54 and 56. FIG. 2C depicts the liners 52, 54 and 56 without the wound treatment device 2. In some examples, the release liners may resist inadvertent adhesion of the wound treatment device to itself or other surfaces during loading of the device onto an applicator, or during application of the device to the skin. In variations where the device has multiple separate adhesive regions, separate release liners may be provided for each region, or some regions may be covered by the same release liner. Referring back to FIGS. 2A and 2B, the three release liners 52, 54 and 56 are provided to cover the four adhesive regions 20, 22, 48 and 50, with two end release liners 52 and 54 covering the flap regions 49 and 51, respectively and a single release liner 56 covering both inner adhesive regions 20, 22. The end release liners 52 and 54 each comprise two tabs 58 and 60 which project from the same edge 10 and 12, respectively, of the device, but in other variations, one or more tabs may project from the other edges 14 and/or 16, from multiple edges, or from no edges. The central release liner 56, for example, comprises tabs 66 and 68 that project from opposing edges 10 and 12 of the device. Although the tabs 58, 60, 62 and 64 are depicted as aligned with the edges 14 and 15 of the treatment device 2, in other variations the liners may be configured with tabs at other locations, or with a different number of tabs. In some variations, the tabs may also be folded or creased, which may facilitate grasping where the tabs are located against a surface rather than projecting from an edge.

In variations comprising multiple release liners, the liners may or may not be removed at different times or in a particular order. In some variations the liners may include indicia to facilitate removal in a particular order. The indicia may comprise alpha-numeric characters 70 and 72, color, graphic symbols and the like, and may be located on the body of the liner or on the tabs, if any. In FIGS. 2A and 2B, for example, users may be instructed to remove the central liner 56 during the loading of the treatment device 2 onto an applicator and/or for application to a skin site. After the initial adherence of the treatment device 2 to the skin, the outer release liners 52 and 54 covering the flap regions 49 and 51 may then be removed to permit adherence of the rest of the treatment device 2.

The release liners may comprise any of a variety of materials, including both opaque and transparent materials. The release liners may comprise Mylar or paper, or any other material with reduced adhesion to the adhesive material(s) of the device. In some examples, the central liner 56 (or a different liner) may be reapplied to the inner adhesive regions 20 and 22 after the treatment device 2 is loaded onto an applicator, which may protect the adhesive materials until actual application to the skin. The liners may comprise different surface geometries, e.g. surface roughness, and/or indicia that may permit identification of the original liner surface that was applied to the adhesive regions, which may reduce degradation of the adhesive regions from dust, dander and/or other substances if the incorrect side of the liner is reapplied to the device.

As noted previously, an applicator, tensioning device and/or straining device may be provided in some embodiments to impart a strain to a skin treatment device with an external force and/or to maintain a strain imparted to the skin treatment device. In some examples, the straining device may be configured to impart and/or maintain a single predetermined or pre-set strain or a plurality of predetermined or pre-set strains. Features described herein with respect to an applicator may also be used in any tensioning or straining device that is used to strain a skin treatment device. An applicator, tensioning or straining device that is described as being in an unstrained configuration is in a configuration in which a skin treatment device may be unstrained or relatively less strained when attached to the applicator, tensioning or straining device. An applicator, tensioning, or straining device that is described herein has being in a strained configuration is in a configuration in which a skin treatment device may be strained or relatively more strained when attached to the applicator, tensioning or straining device. Features described herein with respect to an applicator may also be used in any tensioning or straining device that is used to strain a skin treatment device.

A skin treatment device that is described herein is a device that may be applied, attached to or coupled to one or more layers of the skin of a subject and may include without be limited to, a wound treatment device, a dressing, bandage, or other device.

Attachment structures of an applicator, tensioning or straining device may include any structures that are used to attach or couple an applicator, tension or straining device to a skin treatment device. Such devices may include but are not limited to pockets and tabs, hook and loop mechanism, hooks, angled bars, adhesives, removable adhesives, pegs, rip cords, towel bar configurations, sliding pins, friction locks, cam locks, vacuum or suction devices, snap connectors, carpet tack, press fit connections or other connections.

The attachment structure profile may be straight, curved or otherwise varied. For example, the shape of the attachment structures may be configured to follow the shape of the area of the subject's body to which the skin treatment device is to be attached. A tensioning device or applicator may be selected or configured to have a profile that has a desirable profile for a particular body location or profile where the skin treatment device is to be placed on a subject's skin. A tensioning device or applicator may be selected or configured to closely match a portion of a subject's body profile. The attachment structures may be curved, curvable, bendable, deformable, shapeable or movable to provide alternative shapes or profiles of an attached skin treatment device.

Attachment features or structures of a skin treatment device may include any of the attachment structures or corresponding structures to the attachment structures.

Attachment structures and corresponding attachment features may be configured to provide multi direction strain or additional strain in an orthogonal direction.

In some variations the applicator may comprise a mechanism configured to facilitate separation, release, removal or detachment of the attachment structures of the applicator from the attachment features of the skin treatment device, including but not limited to the separation devices and methods described herein. Releasing mechanisms may include but are not limited to pivoting, rolling, rocking or sliding features associated with or coupled to attachment structures of the applicator. They may be self-releasing latches or spring members. They may be actuated when a pressure member is applied to a skin treatment device prior to removing the applicator. They may be manually actuated. The mechanisms may include levers, latches, locking members, spring members, for example.

A variety of locking, latching or detent mechanisms may be used to maintain the applicator in a various configurations including but not limited to unstrained, partially strained, strained, unstamped, or stamped configurations. A variety of locking, latching or detent mechanisms may be used to maintain a skin treatment device in a variety of configurations including unstrained, partially strained, strained. By locking an applicator in a strained position a predetermined strain of a given skin treatment device may be achieved. Other locking mechanisms, including but not limited to other locking mechanisms described herein may be used. A variable locking mechanism may be used to vary the amount of strain for a given skin treatment device. Such mechanisms may be releasable to permit straining, stamping, release of the attachment structures from the skin treatment device, or to release various structures to permit reloading of the device.

An actuator, actuation force may be used or applied at any point during straining of a skin treatment device and is externally applied to the applicator, either manually or otherwise. Optionally, an actuator or handle may be provided that provides a mechanical advantage greater than 1 at least at some point when actuated. Optionally a mechanical advantage may increase as a device is strained.

Applicators configured with any of a variety of force transfer mechanisms may be used to transfer forces exerted onto the applicator to the skin treatment device, including but not limited to leaf springs, helical springs, pneumatic or hydraulic struts, sliders, helically threaded shafts, articulated linkages, pivoting levers, and the like. The force transfer mechanisms may be configured to transfer the resulting force onto the skin treatment device along the same direction as the originally exerted force, or in other configurations along a different direction.

Applicators described herein may provide accessible areas or spaces to access areas where the skin treatment device is applied to the skin so that the adhesive may be pressed on to the skin. The adhesive used may be, for example, a pressure activated adhesive (PSA), as a silicone, acrylic, styrene block copolymer, vinyl ether, nitrile or other PSA. In other variations, a non-pressure sensitive adhesive may be used, including but not limited a heat or light-cured adhesive.

In some variations, the applicator may comprise an attachment configuration that facilitates attachment of a device to the applicator, and a delivery configuration that stretches or strains the attached device by about 20%, about 30%, about 40%, about 50%, about 60%, about 70%, about 80%, about 90%, about 100%, or about 110% or more, relative to its unstretched or unstrained configuration. The applicator may have a greater strain in the attachment configuration than in the delivery configuration. The applicator may be configured such that the strain it imposes generally falls within with a one or two-sided tolerance of about 2%, about 3%, about 4%, about 5%, about 6%, about 7%, about 8%, about 9%, about 10%, about 15%, or about 20%, for example. The load per width imposed by the applicator onto the treatment device along its axis of tensile strain may vary, depending upon the amount of desired strain and the material characteristics of the device. For example, the applicator may be configured to exert a engineering strain of about 60% to the device using a load per millimeter width that is in the range of about 0.1 N to about 1 N, about 0.2 N to about 0.8 N, about 0.3 N to about 0.6 N, or sometimes in the range of about 0.4 N to about 0.5 N or 0.6 N. In another example, the applicator may be configured to exert a strain of about 40% to the device using a load per millimeter width that is in the range of about 0.05 N to about 0.6 N, about 0.1 N to about 0.5 N, about 0.2 N to about 0.4 N, or about 0.3 N to about 0.4 N. In still another example, the applicator may be configured to exert a strain of about 30% to the device using a load per millimeter width that is in the range of about 0.05 N to about 0.5 N, about 0.1 N to about 0.3 N, or about 0.2 N to about 0.3 N.

The applicator may also be characterized by the force required to compressively strain the applicator to a particular strain level, and/or by the force the applicator exerts when the applicator is compressed to a particular strain level. For example, the applicator may be configured to be compressively strained to about 40% using a load per millimeter width (or dimension transverse to the direction of strain) that may be at least about 0.1 N, about 0.2 N, about 0.3 N, about 0.4 N, about 0.5 N, about 0.6 N, about 0.7 N, or about 0.8 N or greater. In other examples, the applicator may be configured to be compressively strain to about 20% using a load per millimeter width (or transverse dimension) that is at least about 0.05 N, about 0.1 N, about 0.2 N, about 0.3 N, about 0.4 N, about 0.5 N or greater. In some variations where the material exhibits little hysteresis on it stress/strain curves, the loading force and the unloading force at a particular level of strain may be the same or similar.

FIGS. 3A to 4D depict one example of an applicator 100 that may be used to generate the strain and/or maintain strain in the device for application to a treatment site. The applicator may comprise a resilient elastic or spring body comprising an expanded or relaxed configuration (as shown in FIGS. 3A to 3D) and a retracted or constrained configuration (as shown in FIGS. 4A to 4D). The applicator 100 may comprise an elastic body 102 with first and second device attachment structures 104 and 106 that are configured to releasably engage the applicator attachment structure 40 and 42 of the treatment device 2 illustrated in FIGS. 1A to 2B. Here, the attachment structures 104 and 106 comprise a plurality of projections 108 and 110 that may be inserted into the openings 44 and 46 of the devices. The projections may have any of a variety of shapes, orientations, sizes or thicknesses. In this particular variation, the projections 108 and 110 are angled upwards from the base structures 112 and 114 of the applicator 100 (e.g. away from an attached device). The angle may be anywhere in the range of about 0 degrees to about 90 degrees or more, in some variations about 15 degrees to about 75 degrees, and in other variations about 25 degrees to about 45 degrees. The angles of the projections 108 and 110 may be uniform or non-uniform between the two sets or between individual projections. The shape of the projections may be square, rectangular, triangular, bulbous, mushroom-like, or the like. In some variations, the transverse dimension of the projections may be greater than the corresponding transverse dimension of the openings 44 and 46 of the treatment device 2, which may result in stretching or deformation of the openings 44 and 46 when attached to the applicator 100. The resistance from the deformation of the openings 44 and 46 may reduce the rate of inadvertent detachment of the treatment device 2 from the applicator 100. In variations comprising a mushroom or bulbous configuration, the rounded distal end of the projection may reduce the risk of damaging the device during loading, while the increased transverse dimension of the projection distally and the reduced transverse dimension of the projection proximally may provide tactile feedback to the user during loading that may indicate proper loading, and may also reduce the risk of device damage by reducing stretching of the openings once loaded. The projections may have a length of about 500 microns to about 5 mm or more, in some variations about 1 mm to about 4 mm, and in other variations about 2 mm to about 3 mm. The thickness of the projections may be the same, lower or greater than the elastic body 102 of the applicator 100. The elastic body 102 may comprise any of a variety of elastic materials, including but not limited to polymeric and metallic materials. In other variations, generally malleable polymeric or metallic materials may be used.

To facilitate the application of pressure against the device 2 and onto the skin, the base structures 112 and 114 may further comprise pressure pads 116 and 118 or other padded/deformable structures that may conform to the contours of the skin surface, which may redistribute forces exerted onto the treatment device 2 through the applicator 100 across the surfaces of the pads 116 and 118. The pressure pads 116 and 118 may comprise any of a variety of deformable materials, including foams (open and closed cells), gels, and the like.

In some variations, the device may comprise further indicia that may be used to indicate proper loading and/or straining of the device. In FIGS. 1A and 2A, for example, the geometry of lines 74 and 76 may be remain generally linear when all of the openings 40 and 42 of the treatment device 2 are engaged by the projections 108 and 110, but may be deformed or become non-linear if one or more of the openings 40 and 42 are missed, due to variations in the degree of stretching across the treatment device 2. The lines 74 and 76 may also align with corresponding indicia on the applicator 100 (e.g. the base structures 112 and 114 and/or the pressure pads 116 and 118) to indicate proper loading and/or stretching of the treatment device 2.

In some variations, the applicators may be manually maintained in a retracted state by the user during loading by squeezing or otherwise exerting compressive forces onto the applicator. In other variations, as shown in FIGS. 3A to 4D, the applicator 100 may comprise a locking mechanism 120 that may be used to maintain the applicator 100 in one or more configurations. In this particular variation, the locking mechanism 120 comprises a latch 122 that releasably engages a tab 124 located in an opening 126 or recess of the elastic body 102. The latch 122 may be biased against the tab 124 such that as the tab 124 slides along the length of the latch 122 as the elastic body 102 is compressed, until the tab 124 engages a tab opening 134 (depicted in FIGS. 4A, 4C and 4D) on the latch 122 and locks in the compressed configuration of the elastic body 102. To resist complete disengagement between the latch 122 and the opening 126 in the elastic body 102, the opening 126 may comprise a retention bar 128 that the distal section 130 of the latch 122 may be wrapped around. The latch 122 may be attached to the elastic body 102 by a rivet 132, or by welding or gluing, for example. In other examples, the latch may be integrally formed by laser cutting or punching out the latch structure from the elastic body. In some variations, the applicator may be configured with two or more latches.

In other variations, the latch may not be biased against the tab and may be manually engaged the user at the desired locking position. In other variations, the latch may have a plurality of tab openings to permit locking into a variety of configurations. In still other variations, the latch may comprise a projection or tab that engages an opening or recess of the elastic body. In alternate variations, the locking mechanism may comprise a ratchet mechanism, locking pin mechanism, or resistance screw, for example.

Figure 5A:
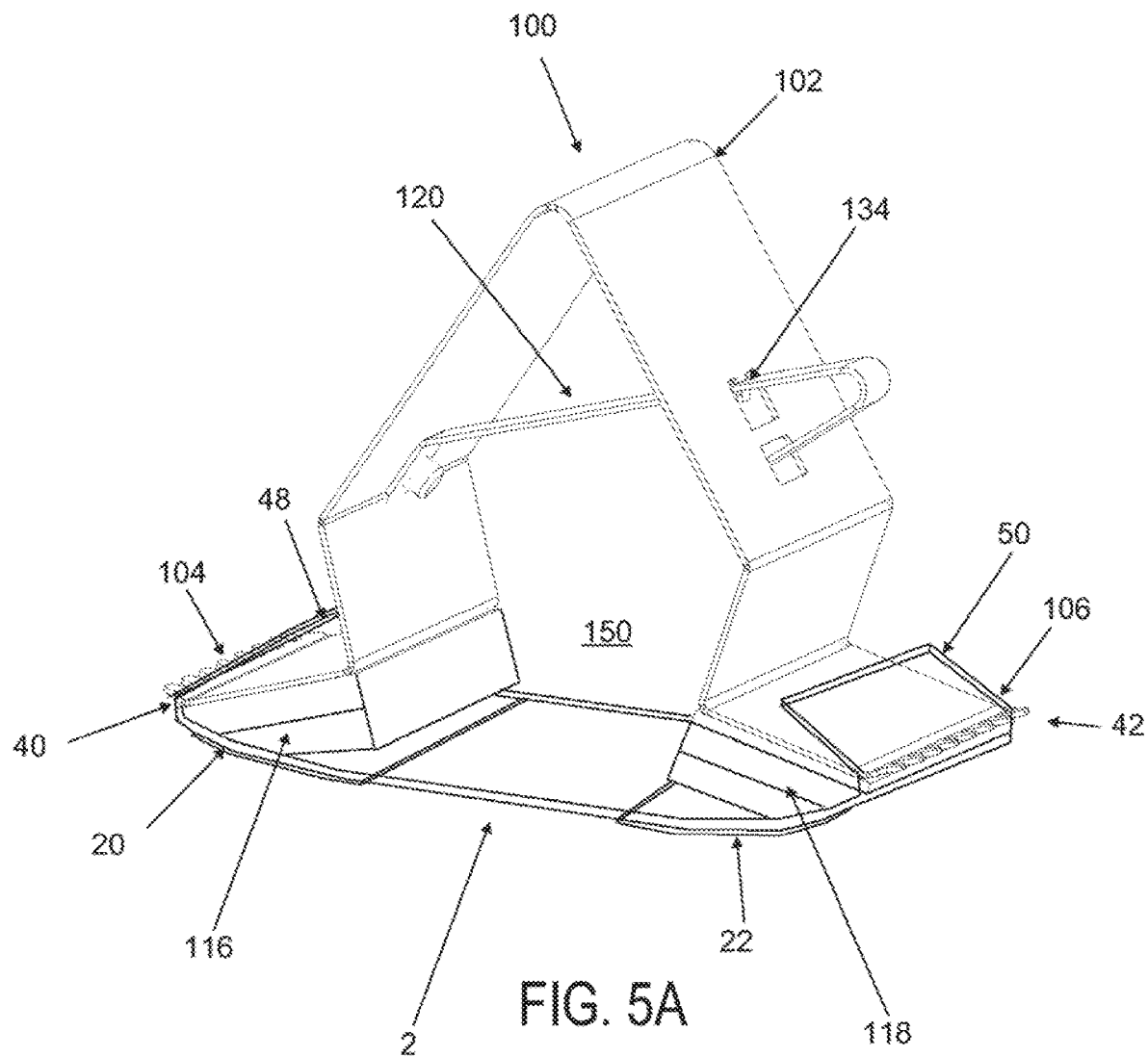
FIGS. 5A and 5B are schematic perspective and side elevational views of the applicator in FIGS. 4A and 4B loaded with a wound treatment device.
Figure 5B:
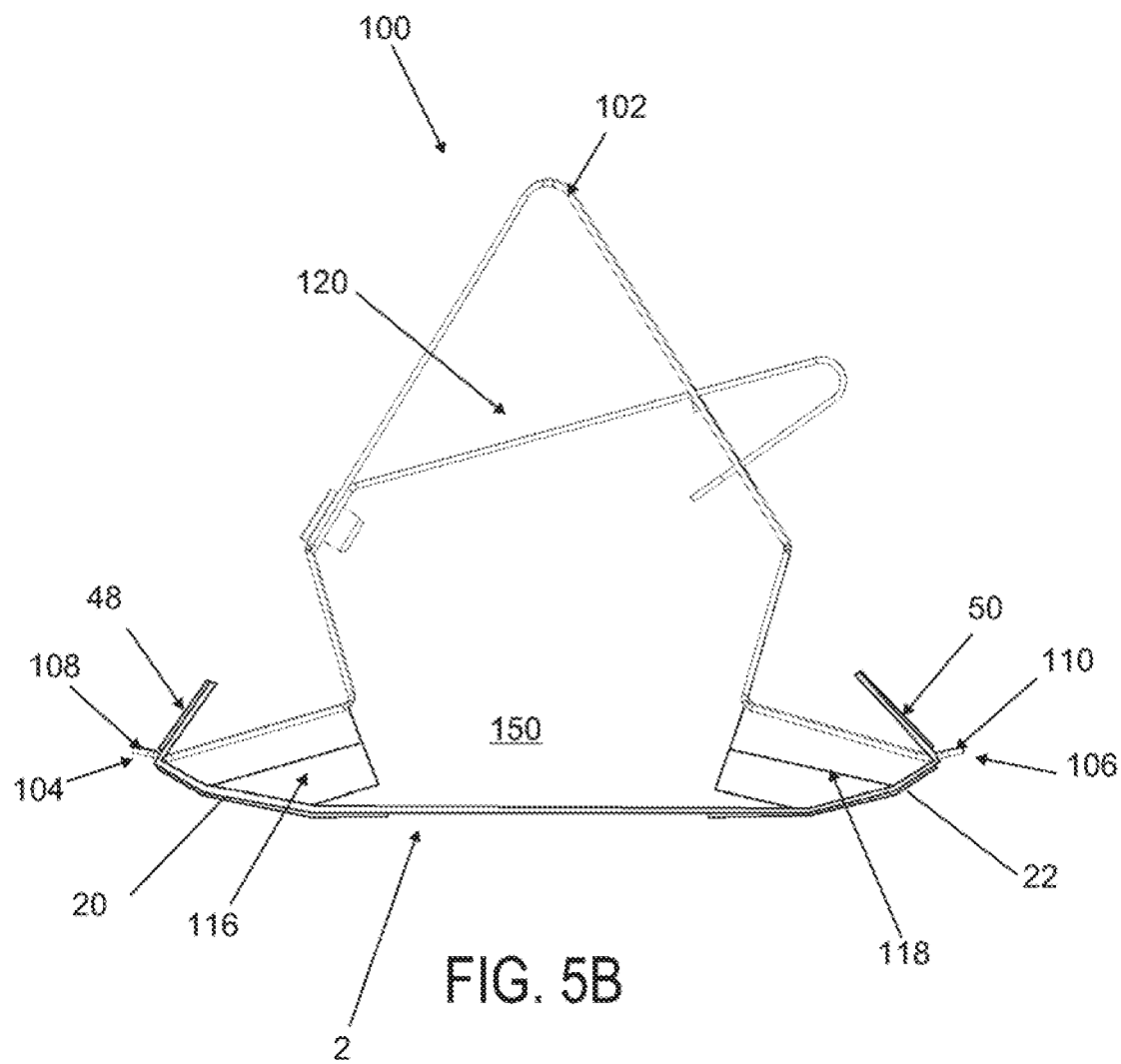

FIGS. 3A to 3D depict the applicator 100 in its base configuration with reduced strain, if any. To facilitate loading of the treatment device 2, the applicator 100 may be compressed, until the applicator 100 is locked into a compressed configuration, as illustrated in FIGS. 4A to 4D, which may reduce the degree of stretching, if any, needed to load the device onto the applicator 100, as depicted in FIGS. 5A and 5B. Once the device is loaded, the locking mechanism 120 may be disengaged by pressing the latch 122 away from the locking tab 124. The potential energy in the elastic body 102 from its compression is then released to permit stretching of the attached treatment device 2 and is ready for adhesion to the skin. As shown, the elastic body 102 comprises a sheet of semi-rigid material, but in other variations, may have a frame-like configuration. In some variations, the elastic body, may comprise stainless steel with a thickness in the range of about 500 microns to about 3 mm or more, in some variations about 1 mm to about 2 mm, and in other variations about 1 min to about 1.5 mm. The elastic body 102 may be configured with as a number of angled panel regions, as depicted in FIGS. 3A to 4D, with generally horizontal base structures 112 and 114 that may be generally orthogonal to side panels 140 and 142, which in turn form an angle of about 135 degrees each (as measured from the inferior surface of the elastic body 102) with the central panels 144 and 146 which in turn may be generally oriented at about a 90 degree angle with each other. The angles between the panels may be sharp angles or rounded angles, and may be configured differently depending upon the particular skin site (e.g. limb vs. torso), or degree of desired strain (e.g. a more obtuse angle between the central panels 144 and 146). In other variations, the angle between any two panels or base structure may be in the range of about 0 to about 360 degrees, in some variations about 45 to about 135 degrees, and in other variations about 75 to about 90 degrees (as measured from the underside or topside of the elastic body 102). The latch mechanism 120 may be attached or involve the central panels as shown in FIGS. 3A to 4D, but in other variations may be attached or involve the side panels or base structures. In other variations, the elastic body may comprise a curved structure, including but not limited to an omega-shaped structure. As illustrated in FIGS. 3A to 5B, the non-planar configuration of the applicator 100 provides an open region 150 between the pressure pads 116 and 118 and side panels 140 and 142, which permits access to the superior surface of an attached device to facilitate positioning of the device to a treatment site and/or to permit direct access or the application of pressure to the central portion of a device by the user (e.g. using fingers or other instrument). As shown in FIGS. 5A and 5B, the treatment device 2 and the applicator 100 may be configured so that the inner adhesive regions 20 and 22 are generally located underneath the pressure pads 20 and 22 when the treatment device 2 is loaded onto the applicator 100.

Various applicators and/or tensioning devices may be used to pre-tension and apply the wound devices 2300, 2310 for the application of uni-axial, bi-axial (or other multi-axial) compressive force to the treatment site are described. For example, applicators and/or tensioning devices described in U.S. patent application Ser. No. 12/854,859 (including, for example, the multi-axial device in FIG. 54A-54E) and U.S. Pat. No. 7,683,234 (including, for example, the multi-axial devices in FIGS. 8A-B, 9A-B) may be used to apply multi-axial compression wound devices. U.S. patent application Ser. No. 12/854,859 and U.S. Pat. No. 7,683,234 are both hereby incorporated by reference in their entirety.

In some variations, the use of two opposing and collapsible walls to separate to slidable walls of a fixed configuration, as illustrated in the applicator depicted in FIGS. 13A to 13I, for example, may provide a mechanical advantage when applying a strain to a skin treatment device. A mechanical advantage may be characterized by an output force that is greater than the input force, and may be described as a ratio of the output force divided by the input force that is greater than 1. In some variations, the mechanical advantage may be at least about 1.1, about 1.2, about 1.3, about 1.4, about 1.5 about 1.7, or about 2 or more. The mechanical advantage may or may not be provided throughout the entire movement range of the applicator.

FIGS. 13A to 13D illustrate another variation of a tensioning device, straining device or an applicator 1200. The applicator 1200 comprises a handle 1201 or actuator configured to be actuated to strain a skin treatment device 1240 and/or to apply the device to the skin of a subject. The applicator 1200 includes end attachment structures 1206, 1207. In some variations, the applicator may also include side attachment structures 1203, 1204, 1220, 1222 that may interface with structures 1203 and 1204 be attached to the sides of a skin treatment device. This interface may provide a second dimension or axis to the tension or strain applied to the skin treatment device. Thus the skin treatment device may be strained in orthogonal directions or at least two directions, i.e., the applicator provides a bi-directionally or multi-directionally strained skin treatment device. The attachment structures may be located on the bottom of bump features 1245 on wall segments 1220, 1222. The attachment structures 1206, 1207 may comprise engagement flaps having edges that engage attachment features 1246, 1247 of a corresponding skin treatment device 1240. Attachment structures 1203, 1204 as shown are hook or loop structures that have corresponding hook or loop structure attachment features on the back side of the skin treatment device. The applicator or skin treatment device attachment structures may comprise other types of attachment structures, including but not limited to other attachment structures described or set forth herein.

The applicator 1200 may further comprise moveable, slidable or a collapsing or expanding bottom frame structure 1202, opposing fixed configuration walls 1208, 1209 and opposing movable, pivotable or hinged walls 1210, 1211. Frame structure comprises a pair of slidable elements 1220, 1221 and pair of slidable elements 1222, 1223. Each of the pair of slidable elements 1220, 1221 and 1222, 1223 can slide together into a closed position (FIGS. 13A and 13C) where there is a first distance d1 between walls 1208 and 1209. The pairs of slidable element 1220, 1221 and 1222, 1223 can slide apart into a second open or strained position where there is a second distance d2 between the walls 1208, 1209 and where the distance d2 is greater than the distance d1 (as depicted in FIGS. 13B and 13A, respectively).

Hinged wall 1210 comprises first and second wall portions or segments 1212a, 1213a that are movably, pivotally or hingedly connected to each other by connector 1214a, at a pivot point. Hinged wall 1211 comprises a first and second wall segments 1212b, 1213b that are movably, pivotally or hingedly connected to each other by connector 1214b at a pivot point. Wall segments 1212a and 1213b are movably, pivotally or hingedly coupled respectively to opposite end sides 1208a, 1208b of wall 11081208. Wall segments 1212b and 1213a are movably, pivotally or hingedly coupled respectively to opposite end sides 1209b, 1209a of wall 1209. The walls 1208, 1209, 1210, 1211 are coupled to the frame structure 1202 to form a box-like structure with an opening (when in the strained configuration) to provide access to a skin treatment device 1240 attached across the bottom of the applicator to attachment structures 1203, 1204, 1206, 1207, 1246, 1247. This access allows a user to apply pressure to a skin treatment device as or after it is applied to a skin surface, before removing the applicator 1200 from the skin treatment device. Alternatively, a pressure application device may be coupled to the applicator and actuable to provide pressure through the opening to a skin treatment device as or after it is being applied.

Figure 13A:
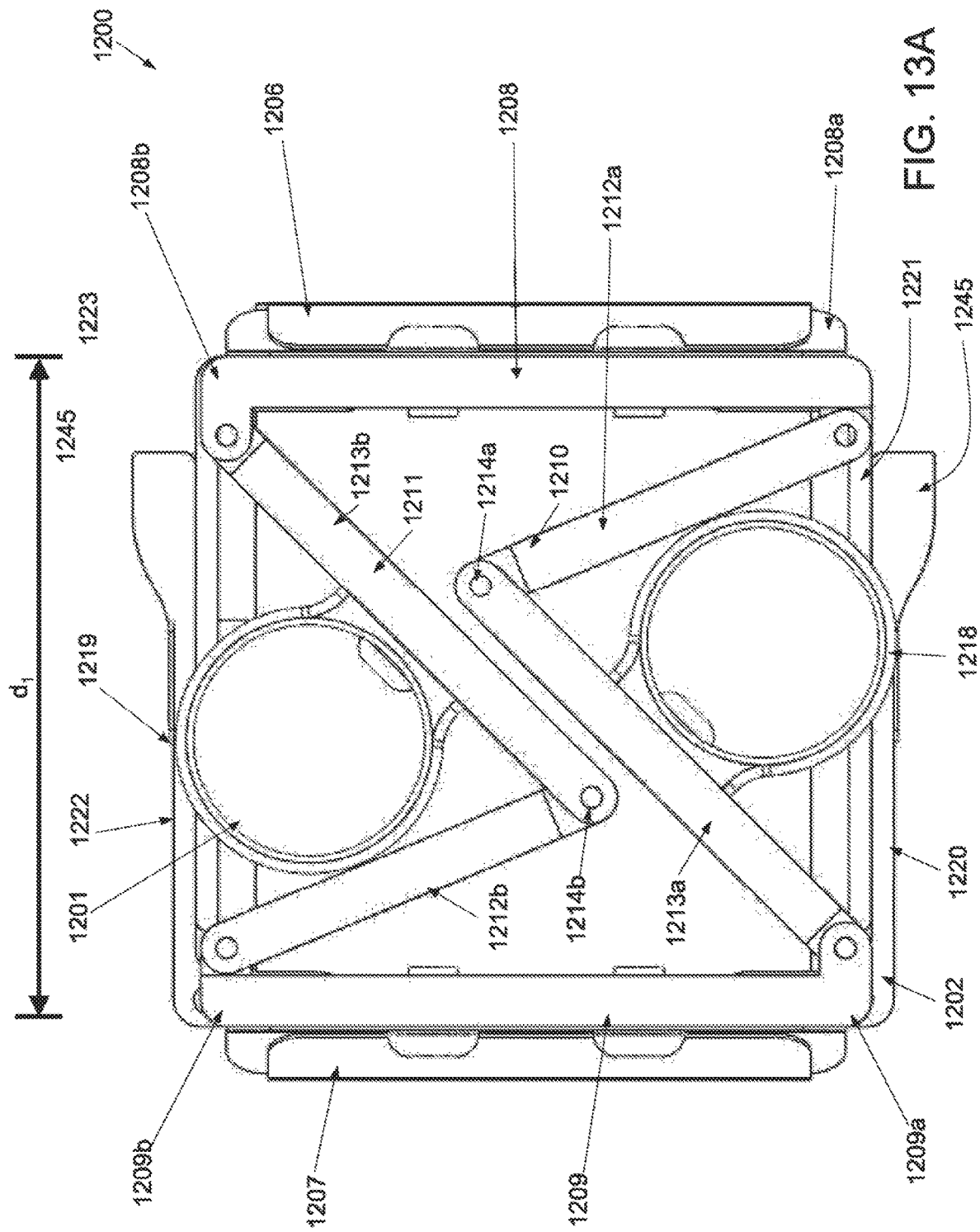
FIG. 13A is a superior view of an applicator in an unstrained configuration.
Figure 13B:
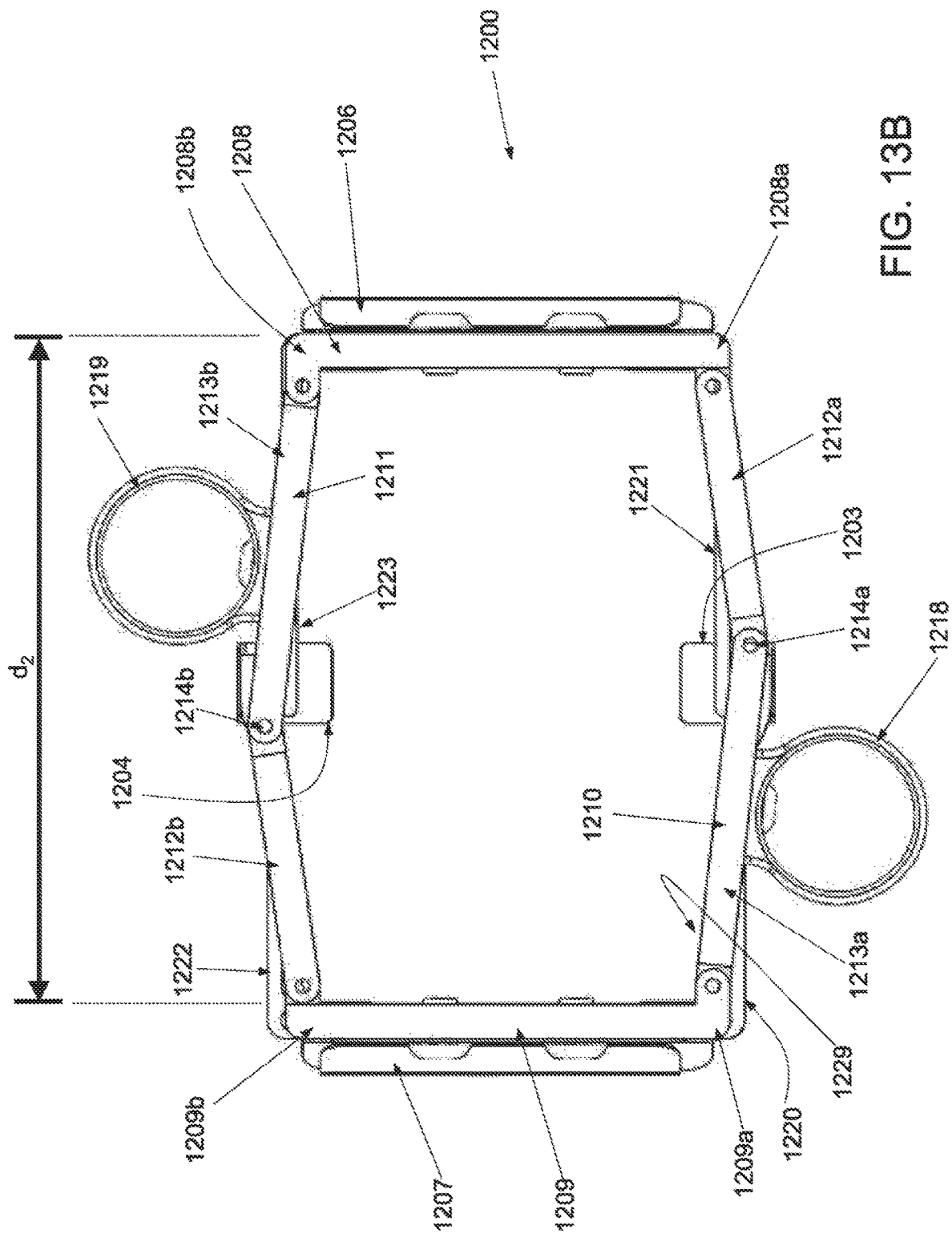
FIG. 13B is a superior view of the applicator of FIG. 13A in a strained configuration.
Figure 13C:
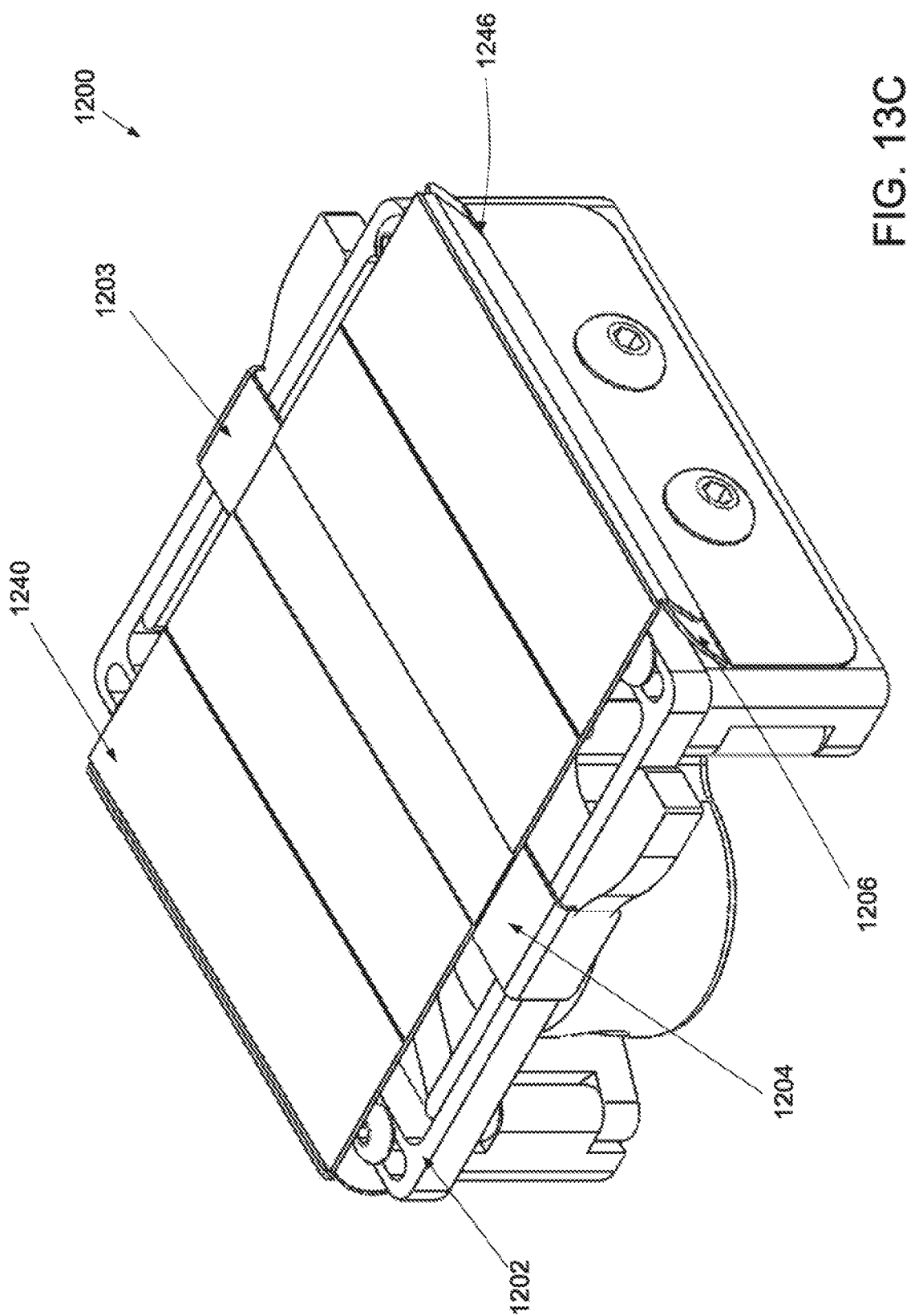
FIG. 13C is an inferior perspective view of the applicator of FIG. 134 in an unstrained configuration.

FIGS. 13A and 13C illustrate the applicator 1200 in a first, unstrained position. The frame structure 1202 is in an unstrained position where slidable elements 1220, 1221 and slidable elements 1222, 1223 are in a closed position. Wall segments 1212a and 1213a are pivoted to form a v-shape collapsed into the box structure of the applicator 1200, and opposing wall segments 1212b and 1213b are pivoted to form a v-shape collapsed into the box so that the distance between end walls is a distance d1. This position facilitates loading of an unstrained skin treatment device onto the applicator 1200.

After an unstrained device is loaded, the skin treatment device is strained by applying opposing, outward forces to pulling rings 1218, 1219, respectively attached to wall segments 1213a, 1213b. This force straightens side walls 1210, 1211 and pairs of sliding elements 1220, 1221 and 1222, 1223 into an elongated or open position as shown in FIGS. 54B and 54D, thus transferring a separation force to the skin treatment device to strain the skin treatment device widthwise (relative to its orientation and use on along a length of an incision). In other variations, a single collapsible wall attached generally about the midpoints of the fixed configuration walls so only a single pulling force is used to separate the fixed configuration walls.

Figure 13D:
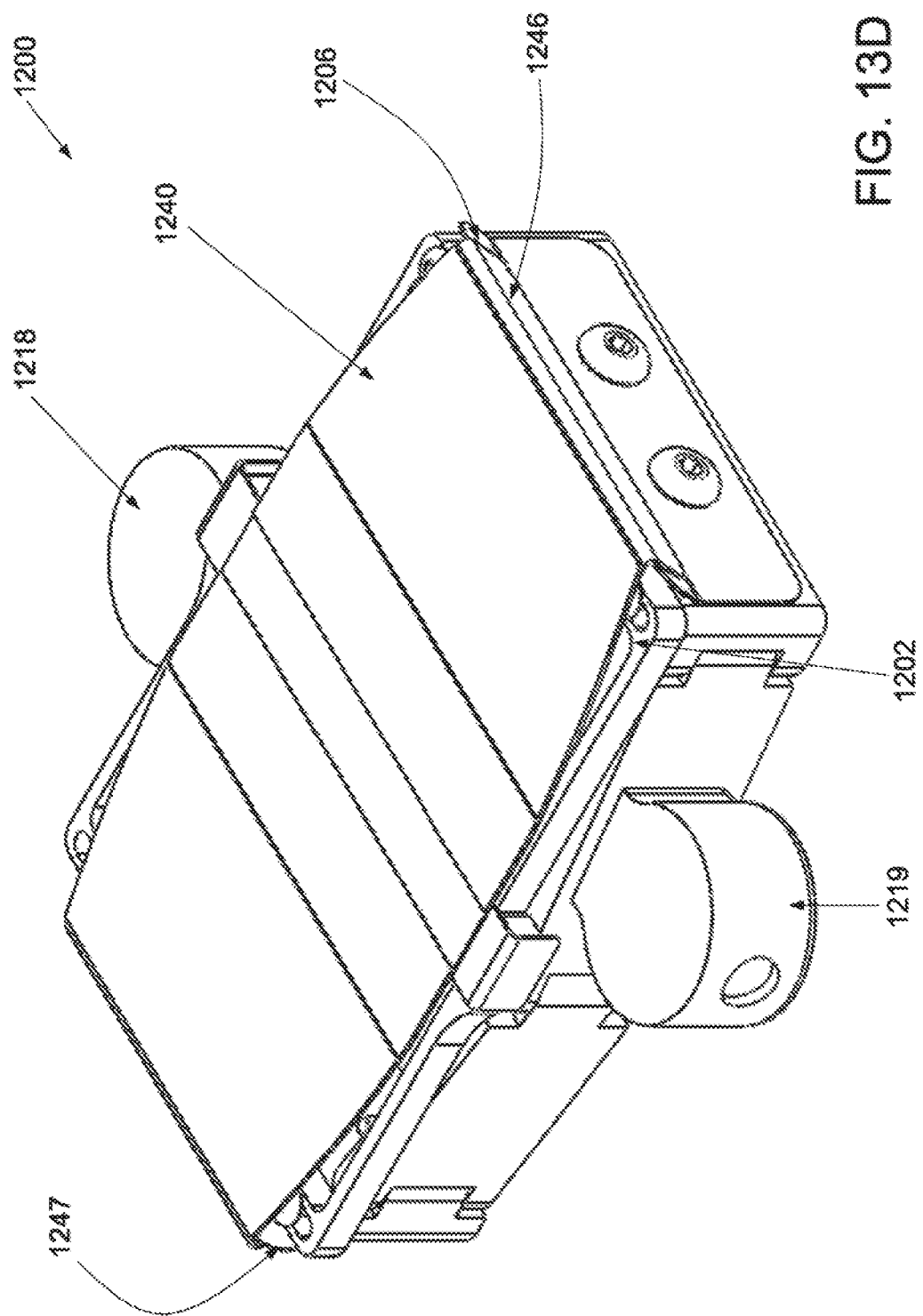
FIG. 13D is an inferior perspective view of the applicator of FIG. 13A in a strained configuration.

When the device is in the strained position as shown in FIGS. 13B, and 13D the wall segments 1212a, 1213a and 1212b, 1213b of walls 1210 and 1211 are pivoted. As shown in FIGS. 13B and 13D, the side walls are over center or slightly hyper-extended or pivoted outward to provide a strain in a width wise direction with the force transferred to the skin treatment device through attachment structures 1203, 1204. Thus the skin treatment device may be strained in orthogonal directions or at least two directions, i.e., the applicator provides a bi-directionally or multi-directionally strained skin treatment device. The applicator 1100 may be locked or maintained in a strained configuration by way of over center side walls. A latch or other stop such as a spring loaded pin may engage one or more of inside surfaces of wall segments 1212a, 1213a, and 1212h, 1213b to maintain the applicator in its over center locked position.

Figure 13E:
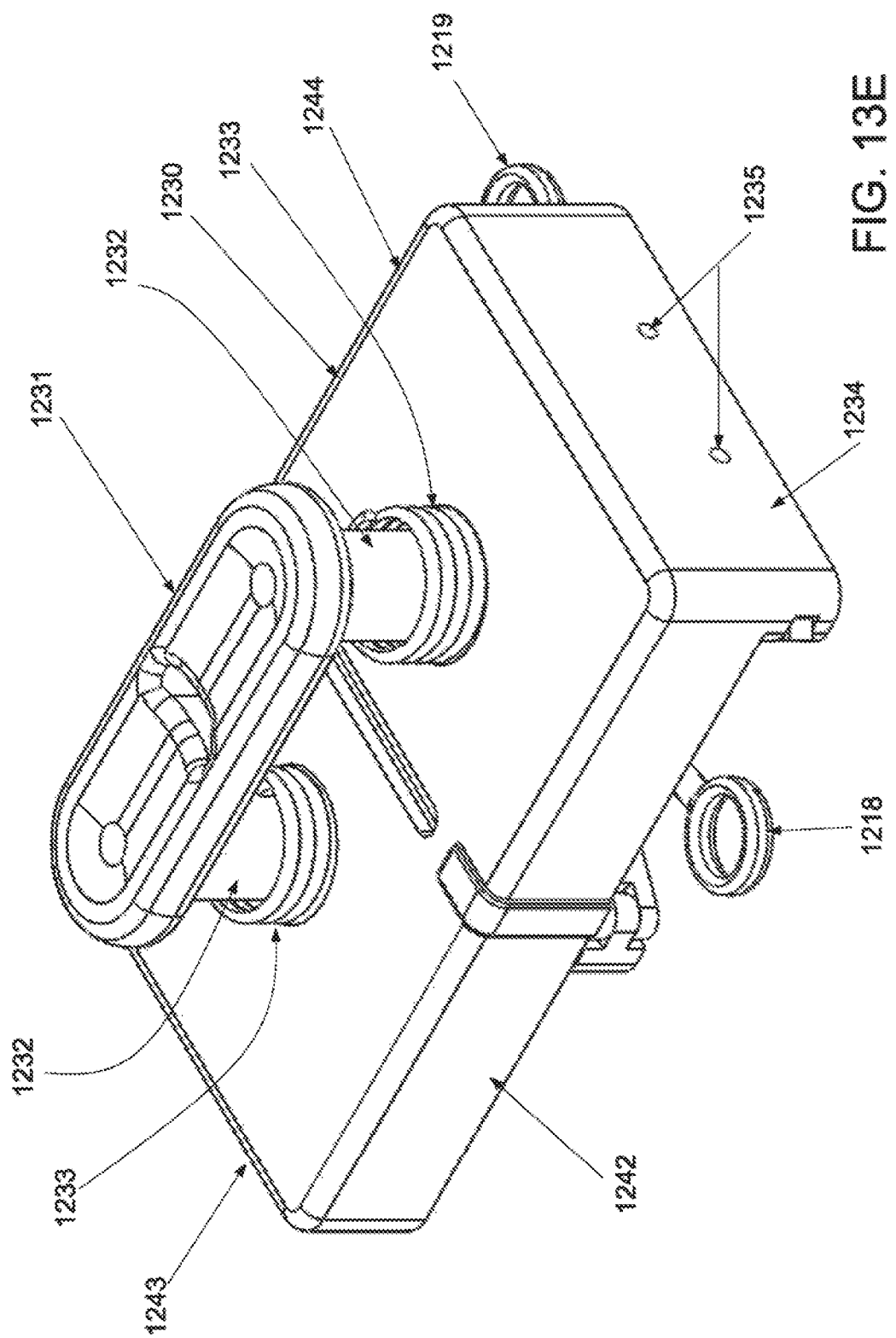
FIG. 13E is a perspective view of the applicator with integrated stamper, in an unstrained configuration.
Figure 13F:
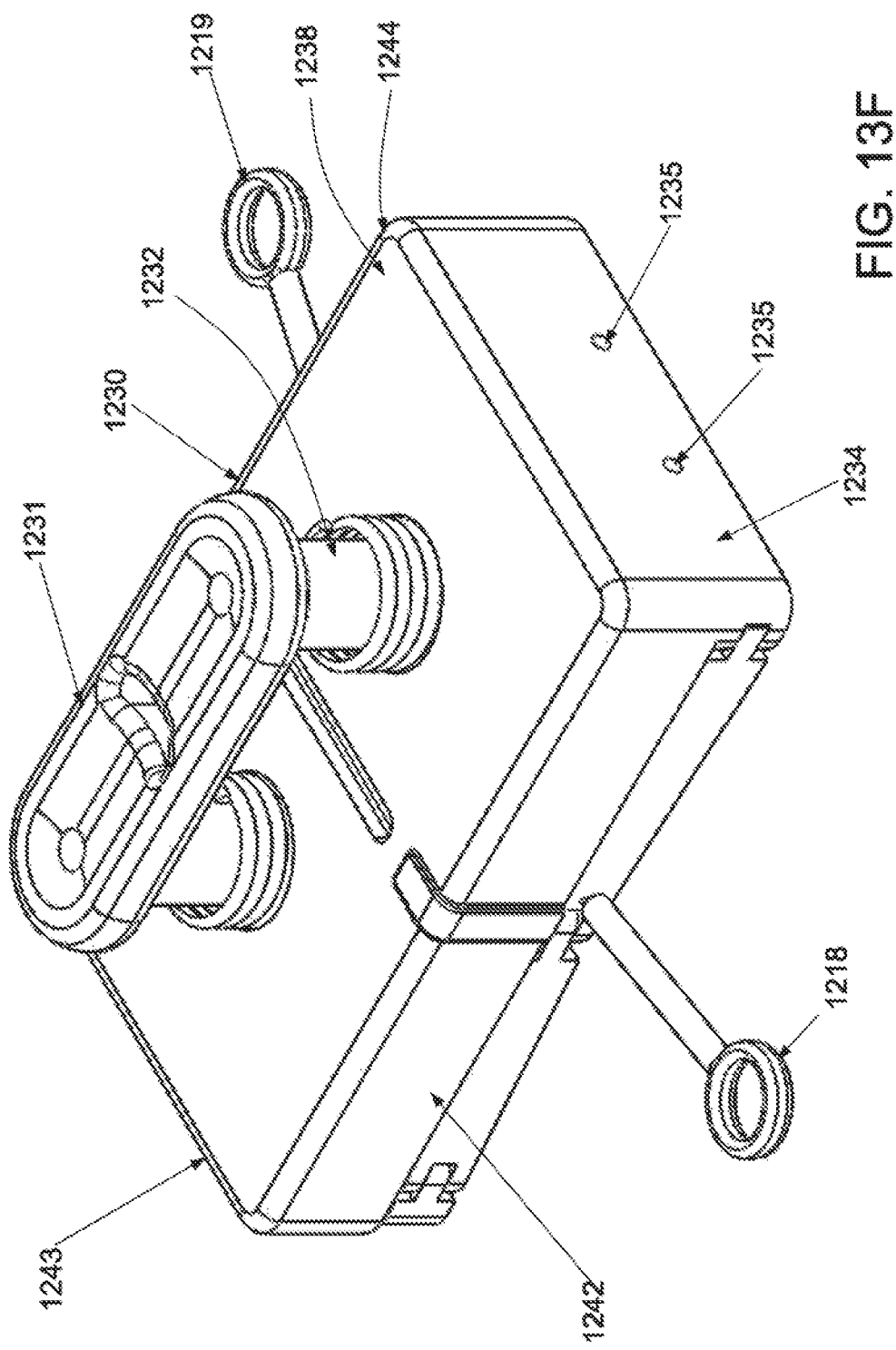
FIG. 13F is a perspective view of the applicator of FIG. 13E in a strained configuration.
Figure 13G:
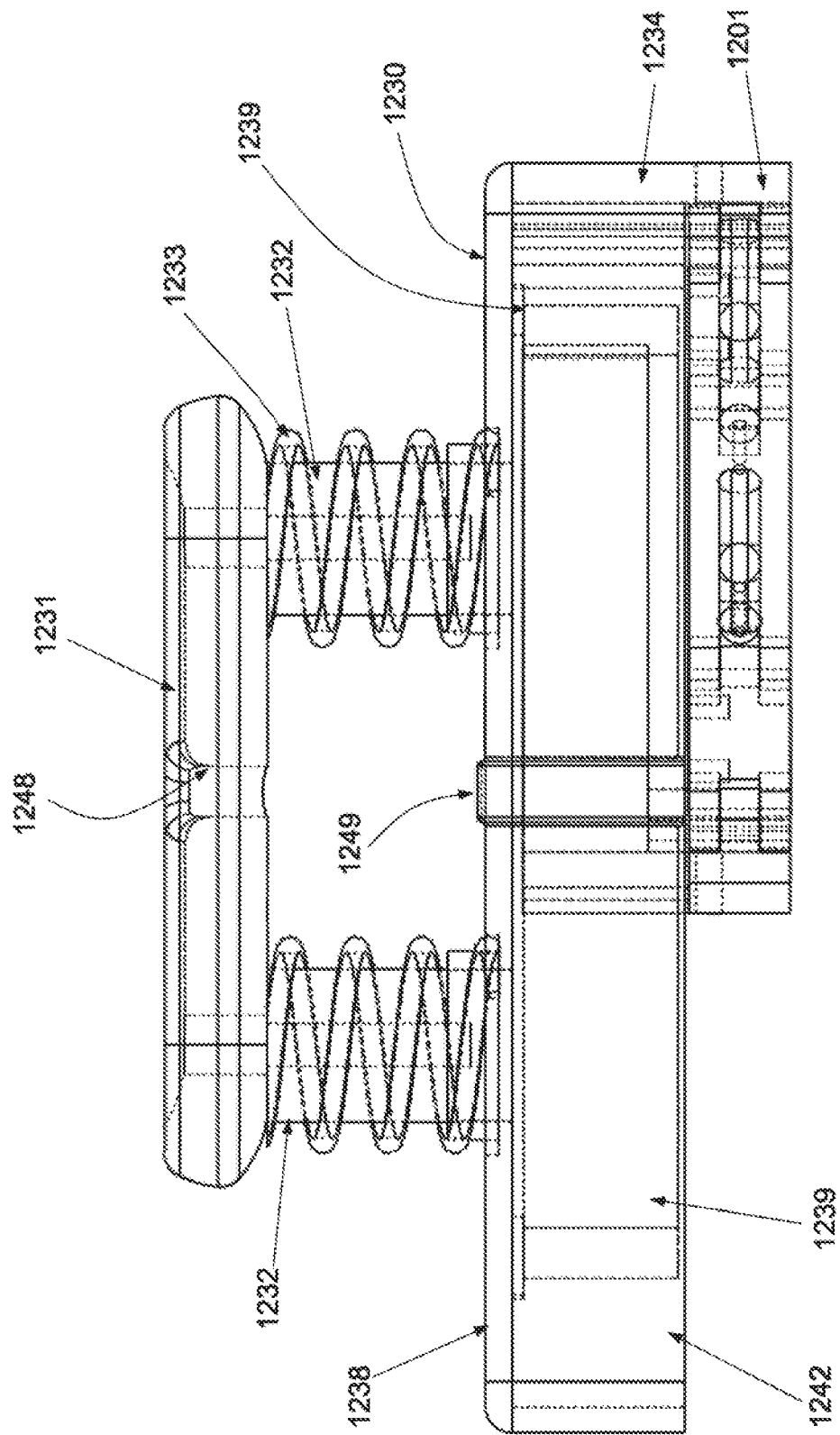
FIG. 13G is a side view of the applicator of FIG. 13E in an unstrained configuration.
Figure 13H:
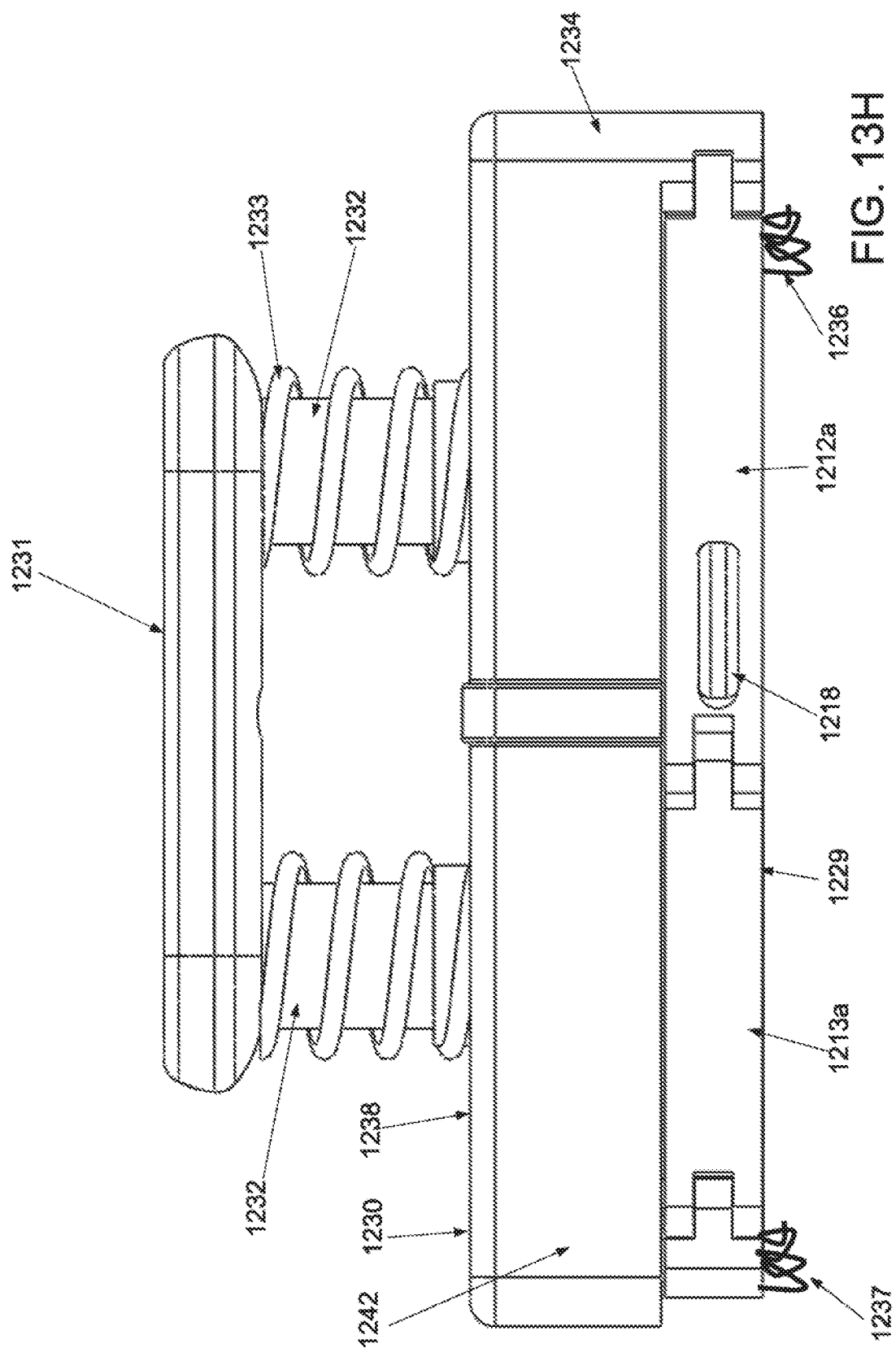
FIG. 13H is a side view of the applicator of FIG. 13E in a strained configuration.
Figure 13I:
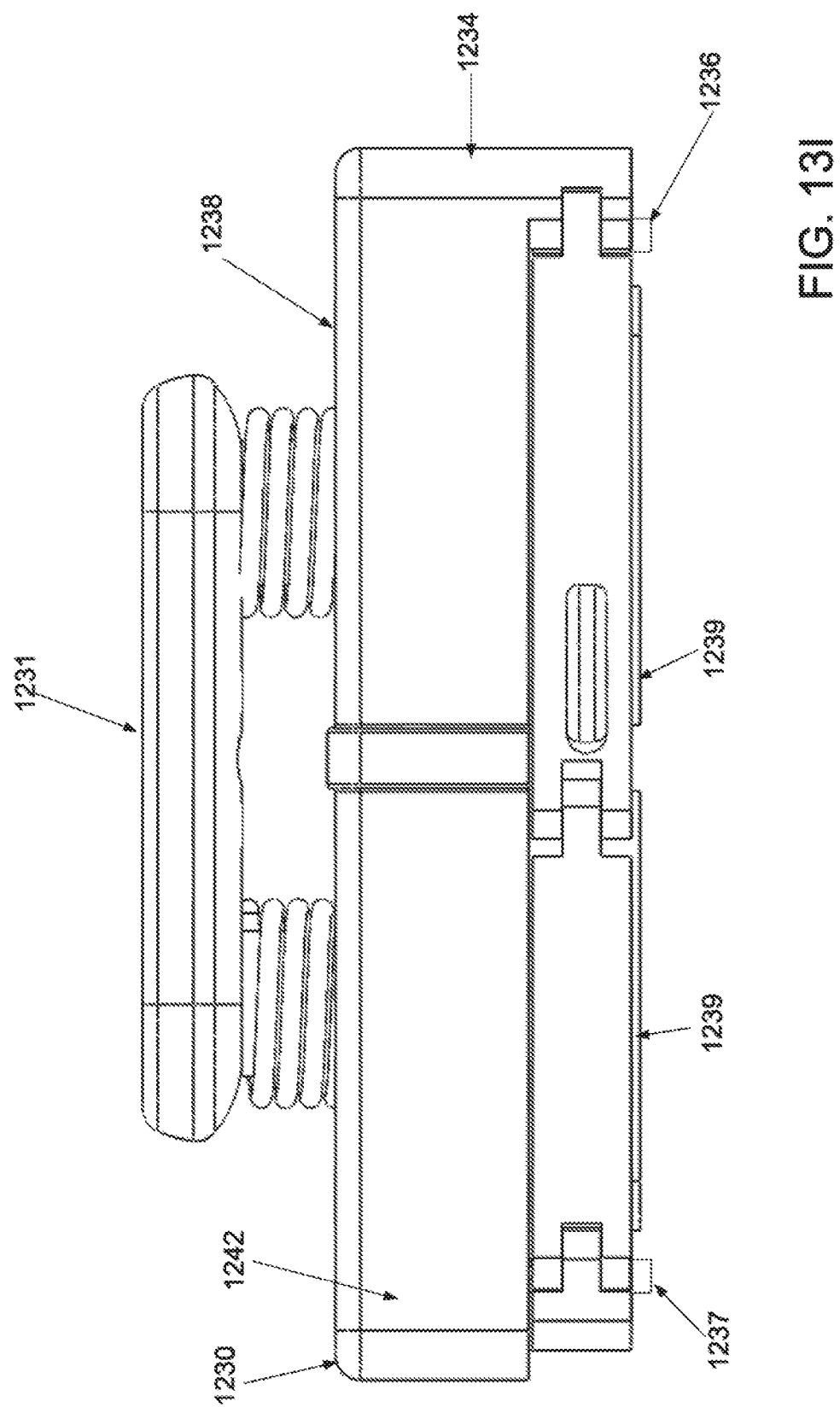
FIG. 13I is a side view of the applicator of FIG. 13E in a strained configuration with a deployed stamper.

FIGS. 13E to 13I illustrate other variations of a tensioning device, straining device or an applicator 1200 as previously described with respect to FIGS. 13A to 13D, including an integrated stamper 1230. The stamper 1230 is attached to the top of the handle, actuator or tensioning device 1201 of FIG. 13A with connectors 1235 that attach the device 1201 to the inside of the stamper side wall 1234. The stamper comprises a handle 1231 coupled to posts 1232 that extend through the top wall 1238 of the stamper 1230. Posts 1232 are coupled to pressure members 1239 inside the stamper 1230. Prior to actuation, the pressure members 1239 are positioned within walls 1234, 1242, 1243, 1244 of stamper 1230 above and the tensioning device 1201 as shown in FIG. 13G. Springs 1233 around the posts 1232 bias the handle 1231 in an upward (not stamping) configuration. Visibility openings 1248, 1249 respectively in the handle 1231 and the top wall 1238 of the stamper 1230 provide an opening through which the skin treatment device and/or wound can be seen, for positioning of the applicator 1200 in an appropriate location.

As shown in FIGS. 13E, and 13G, when the tensioning device 1201 is in an unstrained configuration, the length of its side walls 1210, 1211 are less than the length of the side walls 1242, 1244 of the stamper 1230.

In FIGS. 13F and 1311, the tensioning device 1201 is in a strained configuration where the side walls 1242, 1244 of the stamper 1230 are approximately that of the side walls 1210, 1211 of the tensioning device 1201. In a strained configuration, an opening 1229 is provided in the tensioning device 1201 sized to receive the pressure members 1239 therethrough. When a force is applied to the handle 1231 and the tensioning device 1201 is in a strained configuration, the pressure members 1239 extend down into and through the opening 1229 in the applicator handle 1201, towards the skin treatment device (not shown), to apply a force to areas of the dressing where an adhesive interfaces the skin of the subject. (FIG. 13I) Thus, where the adhesive is pressure activated, the stamper 1230 applies a generally even pressure to the skin treatment device. All stampers described herein may be constructed of a foam or other compressible, conformable material which translates the force applied to handle 1231 to the skin treatment device (not shown). These other materials include silicones and styrenic block copolymers (e.g. KRATON®), in a solid or porous form.

As an option or alternative, the applicator 1200 may be provided with attachment structures 1236, 1237 that comprise a hook or loop structure of a hook and loop attachment mechanism, or any other attachment structure described herein. Likewise, side attachment structures 1203, 1204 may also be a hook or loop structure or any other attachment structure.

Figure 14A:
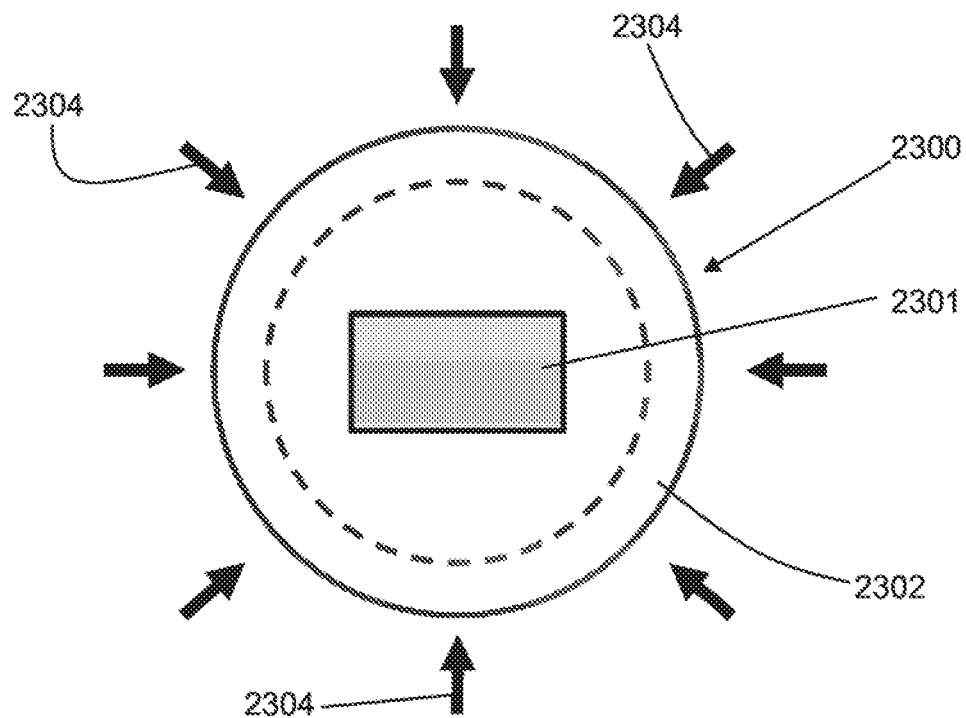
FIG. 14A is a schematic of one variation of a circular dressing.
Figure 14B:
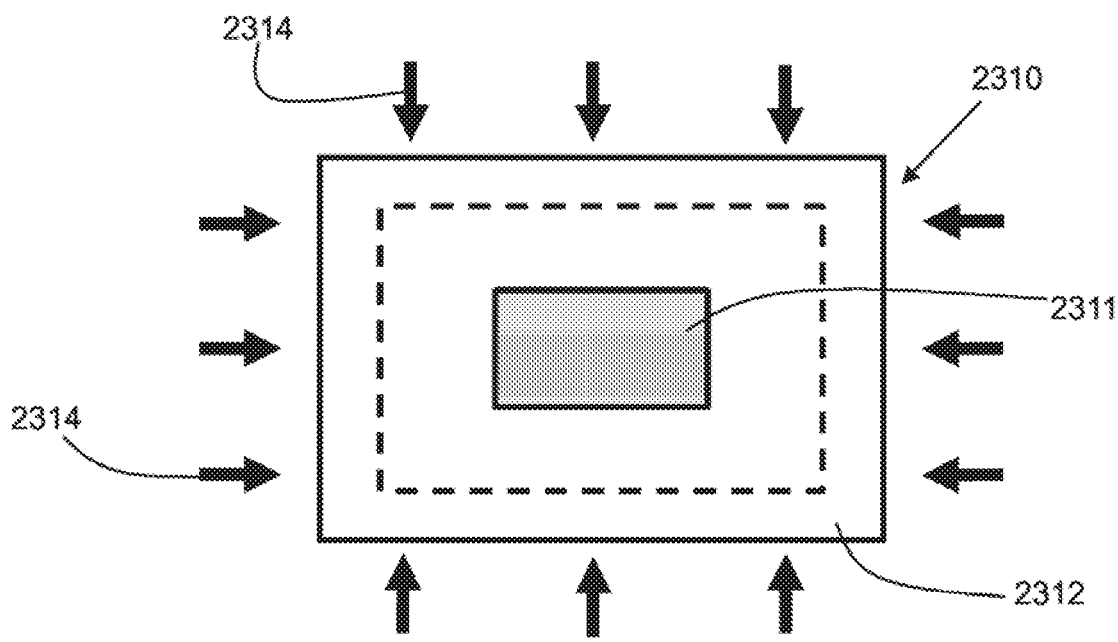
FIG. 14B is a schematic of one variation of a rectangular dressing.

As indicated previously, such assemblies and devices may also be used to treat skin grafts (including split-thickness and full-thickness grafts, xenografts, cadaveric graft, autologous grafts), skin flaps and skin substitutes, with or without the use of biomaterials or biodressings, either on top and/or below the graft/flap/substitute, or otherwise in a treatment site. In some embodiments, these assemblies and devices may be configured to apply a wound device that applies a uni-axial or bi-axial (or other multi-axial) compressive force to a treatment site. In some variations, the axes of the straining force(s) acting upon the dressing via the applicator, or the compressive forces acting upon the tissue via the dressing, may be oriented such the dressing and/or applicator has or exerts a first directly applied force (i.e. not a subcomponent force derived from one or more applied forces, or a summation force from two or more other directly applied forces) and a second directly applied force that is not aligned, parallel or orthogonal to the first directly applied force. These forces may be further characterized as being orthogonal to the orientations of the edge intersected by that force. The magnitudes of the straining force(s) directly applied by the applicator to the dressing along each axis may be uniform or non-uniform. Nominally, when the applicator is released from the dressing, the a portion of of the multi-axial forces is transferred to the treatment site along each nominal axis. The amount of stress or strain applied by the wound device may be pre-determined, as described above. For example, a circular pre-tensioned wound device 2300 may be applied over a treatment site with a skin graft, flap or substitute 2301, as schematically illustrated in FIG. 14A. In some variations, a circular pre-tensioned wound device may be applied over a wound or pre-closed (e.g., sutured) wound of a treatment site. The adhesive perimeter 2302 of the wound device 2300 may circumscribe the skin graft 2301, and may help ensure that compression is applied all around the skin region with the skin graft 2301. The wound device 2300 may be configured to apply radially inward compressive forces (represented by arrows 2304) after it is adhered to the skin and the tension is released. FIG. 14B depicts one variation of a rectangular wound device 2310 that applies hi-axial compressive forces (represented by arrows 2314) when applied to a skin region with a skin graft 2311. As with the circular wound device 2300, the rectangular wound device 2310 may have an adhesive perimeter 2312. While circular and rectangular shaped wound devices are depicted and described, it should be understood that wound devices may have any desired shape (e.g., oval, triangle, trapezoid, square, any polygon, kidney-shaped, or irregularly shaped, etc.) and in some variations, may be shaped to accommodate the specific anatomical contours of the treatment site or custom-shaped to fit a particular wound of a particular individual.

Referring to FIGS. 15A to 15E, a tensioning device or radially tensioning device 3000 is illustrated that may be used to apply a radial strain to a circular, curved or arced portion of a dressing geometry by applying a radially tensioning or straining force continuously or at different points defining or along a curved or arced portion, perimeter, or edge of the dressing. The tensioning device may be used to evenly distribute strain radially across a rounded dressing. According to variations, an applied multi-axial strain may or may not be relatively uniform in a radial direction from a center point of an arc, curve or circle of a dressing.

A tensioning member 3000 comprises a straining structure 3006 and a frame 3001. The straining structure 3006 comprises a handle portion 3007 and a plunger portion 3008. The frame 3001 comprises a support element 3002 having an opening 3003 configured to receive the plunger portion 3008 of the straining structure 3006, which is configured to fit within and extend through the opening 3003 of the frame 3001. At least a portion of a cross section of the opening 3003 has an arced, curved or circular shape which may be matched by the shape of the plunger portion 3008.

A dressing assembly 3010 comprises a dressing 3011 removably coupled to an attachment sheet or attachment ring 3012. Prior to straining the dressing 3011, the attachment sheet or ring 3012 of the dressing assembly 3010 may be attached via an attachment structure 3013 to the frame 3001 over the circumference of the opening 3003 of the frame 3001. The attachment structure 3013 may include or be coupled to the attachment sheet or ring 3012. As shown in FIG. 15D the attachment sheet or ring 3012 may be attached to the frame 3001 by way of an adhesive 3014 such as an acrylic adhesive (e.g., 3M™ adhesive 9475LE).

The attachment structure or structures 3013 are positioned or located in a circular, arced or curved configuration about the attachment ring 3012 so that the tensioning forces applied to the dressing assembly 3010 and dressing 3011 may applied radially with respect to the circular, arced or curved shape.

In some variations the attachment structures may comprise one or more mechanisms or elements configured to facilitate separation, release, removal or detachment of the dressing from the applicator or tensioning device, other attachment elements, or other portions of the dressing assembly, including but not limited to the separation devices and methods described herein. Release elements or releasable attachment structures may include but are not limited to pockets and tabs, hook and loop mechanism, hooks, angled bars, pivoting, rolling, rocking or sliding features associated with or coupled to attachment structures, adhesives, removable adhesives, adhesive tapes or other adhesive devices, pegs, rip cords, towel bar configurations, sliding pins, friction locks, cam locks, vacuum or suction devices, snap connectors, carpet tack, press fit connections or other connections, levers, latches, locking members, spring members, for example, or other mechanisms such as cutters or rip cords or other structures or features to facilitate tearing, cutting or separation of attachment structures or elements perforated or otherwise severable structures, that permit removal of dressing from the applicator, other portions of the dressing assembly and/or attachment structures, features, elements or portions. They may be self-releasing latches or spring members. They may be actuated when a pressure member is applied to a skin treatment device prior to removing the applicator. They may be manually actuated.

Figure 15A:
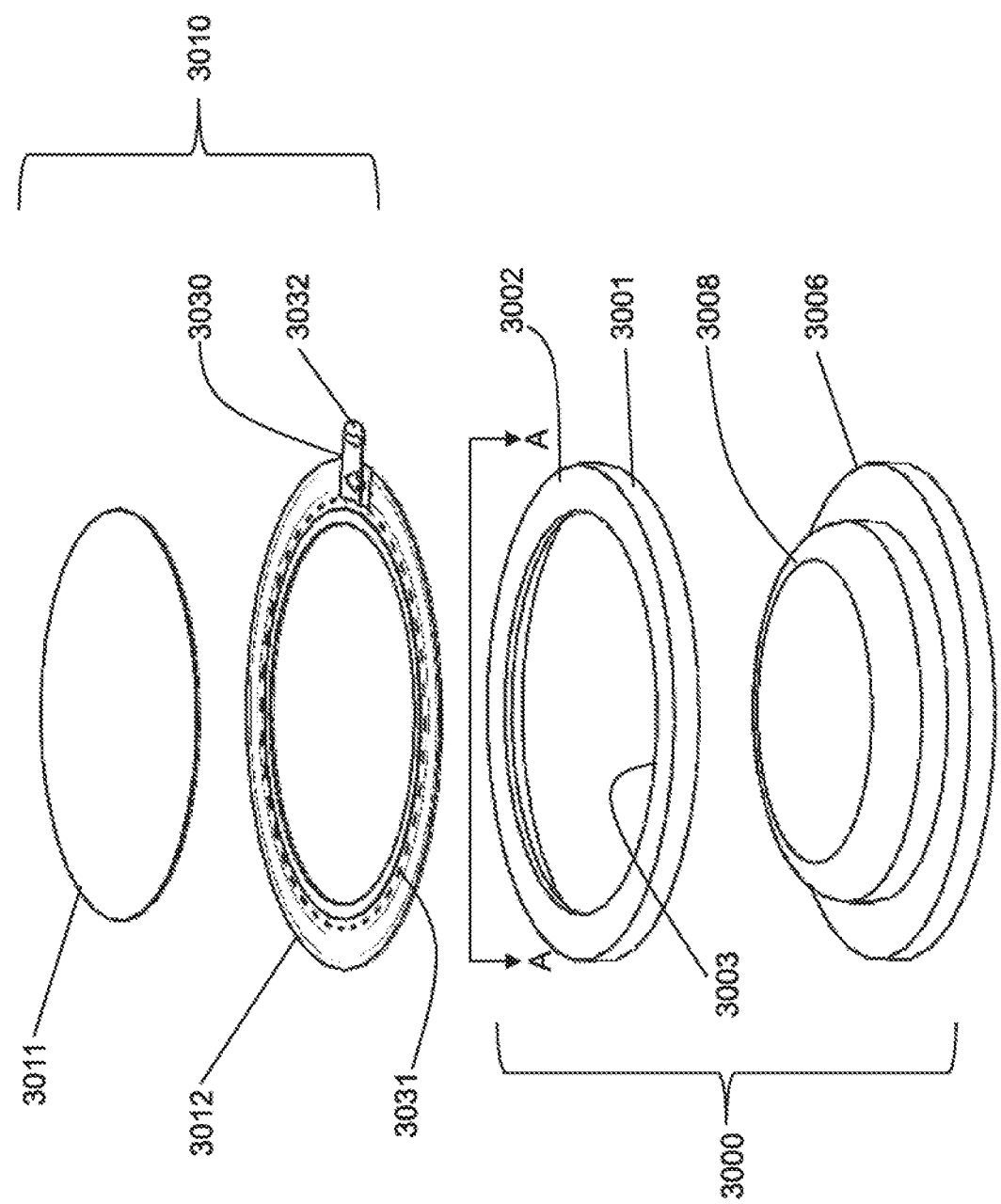
FIG. 15A is an exploded perspective view in a first direction of a tensioning device and dressing assembly.
Figure 15B:
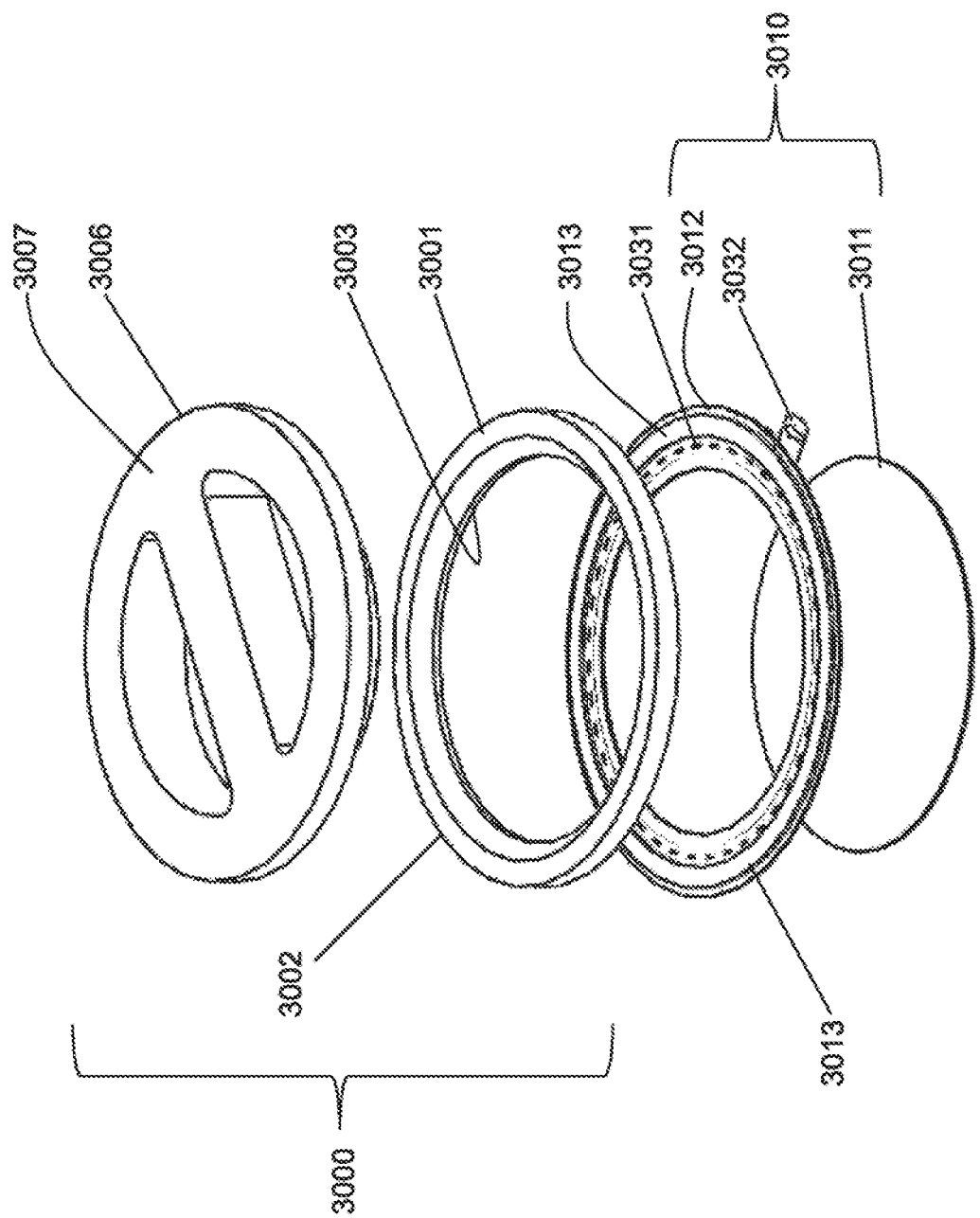
FIG. 15B is an exploded perspective view in an opposite direction of the tensioning device and dressing assembly of FIG. 15A.
Figure 15C:
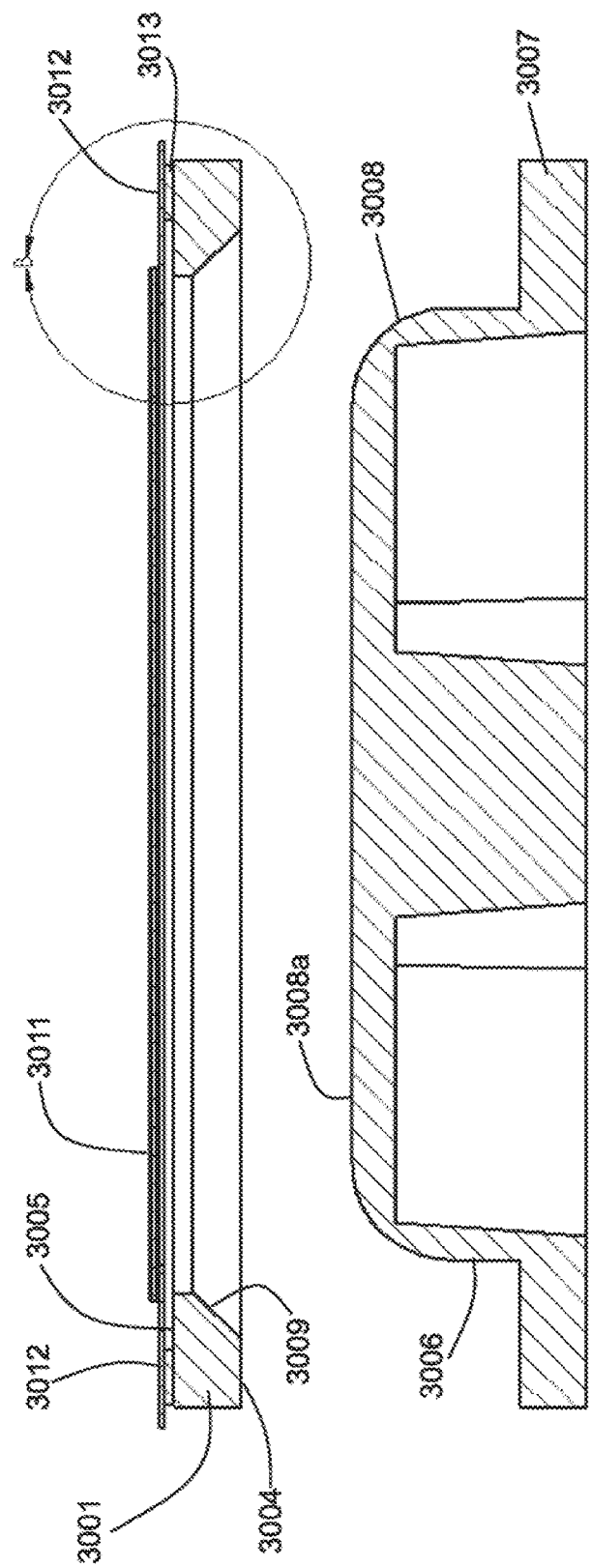
FIG. 15C is a cross-sectional view of a strain plunger of the tensioning device and an assembled dressing assembly and frame of FIG. 15A along the lines A-A.
Figure 15D:
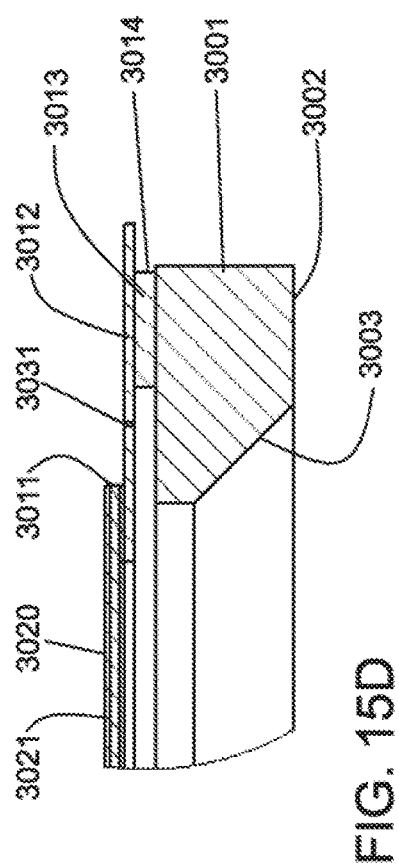
FIG. 15D is a detailed view of section B of FIG. 15C.

In FIG. 15C, the straining structure 3006 is shown just prior to straining positioned, and facing the open side 3004 of the frame 3001 with the dressing assembly 3010 attached to an opposing dressing side 3005 of the frame 3001. At the dressing side 3005, the opening 3003 of the frame 3001 has a relatively larger diameter that matches or is larger than the diameter of the plunger portion 3008 of the straining device 3006. At the open side 3004 of the opening 3003, a chamfer 3009 may assist in guiding the plunger portion 3008 through the opening 3003. The plunger portion 3008 is slightly narrower that the smallest diameter of the opening in the frame while the handle portion 3007 is wider that the chamfer 3009 of the opening 3003, thus acting as a stop to limit straining of a dressing to a predetermined amount when the handle portion 3007 abuts the open side 3004 of the frame 3001 (see FIG. 24E)

Figure 15E:
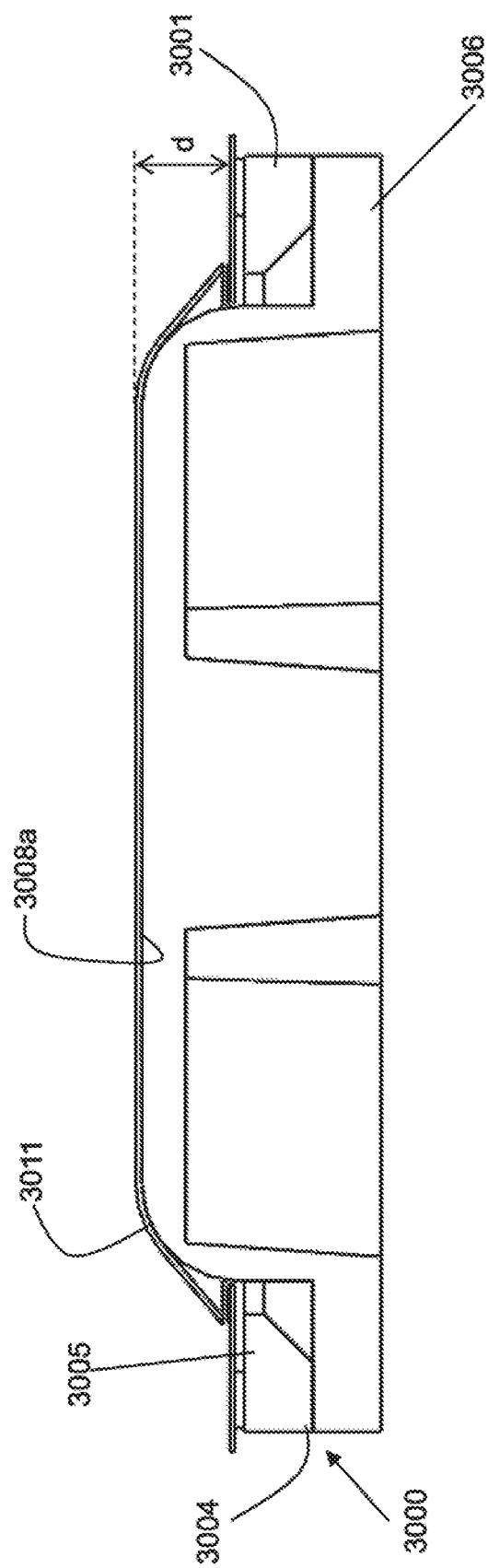
FIG. 15E is a cross-sectional view of a tensioning member straining a dressing of the dressing assembly of the dressing assembly and tensioning device of FIG. 18A.

In FIG. 15E the tensioning device 3000 is shown straining the dressing 3011. The plunger portion 3008 is inserted through the opening until the handle portion 3007 abuts the open side 3004 of the frame 3001. The plunger portion 3008 extrudes past the dressing surface 3005 to which the dressing 3011 is coupled or attached to thereby strain the dressing 3011. The end 3008*a* of the plunger portion 3008 extends past the opening side of the frame a predetermined distance d, thus straining the dressing 3011 a predetermined amount. The area of the end 3008*a* of the plunger and the distance d determine the amount of strain applied to the dressing 3011.

Figure 15F:
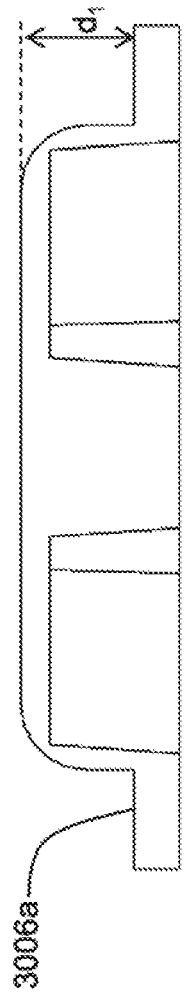
FIG. 15F illustrates a strain plunger.
Figure 15G:
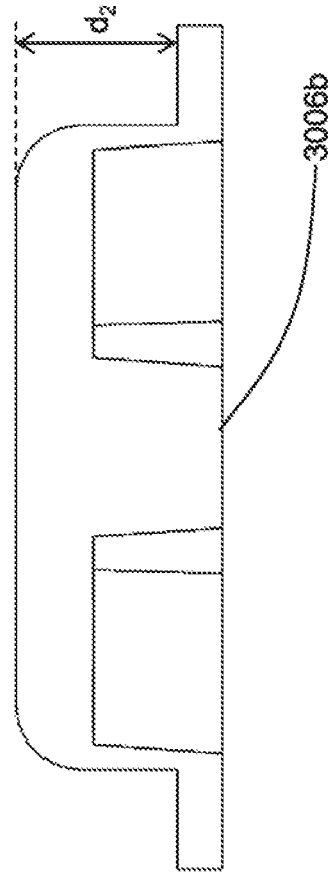
FIG. 15G illustrates a strain plunger.

As shown in FIGS. 15F and 15G a plurality of straining structures 3006*a* and 3006*b* constructed similarly to straining structure 3006, are shown each with different side wall lengths d1 and d2 respectively. The amount the plunger portions extend past the dressing side 3005 of the frame 3001 will determine the amount of strain imparted to the dressing. Each of the straining structures 3006*a* and 3006*b* impart different predetermined amounts of strain to a dressing. According to variations, a straining device imparting a predetermined amount of strain to a dressing may be selected from a plurality of straining devices each delivering a predetermined amount of strain. According to variations, a kit comprising at least one dressing assembly and support and a plurality of straining structures each imparting different amounts of predetermined strained to a dressing may be provided.

Once the dressing 3011 is strained, the tensioning device 3000 may be used to apply the dressing 3011 to a subject.

The dressing 3011 includes a layer of a skin adhesive 3021 such as a pressure sensitive adhesive e.g., as described herein, on an outwardly facing surface 3020 of the dressing 3011. An adhesive liner may be positioned over the adhesive layer and removed prior to straining.

Figure 15H:
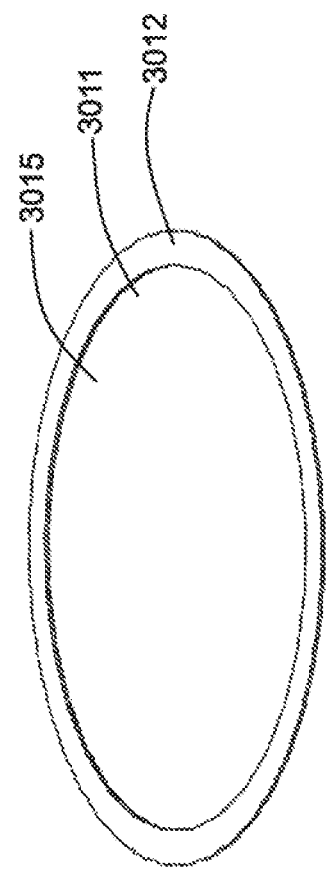
FIG. 15H illustrates an attachment ring.

After application of the dressing 3011, the dressing 3011 may be detached or separated from the tensioning device 3000 and the attachment sheet or ring 3012 using a removal structure 3030. As shown in FIGS. 15A to 15D the attachment sheet or ring 3012 includes a circumferential perforation 3031 and pull tab 3032. The perforation 3031 is located circumferentially inside of the attachment points where the adhesive 3014 attaches the attachment sheet 3012 to the frame 3001. When the pull tab 3032 is pulled, the dressing 3011 is separated from the attachment sheet 3012 and the tensioning device 3000 may then be removed leaving the dressing 3011 on the skin. FIG. 15H illustrates a dressing 3011 that is applied to a skin surface. A portion of the attachment ring 3012 may be removed or may remain on the frame facing surface 3015 of the dressing 3011 after it has been applied to the skin.

In FIGS. 15A to 15F, the dressing, attachment sheet, attachment structures, frame, frame opening, and plunger portions are illustrated in a circular shape. Other round shapes or curved contours may be used as well.

FIG. 15H illustrates a frame 3001a and a dressing 3011a releasably attached to the frame 3001a with attachment structures 3013a, and positioned over opening 3003a in the frame 3001a. The dressing 3011a is relatively rectangular but may be of any desired size and shape that may or may not be different from the shape of the opening 3003a and/or attachment structure(s) 3013a. The opening 3003a is circular, arced or curved and is configured to receive a plunger of a straining structure to strain the dressing 3011a. Attachment structure or structures 3013a may or may not include an attachment sheet or attachment ring and may comprise one or more attachment features. The attachment structure(s) 3013a are positioned about the opening 3003a in a shape that generally matches the shape of the opening, Different or selectable straining structures that may include a plunger, may be used to strain the dressing 3011a as described herein.

Figure 15K:
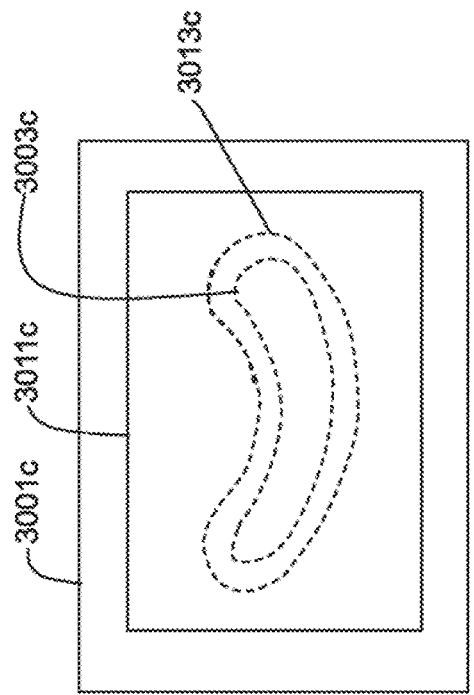
FIGS. 15I to 15M illustrate various exemplary embodiments of frame with attached dressings, from the dressing side of the frame.
Figure 15L:
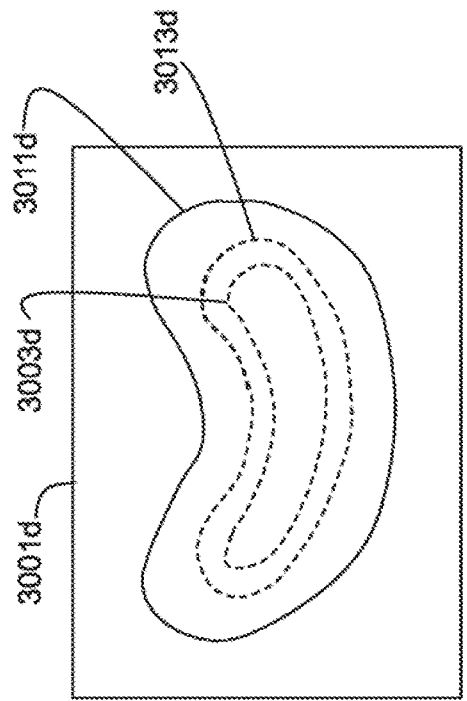
Figure 15I:
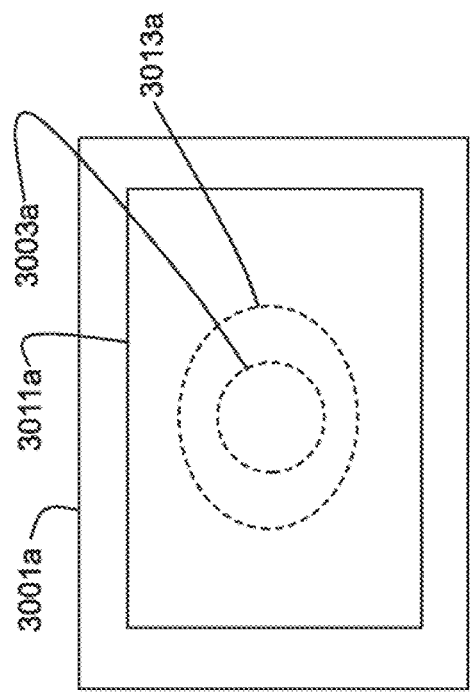

FIG. 15I illustrates a frame 3001b and a dressing 3011b releasably attached to the frame 3001b with attachment structures 3013h, and positioned over opening 3003b in the frame 3001b. The dressing 3011b is oval shaped but may be of any desired shape. The attachment structure 3013b shape generally matches or follows the shape of the edges of the dressing. Attachment structure or structures 3013b may or may not include an attachment sheet or attachment ring and may comprise one or more attachment features. The opening 3003b is circular, arced or curved but may be of any other desired shape. The opening 3003b is configured to receive a plunger of a straining structure to strain the dressing 3011b. Different or selectable straining structures that may include a plunger, may be used to strain the dressing 3011b as described herein.

Figure 15J:
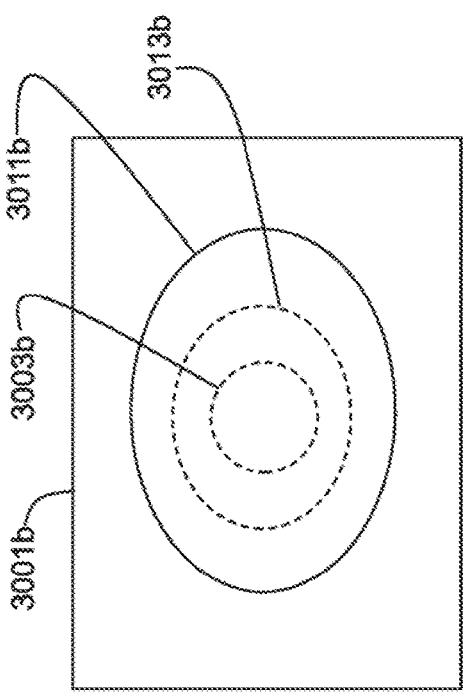
Figure 15M:
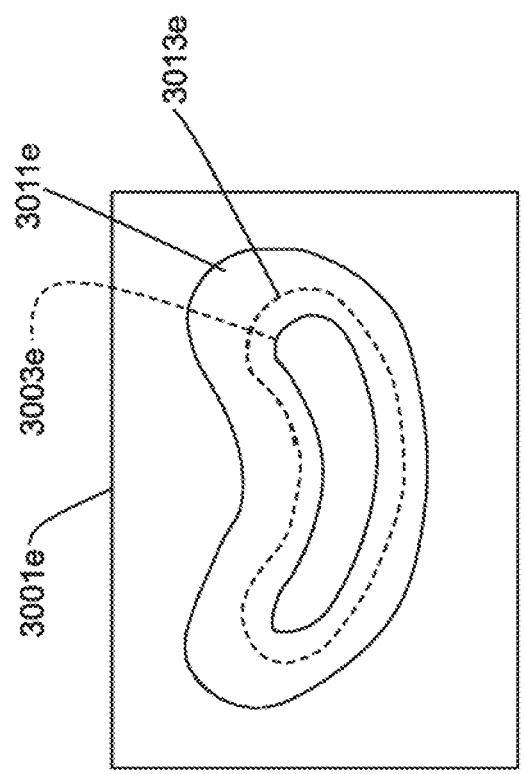

FIG. 15J illustrates a frame 3001c and a dressing 3011c releasably attached to the frame 3001c with attachment structures 3013c, and positioned over opening 3003c in the frame 3001c. The dressing 3011c is relatively rectangular but may be of any desired size and shape that may or may not be different from the shape of the opening 3003c and/or attachment structure(s) 3013c. The opening 3003c is irregularly shaped and is configured to receive a plunger of a straining structure to strain the dressing 3011c. Attachment structure or structures 3013c may or may not include an attachment sheet or attachment ring and may comprises one or more attachment features. The attachment structure(s) 3013c are positioned about the opening 3003c in a shape that generally matches the shape of the opening 3003c. Different or selectable straining structures that may include a plunger, may be used to strain the dressing 3011c as described herein.

FIG. 15K illustrates a frame 3001d and a dressing 3011d releasably attached to the frame 3001d with attachment structures 3013d, and positioned over opening 3003d in the frame 3001d. The dressing 3011d is irregularly shaped but may be of any desired shape. The attachment structure 3013d shape generally matches or follows the shape of the edges of the dressing 3011d. Attachment structure or structures 3013d may or may not include an attachment sheet or attachment ring and may comprise one or more attachment features. The opening 3003d is rectangular but may be of any other desired shape. The opening 3003d is configured to receive a plunger of a straining structure to strain the dressing 3011d. Different or selectable straining structures that may include a plunger, may be used to strain the dressing 3011d as described herein.

FIG. 24L illustrates a frame 3001e and a dressing 3011e releasably attached to the frame 3001e with attachment structures 3013e, and positioned over opening 3003e in the frame 3001e. The dressing 3011 is irregularly shaped and includes a plurality of curved edges having different radii. While the attachment structures generally follow the shape of the dressing 3011e, orthogonal distances between the dressing lateral edges and the attachment structure(s) may vary depending upon the radius at a particular point. For example, a distance d1 is greater at a location where the radius is shorter and a distance d2 is less at a location where the radius is greater. The distance d1 is greater at a location where the edge of the dressing curves in or is concave while the distance d2 is less at a location where the edge of the dress cures out or is convex. The opening 3003e is configured to receive a plunger of a straining structure to strain the dressing 3011e. Different or selectable straining structures that may include a plunger, may be used to strain the dressing 3011e as described herein.

While the frames in FIGS. 15H to 15L are schematically shown with rectangles, the shape of the frame may vary. Alternatively, the frame may comprise a circle, oval, egg, oblong, rectangle, square, triangle or other polygon, trapezoid, kidney bean, apple, clover, butterfly or pear shape and others mentioned elsewhere herein.

Referring to FIGS. 16A to 16G, a tensioning device or radially tensioning device 4000 is illustrated that may be used to apply a radial strain to variably curved or arced of a dressing geometry by applying a radially tensioning or straining force continuously or at different points defining or along a curved or arced portions, perimeters, or edges of the dressing 4011. The tensioning device 4000 may be used to evenly distribute strain radially across the dressing. According to variations, an applied multiaxial strain may or may not be relatively uniform in a radial direction from center points of arcs or curves of a dressing.

A tensioning member 4000 comprises a straining structure 4006 and a frame 4001. The straining structure 4006 comprises a handle portion 4007 and a plunger portion 4008. The frame 4001 comprises a support element 4002 having an opening 4003 configured to receive the plunger portion 4008 of the straining structure 4006 which is configured to fit within and extend through the opening 4003 of the frame 4001. A plurality of portions 4041, 4042, 4043, 4044, 4045 of a cross section of the opening 4003 have an arced or curved shape that may be matched by the shape of the plunger portion 4008. Each of a plurality of arced or curved section may or may not have a different radius from the radii of the other of the plurality of arced or curved sections.

A dressing assembly 4010 comprises a dressing 4011 removably coupled to an attachment sheet or attachment ring 4012. Prior to straining the dressing 4011, the attachment sheet or ring 4012 of the dressing assembly 4010 may be attached via an attachment structure 4013 to the frame 4001 over the circumference of the opening 4003 of the frame 4001. The attachment structure 4013 may include or be coupled to the attachment sheet or ring 4012. As shown in FIG. 16D, the attachment sheet or ring 4012 may be attached to the frame 4001 by way of an adhesive 4014 such as, e.g. an LDPE adhesive.

The attachment structure or structures 4013 are positioned or located in a shaped configuration about the attachment ring 4012 so that the tensioning forces applied to the dressing assembly 4010 and dressing 4011 may be applied radially with respect to the arced or curved shaped portions.

In some variations the attachment structures may comprise one or more mechanisms or elements configured to facilitate separation, release, removal or detachment of the dressing from the applicator or tensioning device, other attachment elements, or other portions of the dressing assembly, including but not limited to the separation devices and methods described herein. Release elements or releasable attachment structures may include but are not limited to pockets and tabs, hook and loop mechanism, hooks, angled bars, pivoting, rolling, rocking or sliding features associated with or coupled to attachment structures, adhesives, removable adhesives, adhesive tapes or other adhesive devices, pegs, rip cords, towel bar configurations, sliding pins, friction locks, cam locks, vacuum or suction devices, snap connectors, carpet tack, press fit connections or other connections, levers, latches, locking members, spring members, for example, or other mechanisms such as cutters or rip cords or other structures or features to facilitate tearing, cutting or separation of attachment structures or elements perforated or otherwise severable structures, that permit removal of dressing from the applicator, other portions of the dressing assembly and/or attachment structures, features, elements or portions They may be self-releasing latches or spring members. They may be actuated when a pressure member is applied to a skin treatment device prior to removing the applicator. They may be manually actuated.

In FIG. 16D, the straining structure 4006 is shown just prior to straining, and positioned facing the open side 4004 of the frame 4001 with the dressing assembly 4010 attached to an opposing dressing side 4005 of the frame 4001. At the dressing side 4005, the opening 4003 of the frame 4001 has a relatively smaller diameter that matches or is larger than the diameter of the plunger portion 4008 of the straining device 4006. At the open side 4004 of the opening 4003, a chamfer 4009 may assist in guiding the plunger portion 4008 through the opening 4003. The plunger portion 4008 is slightly narrower that the smallest diameter of the opening in the frame while the handle portion 4007 is wider that the chamfer 4009 of the opening 4003, thus acting as a stop to limit straining of a dressing to a predetermined amount when the handle portion 4007 abuts the open side 4004 of the frame 4001 (see FIG. 16F). Guide pins 4060 extend out of the open side 4004 of the frame 4001 and may be inserted into corresponding guide holes 4070 of the straining structure 4006 in order to align the shapes of the frame 4001 and straining structure 4006 as the dressing is strained.

Figure 16A:
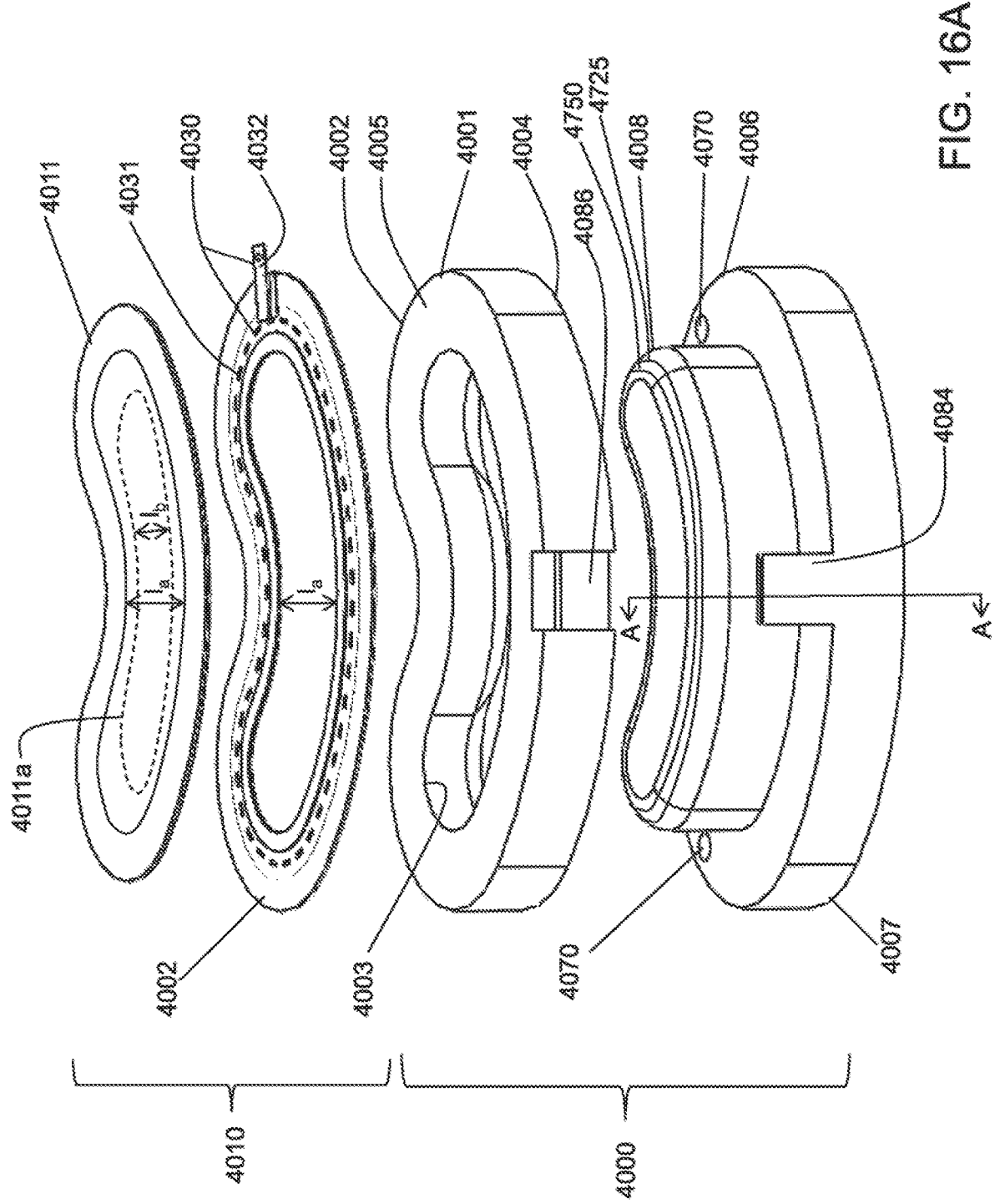
FIG. 16A is an exploded perspective view in a first direction of a tensioning device and dressing assembly.
Figure 16B:
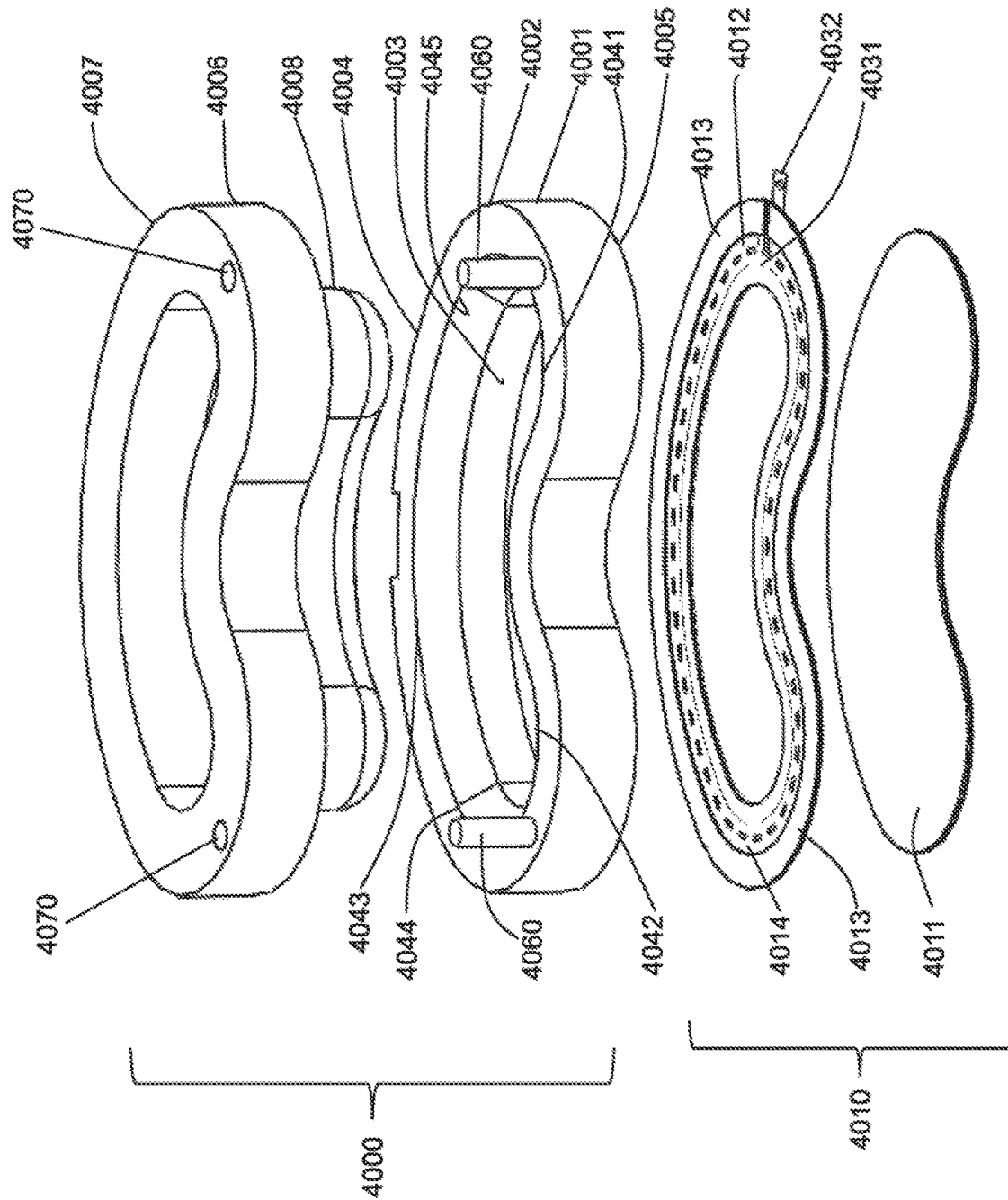
FIG. 16B is an exploded perspective view in an opposite direction of the tensioning device and dressing assembly of FIG. 16A.
Figure 16F:
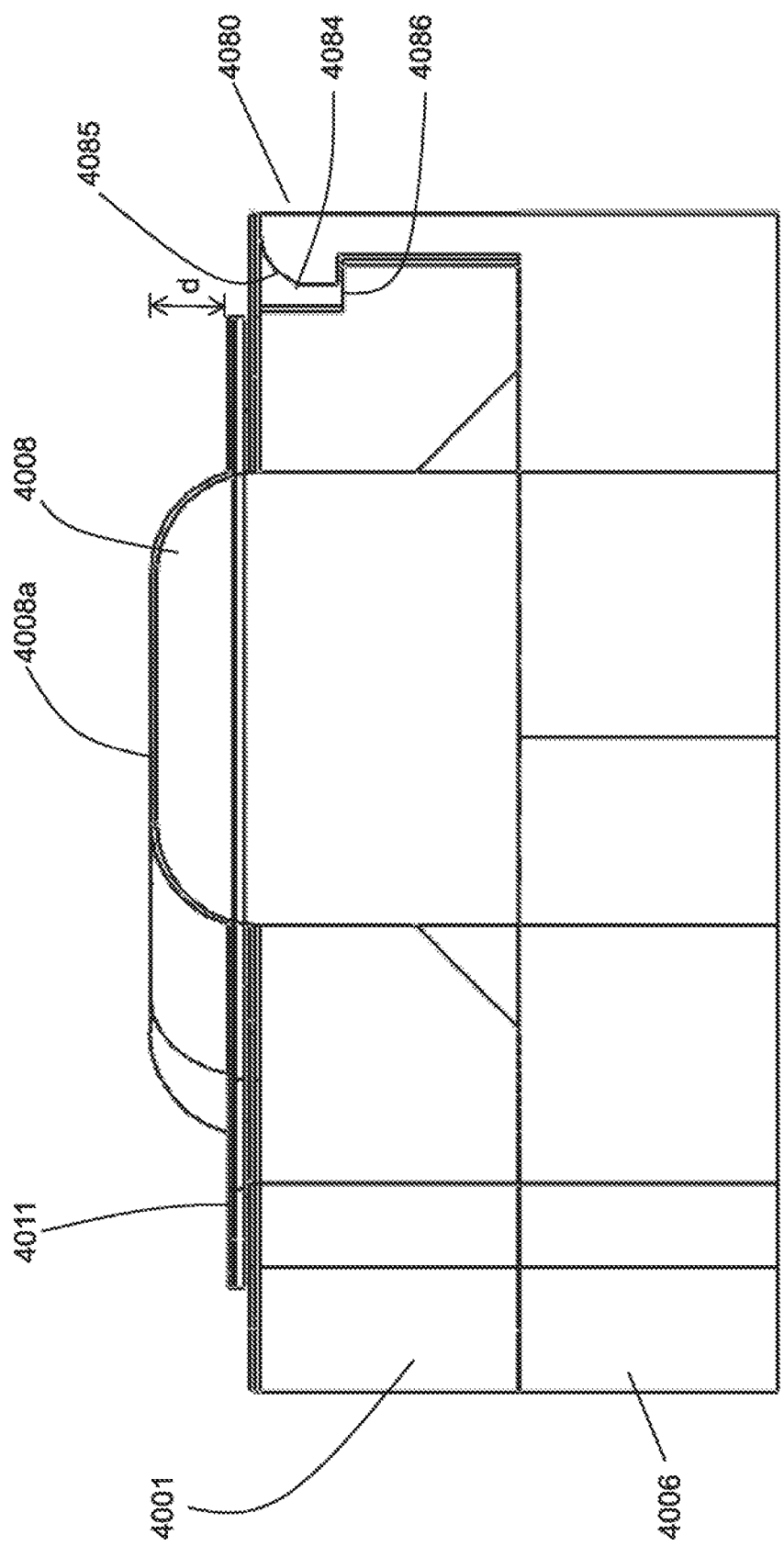
FIG. 16F is a cross sectional view of FIG. 16C along lines B-B.

In FIG. 16F, the tensioning device 4000 is shown straining the dressing 4011. The plunger portion 4008 is inserted through the opening until the handle portion 4007 abuts the open side 4004 of the frame 4001. The plunger portion 4008 extrudes past the dressing surface 4005 to which the dressing 4011 is coupled or attached to thereby strain the dressing 4011. The end 4008a of the plunger portion 4008 extends past the opening side of the frame a predetermined distance d or amount thus straining the dressing 4011 a predetermined amount. A locking mechanism 4080 locks the straining structure 4006 in this position to the frame 4001. The locking mechanism 4080 comprises a catch 4084 on the straining structure with a cam surface 4085. The catch 4084 engages a shelf 4086 on the frame 4001 after the handle portion 4007 is positioned abutting the open side 4004 of the frame 4001.

The area of the end 4008a of the plunger and the distance d determine the amount of strain applied to the dressing 4011. The amount the plunger portions extend past the dressing side 4005 of the frame 4001 will determine the amount of strain imparted to the dressing According to variations, a straining device imparting a predetermined amount of strain to a dressing may be selected from a plurality of straining devices each delivering a predetermined amount of strain. According to variations, a kit comprising at least one dressing assembly and support and a plurality of straining structures each imparting different amounts of predetermined strained to a dressing may be provided.

Once the dressing 4011 is strained, the tensioning device 4000 may be used to apply the dressing 4011 to a subject.

The dressing 4011 includes a layer of a skin adhesive 4021 such as a pressure sensitive adhesive e.g., as described herein, on an outwardly facing surface 4020 of the dressing 4011. An adhesive liner may be positioned over the adhesive layer and removed prior to straining.

Figure 16G:
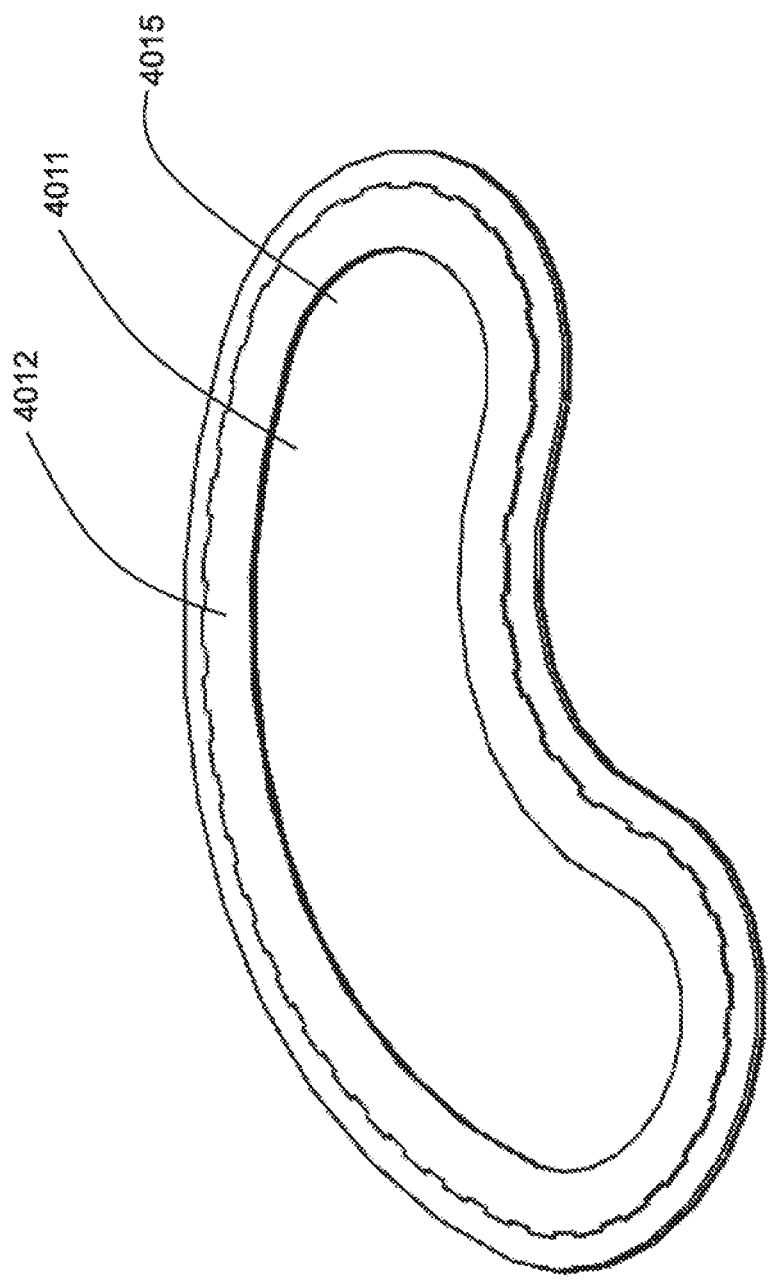
FIG. 16G schematically depicts the dressing at a treatment site and after the applicator has been removed.

After application of the dressing 4011, the dressing 4011 may be detached or separated from the tensioning device 4000 and the attachment sheet or ring 4012 using a removal structure 4030. As shown in FIGS. 16A, 16B and 16D the attachment sheet or ring 4012 includes a circumferential perforation 4031 and pull tab 4032. The perforation 4031 is located circumferentially inside of the attachment points where the adhesive 4014 attaches the attachment sheet 4012 to the frame 4001. When the pull tab 4032 is pulled, the dressing 4011 is separated from the attachment sheet 4012 and the tensioning device 4000 may then be removed leaving the dressing 4011 on the skin. FIG. 16G illustrates a dressing 4011 that is applied to a skin surface. A portion of the attachment ring 4012 may be removed or may remain on the frame facing surface 4015 of the dressing 4011 after it has been applied to the skin.

In FIGS. 16A to 16G, the dressing, attachment sheet, attachment structures, frame, frame opening, and plunger portions are illustrated in a kidney-shape where lateral edges have curved portions of varying radius. Other shapes or curved contours may be used as well.

Figure 18:
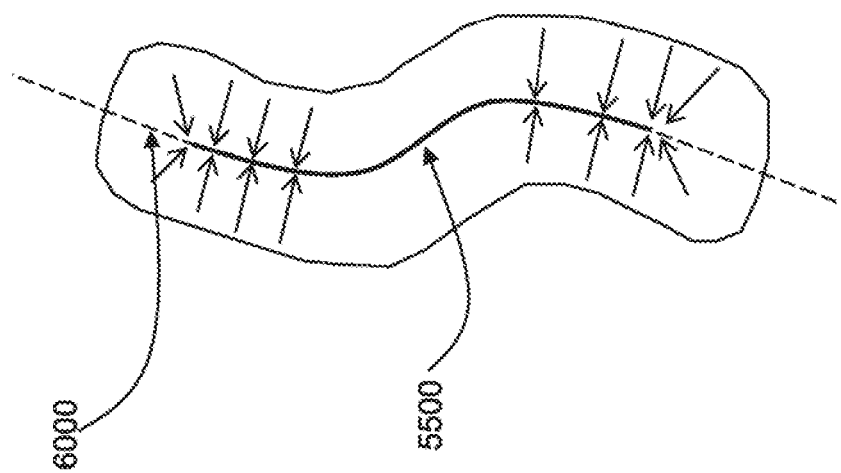
FIG. 18 illustrates a customized dressing.
Figure 17:
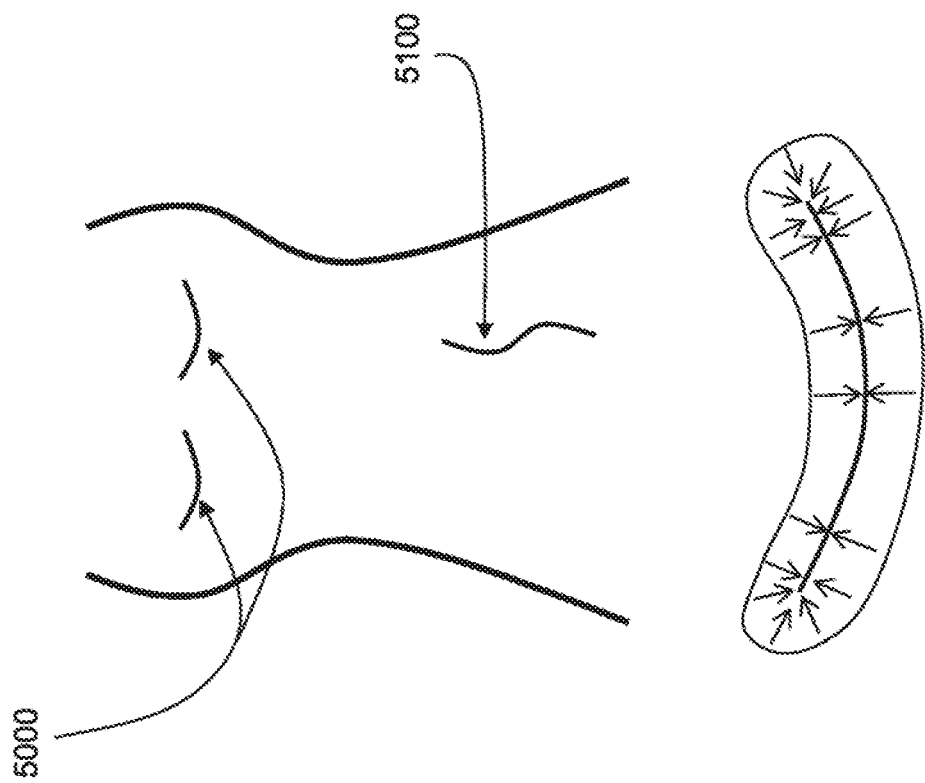
FIG. 17 illustrates a subject with non-linear incisions.

FIG. 17 illustrates a subject with non-linear incisions or wounds. With first incisions 5000, a dressing such as, e.g., the dressing 4011 of FIGS. 16A to 16G, may be used, for example, in breast reconstruction procedures or other surgery where the dressing shape generally matches an incision shape or contours of the subject's body. Wound 5100 has a non-linear and irregular shape. A dressing 5500 such as illustrated in FIG. 18 may be customized to match follow the shape of the wound 5100. The dressing 5500 may be strained using a tensioning device with a matching shape in a manner similar to that described with respect to FIGS. 15A to 15H and FIGS. 16A to 16G. Thus when aligned with and over the wound 5100, the dressing may apply a generally perpendicular compressive force inwardly towards the irregular line or shape of the wound 5100.

A center line of the dressing may be defined as generally originating from the shape of or line(s) of the wound or incision. A matching tensioning device may be constructed, for example, using 3-D printing to customize the shape of the tensioning device to match that of the custom dressing 5500. The custom dressing may similarly be 3-D printed or cut in a desired shape. Accordingly the dressing 5500 may be strained to provide perpendicular compressive strains to a center line 6000 of a dressing 5500. In some variations, the dressing 5500 may be strained such that the compressive strains to the center line 6000 is equidistant from edges using a line perpendicular to the center line 6000.

The dressing 4011 may alternatively be separated from the frame 4001 using a cutter 4700 that extends from the handle 4007 through circumferential channel 4750 in the plunger 3008. (FIGS. 16B, 16H and 16I) The cutters 4700 may be actuated from the handle so that they extend out of the side walls 4900 of the plunger 4008 to cut the dressing. The channel openings 4725 are positioned below the end 4008a of the plunger 4008 so that when the cutter 4700 is actuated it cuts in a planar direction substantially spaced from the skin of a subject.

Figure 16H:
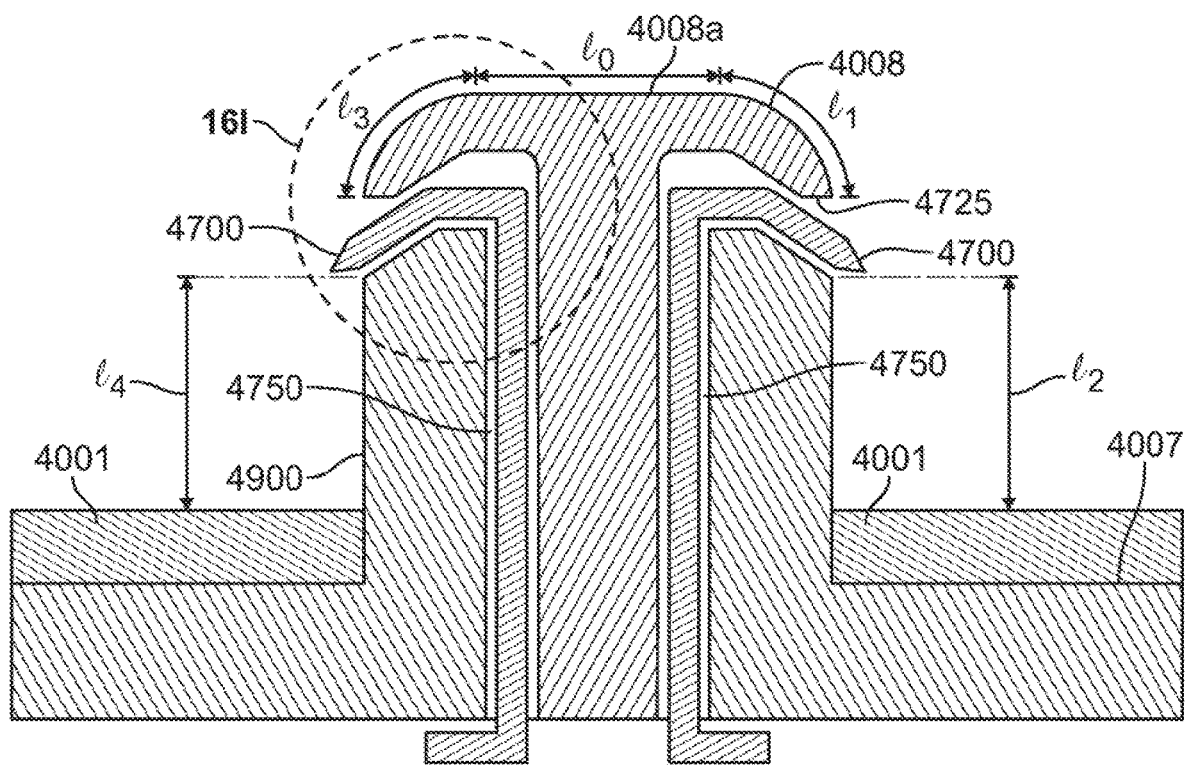
FIG. 16H is a cross section along lines A-A of the straining structure of FIG. 16A.
Figure 16I:
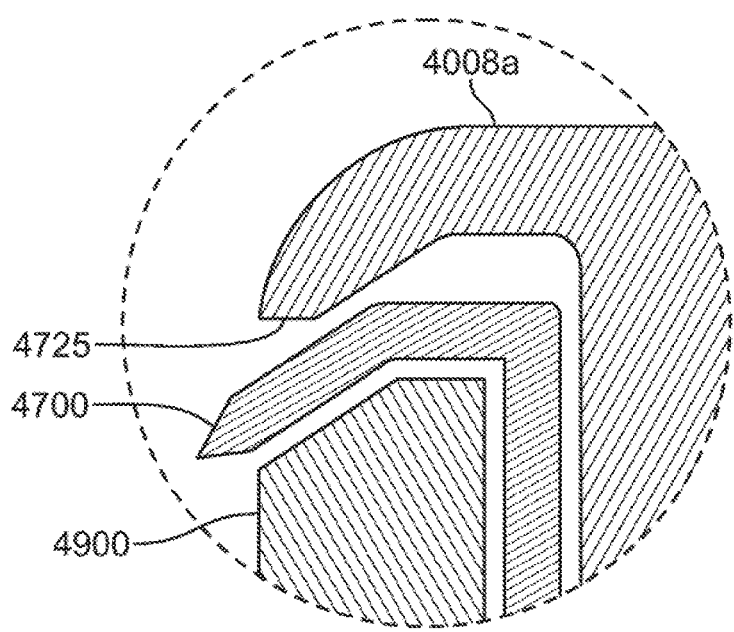
FIG. 16I is an enlarged view of Section B of FIG. 16H.

The width of the dressing 4011 on an orthogonal line with respect to the edges of the dressing 4011 prior to cutting is 1a. The length of the dressing 4011 on the orthogonal line after cutting at the cut line 4011a is 1b. As shown in FIG. 16H, the total length of a strained dressing along lines A-A is equal to the length of the sides walls 14, 13, 11, 12 plus the length of the top wall 10. In this example, the length 14 is equal to opposing side wall length 12; the length 13 of the curved portion of the side wall is equal to the length 11 of the opposing curved portion of the side wall.

Figure 16J:
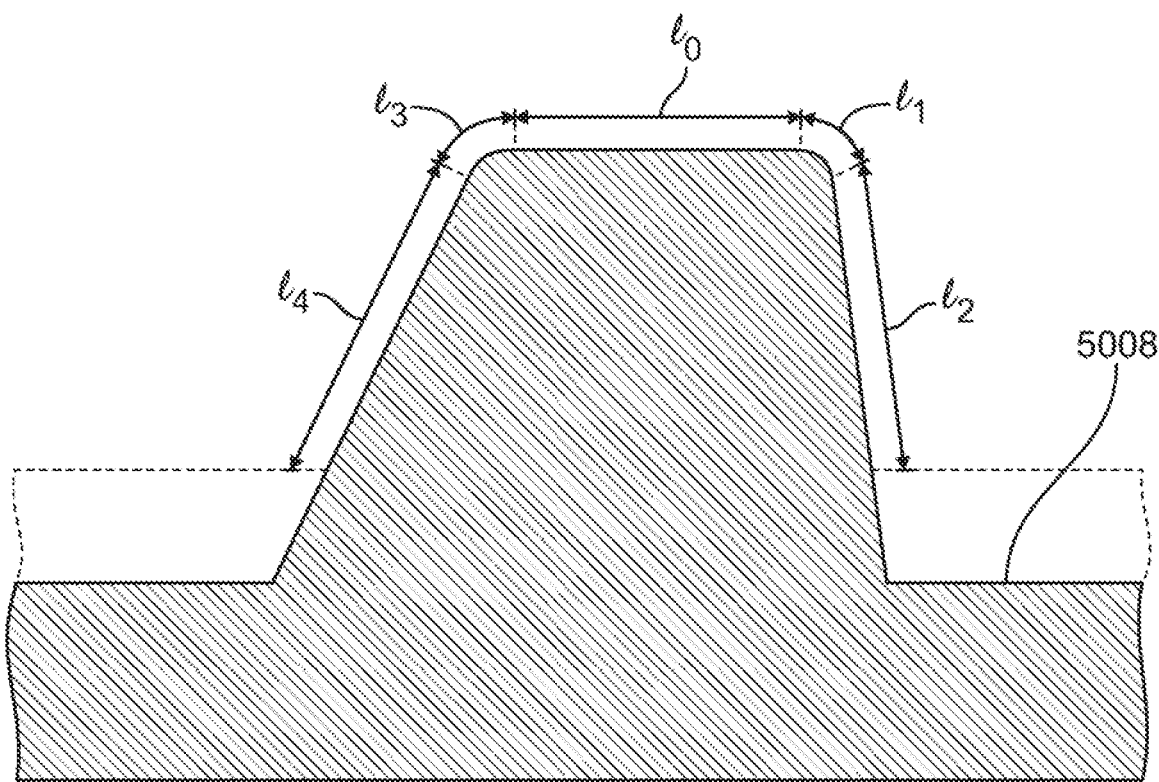
FIG. 16J is a schematic cross section of a variation of a straining structure.

FIG. 16J illustrates a cross sectional view of a variation of a plunger 5008. The total length of a strained dressing along a line orthogonal to its edges may be represented by the length of the side walls 14, 13, 11, 12 plus the length of the top wall 10 of the plunger 5008 at the depicted cross section. The total strain may be unevenly distributed across the length based on the configuration of the side walls of the plunger 5008. In this example, the length 14 is longer than opposing side wall length 12; the length 13 of the curved portion of the side wall is longer than the length 11 of the opposing curved portion of the side wall.

Figure 16K:
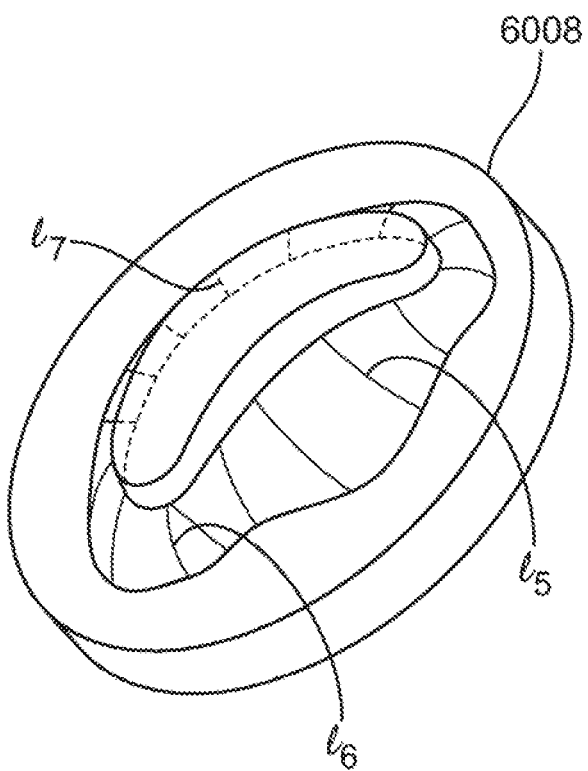
FIG. 16K is a perspective view of a variation of a straining structure.

FIG. 16K illustrates a perspective view of a plunger 6008 that may be used with the frame 4001 and dressing assembly 4010. The length 15 of the side wall at the curved portion of the plunger 6008 is greater than the length 16 of the side wall at a convex curved portion of the plunger 6008 for example, to counteract possible bunch if elastic dressing material on the inside radius of the bend. The length 15 of the side wall at the concave curved portion of the plunger 6008 is greater than length 17 of the side wall at a convex curved portion of the plunger 6008.

One or more hemostatic or coagulative agents may be applied to, or otherwise integrated with dressing to help reduce bleeding. Potential agents include chitosan, calcium-loaded zeolite, microfibrillar collagen, cellulose, anhydrous aluminum sulfate, silver nitrate, potassium alum, titanium oxide, fibrinogen, epinephrine, calcium alginate, poly-N-acetyl glucosamine, thrombin, coagulation factor(s) (e.g. II, VII, VII, X, XIII, Von Willebrand factor), procoagulants (e.g. propyl gallate), antifibrinolytics (e.g. epsilon aminocaproic acid), and the like. In some variations, the agents may be freeze-dried and integrated into the dressing and activated upon contact with blood or other fluid. In some further variations, an activating agent may be applied to the dressing or the treatment site before the dressing is used on the subject. In still other examples, the hemostatic agent may be applied separately and directly to the wound before application of the dressing, or after application to the dressing via a catheter or tube. The devices may also comprise one or more other agents that may be any suitable agent that may be useful in aiding in some aspect of the wound healing process. For example, the active agent may be a pharmaceutical compound, a protein (e.g., a growth factor), a vitamin (e.g., vitamin E), or combinations thereof. Of course, the devices may comprise more than one medicament or agents, and the devices may deliver one or more medicaments or agents. An example of such medicament may include, but is not limited to various antibiotics (including but not limited to cephalosporins, bactitracin, polyxyxin B sulfate, neomycin, polysporin), antiseptics (such as iodine solutions, silver sulfadiazine, chlorhexidine), antifungals (such as nystatin), antiproliferative agents (sirolimus, tacrolimus, zotarolimus, biolimus, paclitaxel), grow factors (such as VEGF) and other treatments (e.g. botulism toxin).

According to variations the various assemblies or devices described herein may provide a temporary wound dressing that may be applied before a wound is closed. The assembly may be configured to apply a dressing to a wound and to use the applicator to apply pressure to the wound before removing or separating the applicator, tensioning device or dressing carrier, base or support from the dressing. According to this variation which may be provided with any of the embodiments described below, the applicator has sufficient rigidity to distribute a relatively even or firm force to a wound by applying pressure to the applicator when and/or after the dressing is applied to a wound. According to a variation, such dressing may include a coagulation agent or other agent or medicament, for example as described herein. According to another variation, margins as described herein, are provided on such a device between a dressing and edges used to manipulate the device.

While this invention has been particularly shown and described with references to embodiments thereof, it will be understood h those skilled in the art that various changes in form and details may be made therein without departing from the scope of the invention. For all of the embodiments described above, the steps of the methods need not be performed sequentially.

The invention claimed is:

1. A method of straining a dressing, comprising:
straining a first dressing region along a first axis located in a first plane;
straining a second dressing region along a second axis located in a second plane different from the first plane, wherein the second dressing region is coupled to the first dressing region;
applying the first dressing region to a treatment site; and releasing at least some strain from the first dressing region; and
separating a third dressing region from the second dressing region to relieve at least some strain in the first dressing region, wherein the third dressing region encloses the second dressing region.

2. The method of claim 1, wherein the straining of the first and second dressing regions are pre-determined strains.

3. The method of claim 1, wherein the second dressing region encloses the first dressing region.

4. The method of claim 1, wherein the straining of the first and second dressing regions occurs prior to the applying the first dressing region to the treatment site.

5. The method of claim 1, wherein the releasing at least some strain in the first dressing region releases substantially all of the strain in the second dressing region.

6. A method of straining a dressing, comprising:
radially straining a dressing to a pre-determined strain using an applicator, before applying the dressing to a treatment site, wherein radially straining the dressing to a pre-determined strain comprises radially straining the dressing out-of-plane before applying the dressing to the treatment site;
adhering the strained dressing to the treatment site; and detaching the dressing from the applicator.

7. The method of claim 6, wherein radially straining the dressing comprises:

straining a first dressing region of the dressing along a first axis located in a first plane; and straining a second dressing region of the dressing along a second axis located in a second plane different from the first plane.

8. The method of claim 7, wherein the second dressing region encloses the first dressing region.

9. The method of claim 8, wherein detaching the dressing from the applicator comprises separating a third dressing region from the second dressing region.

10. The method of claim 9, wherein the third dressing region encloses the second dressing region.

11. The method of claim 7, further comprising releasing at least some strain in the first dressing region upon detaching the dressing from the applicator.

12. The method of claim 11, wherein releasing at least some strain the first dressing region releases substantially all of the strain in the second dressing region.

* * * * *